(12) United States Patent
Greenberg et al.

(10) Patent No.: US 7,452,869 B2
(45) Date of Patent: Nov. 18, 2008

(54) NIP3 FAMILY OF PROTEINS

(75) Inventors: Arnold H. Greenberg, deceased, late of Winnipeg (CA); by Faye Hellner, legal representative, Winnipeg (CA); Jonathan D. Geiger, Winnipeg (CA); Lorrie A. Kirshenbaum, Winnipeg (CA)

(73) Assignee: University of Manitoba, Winnipeg Manitoba (CA)

( * ) Notice: Subject to any disclaimer, the term of this patent is extended or adjusted under 35 U.S.C. 154(b) by 370 days.

(21) Appl. No.: 10/290,461

(22) Filed: Nov. 8, 2002

(65) Prior Publication Data

US 2003/0203867 A1 Oct. 30, 2003

Related U.S. Application Data

(63) Continuation-in-part of application No. PCT/US01/21043, filed on Jun. 29, 2001.

(60) Provisional application No. 60/344,196, filed on Dec. 28, 2001, provisional application No. 60/348,135, filed on Nov. 9, 2001, provisional application No. 60/219,554, filed on Jul. 20, 2000, provisional application No. 60/215,643, filed on Jun. 30, 2000.

(51) Int. Cl.
*A61K 38/17* (2006.01)
*A61K 48/00* (2006.01)
*C12N 15/86* (2006.01)

(52) U.S. Cl. .......................... 514/44; 514/12; 435/69.9; 435/325; 435/320.1

(58) Field of Classification Search ............... 424/146.1
See application file for complete search history.

(56) References Cited

U.S. PATENT DOCUMENTS 5,847,093 A * 12/1998 Bandman et al.
5,858,678 A * 1/1999 Chinnadurai

FOREIGN PATENT DOCUMENTS

| EP | 0733706 | 9/1996 |
|---|---|---|
| WO | WO98/29447 | 7/1998 |
| WO | WO 9927093 A2 * | 6/1999 |

OTHER PUBLICATIONS

Freshney, Culture of Animal Cells, A Manual of Basic Technique, Alan R. Liss, Inc. 1983, New York, pp. 3 and 4.*
Pitts et al. American Journal of Physiology-Heart 287:1801-1812, 2004.*

(Continued)

*Primary Examiner*—Lorraine Spector
*Assistant Examiner*—Claire Kaufman
(74) *Attorney, Agent, or Firm*—Bereskin & Parr; Michaline Gravelle; Carmela DeLuca

(57) ABSTRACT

Methods and compositions for modulating necrosis and for treating neurological and cardiovascular diseases are described. The inventors have shown that BNIP3 is involved in cell necrosis and cell death involved in cardiovascular and neurological diseases.

25 Claims, 35 Drawing Sheets

OTHER PUBLICATIONS

Thomas et al. Nature Reviews: Genetics 4:346-358, 2003.*
Thompson, FDA Consumer Magazine, pp. 1-6 (www.fda.gov/fdac/features/2000/500_gene.html) Sep.-Oct. 2000.*
Thomas et al. Nature Biotechnology 18:39-42, 2000.*
Chen et al. Journal of Experimental Medicine 186(12): 1975-1983, 1997.*
Ray et al. Journal of Biological Chemistry 275(2): 1439-1448, Jan. 2000.*
Vande Velde et al. Molecular and Cellular Biology 20(15): 5454-5468, Aug. 2000.*
Guo et al. Cell Death and Proliferation 8: 367-376, 2001.*
Regula et al. Journal of Molecular and Cellular Cardiology 38: 3-13, 2005.*
Hamacher-Brady et al., Response to myocardial ischemia/reperfusion injury involves Bnip3 and autophagy, Cell Death and Diff., 14:146-157, 2007.*
Tygai et al., Internalization of HIV-1 Tat requires cell surface heparin sulfate proteoglycans, J. Biol. Chem. 276(5):3254-3261, 2001.*
Bucci et al. In vivo delivery of the caveolin-1 scaffolding domain inhibits nitric oxide syhtnesis and reduces inflammation, Nat. Med. 6(12):1362-1367, 2000.*
Bernardi, P. L. et al. 1999. "Mitochondria and cell death: mechanistic aspects and methodological issues" Eur. J. Biochem. 264: 687-701.
Bialik, S. et al. "The mitochondrial apoptotic pathway is activated by serum and glucose deprivation in cardiac myocyres" Circ. Res. Sep. 3, 1999 85: 403-414.
Bossy-Wetzel, E. et al., 1998. "Mitochondrial cytochrome c release in apoptosis occurs upstream of DEVD-specific caspase activation and independeritly of mitochondrial transmembrane depolarization" EMBRO J. 17: 37-49.
Boyd, J. M. et al. 1994. "Adenovirus E1B 19 kDa and Bcl-2 proteins interact with a common set of cellular proteins" Cell 79: 341-351.
Capecchi, M. R. "Altering the genome by homologous recombination" Science 244: 1288-1292 (1989).
Chautan, M. et al., 1999. "Interdigital cell death can occur through a necrotic and caspase-independent pathway" Curr. Biol. 9: 967-970.
Chen, G. et al., 1999 "Nix and Nip3 Form a Subfamily of Pro-apoptotic Mitochondrial Proteins", J. Biol. Chem. 274: 7-10.
Chen, G. et al., 1997 "The E1B 19K Bcl-2 binding protein NIP3 is a dimeric mitochondrial protein that activates apoptosis", J. Exp. Med. 186: 1975-1983.
Chi, S. et al., 1999. "Oncogenic Ras triggers cell suicide through the activation of a caspase-independent cell death program in human cancer cells" Oncogene 18: 2281-2290.
Cizeau, J. et al. "The C. elegans orthologue ceBNIP3 interacts with CED-9 and CED-3 but kills through a BH3- and caspase-independent mechanism" Oncogene Nov. 16, 2000; 19 (Srinivasula, S. M. et al., 1998): 5453-63.
Cregg, J. M. et al. "Recent Advances in the Expression of Foreign Genes in *Pichia pastoris*", Bio/Technology 11: 905-910, 1993.
Crompton, M. 1999 "The mitochondrial permeability transition pore and its role in cell death" Biochem. J. 341: 233-249.
Datta, S. R. et al., 1997 "Akt Phosphorylation of BAD Couples Survival Signals to the Cell-Intrinsic Death Machinery", Cell 91: 231-241.
Davies, N. P. et al., "Targeted alterations in yeast articial chromosomes for inter-species gene transfer", Nucleic Acids Research, vol. 20, No. 11, pp. 2693-2698 (1992).
Déas, O. et al., 1998 "Caspase-Independent Cell Death Induced by Anti-CD2 or Staurosporine in Activated Human Peripheral T Lymphocytes", J. Immunol. 161: 3375-3383.
de Moissac, D. et al., "Caspase Activation and Mitochondrial Cyrochrome C Release during Hypoxia-mediated Apoptosis of Adult Ventricular Myocytes" J. Mol. Cell Cardiol. 2000 32: 53-63.
Dickinson, P. et al., "High frequency gene targeting using insertional vectors", Human Molecular Genetics, vol. 2, No. 8, pp. 1299-1302 (1993).
Dixon, I. M., et al., "Sarcolemmal calcium transport in congestive heart failure due to myocardial infarction in rats", Am J Physiol. 1992; 262: H1387-H1394.

Earnshaw, W. C. et al., 1999, "Mammalian Caspases: Structure, Activation, Substrates, and Functions During Apoptosis" Annu. Rev. Biochem. 68: 383-424.
Finucane, D. M. et al., 1999, "Bax-induced Caspase Activation and Apoptosis via Cytochrome c Release from Mitochondria Is Inhibitable by Bcl-xL", J. Biol. Chem. 274: 2225-2233.
Goping, I. S. et al., 1998 "Regulated Targeting of BAX to Mitochondria", J. Cell. Biol. 143: 207-215.
Green, D. R. et al., 1998, "Mitochondria and Apoptosis", Science 281: 1309-1312.
Griffiths, G. J. et al., 1999, "Cell Damage-induced Conformational Changes of the Pro-Apoptotic Protein Bak In Vivo Precede the Onset of Apoptosis", J. Cell Biol. 144: 903-914.
Gross, A. et al., 1999, "BCL-2 family members and the mitochondria in apoptosis", Genes Dev. 13: 1899-1911.
Gurevich, R. M. et al., "Serpin Protein CrmA Suppresses Hypoxia-Mediated Apoptosis of Ventricular Myocytes" Circulation 2001; 103: 1984-1991.
Huston, J. S. et al., 1991 "Protein Engineering of Single-Chain Fv Analogs and Fusion Proteins", Methods in Enzymology, vol. 203: 46-88.
Hakem, R. et al., 1998, "Differential Requirement for Caspase 9 in Apoptotic Pathways In Vivo", Cell 94: 339-352.
Harada, H. et al., 1999, "Phosphorylation and Inactivation of BAD by Mitochondria-Anchored Protein Kinase A", Mol. Cell 3: 413-422.
Haughey, N. J. et al., (2001) "HIV-1 Tat through phosporylation of NMDA receptors potentiates glutamate excitotoxicity", Journal of Neurochemistry 78, 457-467.
Horvitz, H. R., 1999 "Genetic Control of Programmed Cell Death in the Menatode *Caenorhabditis elegans*", Cancer res. 59: 1701s-1706s.
Huxley, C. et al., "The Human HPRT Gene on a Yeast Artificial Chromosome Is Functional When Transferred to Mouse Cells by Cell Fusion", Genomics, 9: 742-750 (1991).
Imazu, T. et al., 1999, "Bcl-2/E1b 19 kDa-interacting protein 3-like protein (Bnip3L) interacts with Bcl-2/Bcl-$x_L$ and induces apoptosis by altering mitochondrial membrane permeability", Oncogene 18: 4523-4529.
Jakobovits, A. et al., "Germ-line transmission and expression of a human-derived yeast artificial chromosome", Nature, vol. 362, pp. 255-261 (1993).
Johnson, S. et al., 1991, "Construction of Single-Chain Fv Derivatives of Monoclonal Antibodies and Their Production in *Escherichia coli*", Methods in Enzymology, vol. 203: 88-99.
Kawahara, A. et al., 1998, "Caspase-independent Cell Killing by Fas-associated Protein with Death Domain", J. Cell Biol. 143: 1353-1360.
Kerr, J. F. R., et al., 1972, "Apoptosis: A Basic Biological Phenomenon With Wide-Ranging Implications in Tissue Kinetics", Br. J. Cancer 26: 239-257.
Kirshenbaum, L. A. et al., "The bcl-2 Gene Product Prevents Programmed Cell Death of Ventricular Myocytes", Circulation. 1997 96: 1580-1585.
Kirshenbaum, L. A. et al., "Adenovirus E1A Represses Cardiac Gene Transcription and Reactivates DNA Synthesis in Ventricular Myocytes, via Alternative Pocket Protein- and p300-binding Domains", J. Biol Chem. 1995; 270: 7791-7794.
Kirshenbaum, L. A., et al., "High Efficient Gene Transfer into Adult Ventricular Myocytes by Recombinant Adenovirus", J. Clin. Invest. 1993 92: 381-387.
Kirshenbaum, L. A., et al., "Increase in endogenous antioxidant enzymes protects hearts against reperfusion injury", Am J. Physiol. 1993; 265: H484-H493.
Kluck, R. M. et al., 1999, "The Pro-apoptotic Proteins, Bid and Bax, Cause a Limited Permeabilzation of the Mitochondrial Outer Membrane that is Enhanced by Cytosol", J. Cell. Biol. 147: 809-822.
Kroemer, G. et al., 1998, "The Mitochondrial Death/Life Regulator in Apoptosis and Necrosis", Annu. Rev. Physio. 60: 619-642.
Kroemer, G. et al., 1997, "Mitochondrial control of apoptosis", Immunology Today, vol. 18, No. 1, pp. 44-51.
Lamb, B. T. et al., "Introduction and expression of the 400 kilbase precursor amyloid protein gene in transgenic mice", Nature Genetics, vol. 5, pp. 22-29 (1993).

Lavoie, J. N. et al., 1998, "E4orf4, a Novel Adenovirus Death Factor That Induces p53-independent Apoptosis by a Pathway That is not Inhibited by zVAD-fmk", J. Cell. Biol. 140: 637-645.

Leist, M. et al., 1997, "Intracellular Adenosine Triphosphate (ATP) Concentration: A Switch in the Decision Between Apoptosis and Necrosis", J. Exp. Med. 185: 1481-1486.

Li, H. et al., 1998, "Cleavage of BID by Caspase 8 Mediates the Mitochondrial Damage in the Fas Pathway of Apoptosis", Cell 94: 491-501.

Li, P. et al., 1997, "Cytochrome c and dATP-Dependent Formation of Apaf-1/Caspase-9 Complex Initiates an Apoptotic Protease Cascade", Cell 91: 479-489.

Long, X. et al., "p53 and the Hypoxia-induced Apoptosis of Cultured Neonatal Rat Cardiac Myocytes", J. Clin. Invest. 1997; 99: 2635-2643.

Luo, X. et al., 1998, "Bid, a Bcl2 Interacting Protein, Mediates Cytochrome c Release from Mitochondria in Response to Activation of Cell Surface Death Receptors", Cell 94: 481-490.

Marzo, I. et al., 1998, "Bax and Adenine Nucleotide Translocator Cooperate in the Mitochondrial Control of Apoptosis", Science 281: 2027-2031.

Marzo, I. et al., 1998, "The Permeability Transition Pore Complex: A Target for Apoptosis Regulation by Caspases and Bcl-2-related Proteins", J. Exp. Med. 187: 1261-1271.

Matsushima, M. et al., 1998, "Isolation, Mapping, and Functional Analysis of a Novel Human cDNA (BNIP3L) Encoding a Protein Homologous to Human NIP3", Genes Chromosomes Cancer 21: 230-235.

McCarthy, N. J. et al., 1997, "Inhibition of Ced-3/ICE-related Proteases Does Not Prevent Cell Death Induced by Oncogenes, DNA Damage, or the Bcl-2 Homologue Bak", J. Cell. Biol. 136: 215-227.

McConkey, D. J., 1998, "Biochemical determinants of apoptosis and necrosis", Toxicol. Lett. 99: 157-168.

Miura, M., et al., 1993, "Induction of apoptosis in fibroblasts by IL-1 beta-convertin enzyme, a mammalian homolog of the C. elegans Cell Death Gene ced-3", Cell 75: 653-660.

Mustapha, S. et al., "A direct requirement of nuclear factor-$_\kappa$B for suppression of a apoptosis in venticular myocytes", Am J. Physiol Heart Circ Physiol. 2000; 279: H939-H945.

Narita, M., S. Shimizu, T. Ito, T. Chittenden, R. J. Lutz, H. Matsuda, and Y. Tsujimoto. 1998. Bax interacts with the permeability transition pore to induce permeability transition and cytochrome c release in isolated mitochondria. Proc. Natl. Acad. Sci. USA 95: 14681-14686.

Nguyen, M., D. G. Millar, V. W. Yong, S. J. Korsmeyer, and G. C. Shore. 1993. Targeting of Bc1-2 to the mitochondrial outer membrane by a COOH-terminal signal anchor sequence. J. Biol. Chem. 268: 25265-25268.

Nicotera, P., M. Leist, and E. Ferrando-May. 1998. Intracellular ATP, a switch in the decision between apoptosis and necrosis. Toxicol. Lett. 102103: 139-142.

Pearson and Choi, Expression of the human b-amyloid precursor protein gene from a yeast artificial chromosome in transgenic mice. Proc. Natl. Acad. Sci. USA, 1993. 90: 10578-82.

Ray R, Chen G, Vande Velde C, Cizeau J, Park JH, Reed JC, Gietz RD, Greenberg AH. BNIP3 heterodimerizes with Bcl-2/Bcl-X (L) and induces cell death independent of a Bcl-2 homology 3 (BH3) domain at both mitochondrial and nonmitochondrial sites. J Biol Chem. Jan. 14, 2000; 275 (2): 1439-48.

Rothstein,"Targeting, disruption, replacement, and allele rescue: integrative DNA transformation in yeast"in Methods in Enzvmoloav, vol. 194,"Guide to Yeast Genetics and Molecular Biology", eds. C. Guthrie and G. Fink, Academic Press, Inc., Chap. 19, pp. 281-301 (1991).

Schedl et al., "A yeast artificial chromosome covering the tyrosinase gene confers copy number-dependent expression in transgenic mice", Nature, vol. 362, pp. 258-261 (1993).

Strauss et al., "Germ line transmission of a yeast artificial chromosome spanning the murine ai (I) collagen locus", Science, vol. 259, pp. 1904-1907 (1993).

Tanaka M, Ito H, Adachi S, Akimoto H, Nishikawa T, Kasajima T, Marumo F, Hiroe M. Hypoxia induces apoptosis with enhanced expression of Fas antigen messenger RNA in cultured neonatal rat cardiomyocytes. Circ Res. 1994;75:426-433.

Vande Velde C, Cizeau J, Dubik D, Alimonti J, Brown T, Israels S, Hakem R, Greenberg AH. BNIP3 and genetic control of necrosis-like cell death through the mitochondrial permeability transition pore. Mol Cell Biol. Aug. 2000; 20 (15): 5454-68.

Minx, P. "Hypothetical 23.6 kD protein (accession No. Q09969)" EMBL Database 1996.

Tsunoda et al. "Effect of wild-type and mutated p53 and Id proteins on the induction of apoptosis by Adenovirus E1A, c-Myc, Bax and Nip3 in p53 null mouse cerebellum cells." Biochem. Biophys. Res., Comm., vol. 255, p. 722-730, 1999.

* cited by examiner

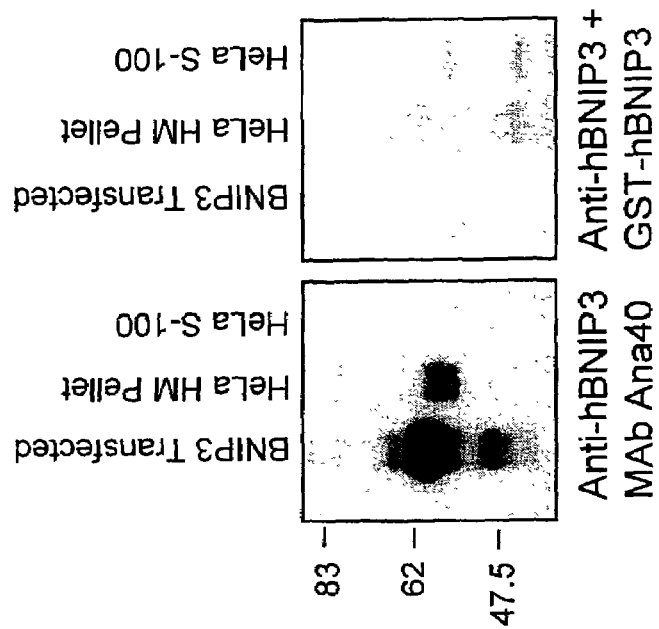
Figure 1A, right panel
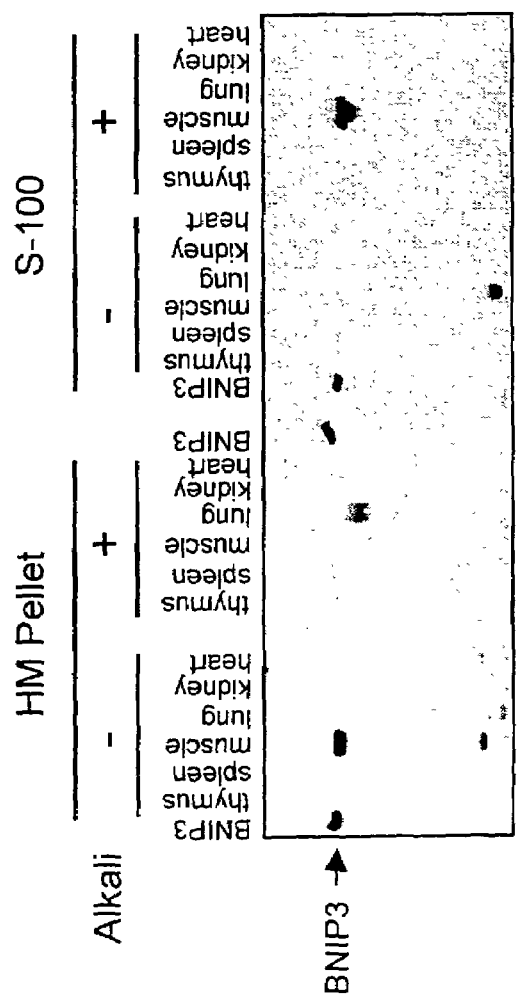
Figure 1A, left panel

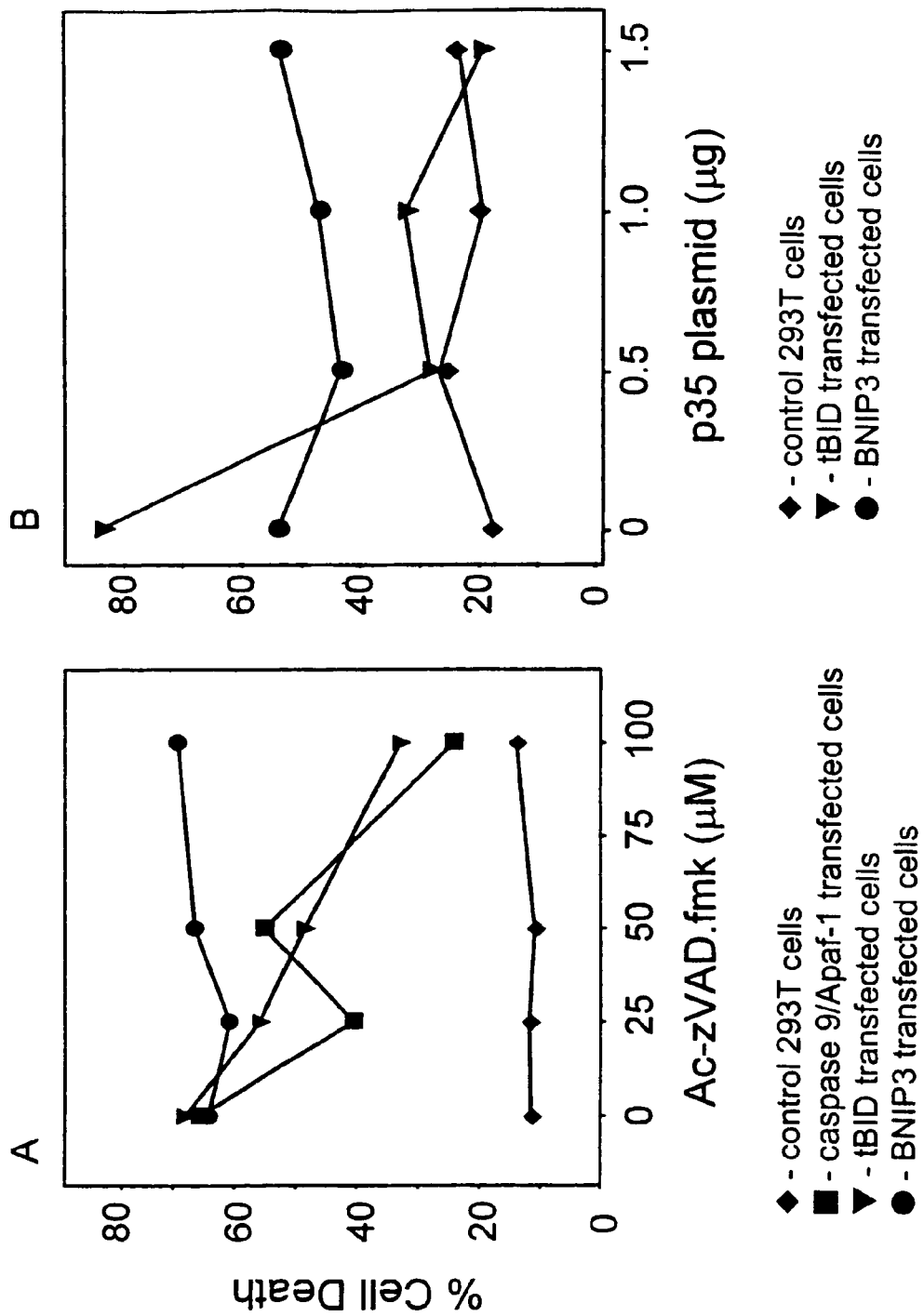
Figure 2A,B

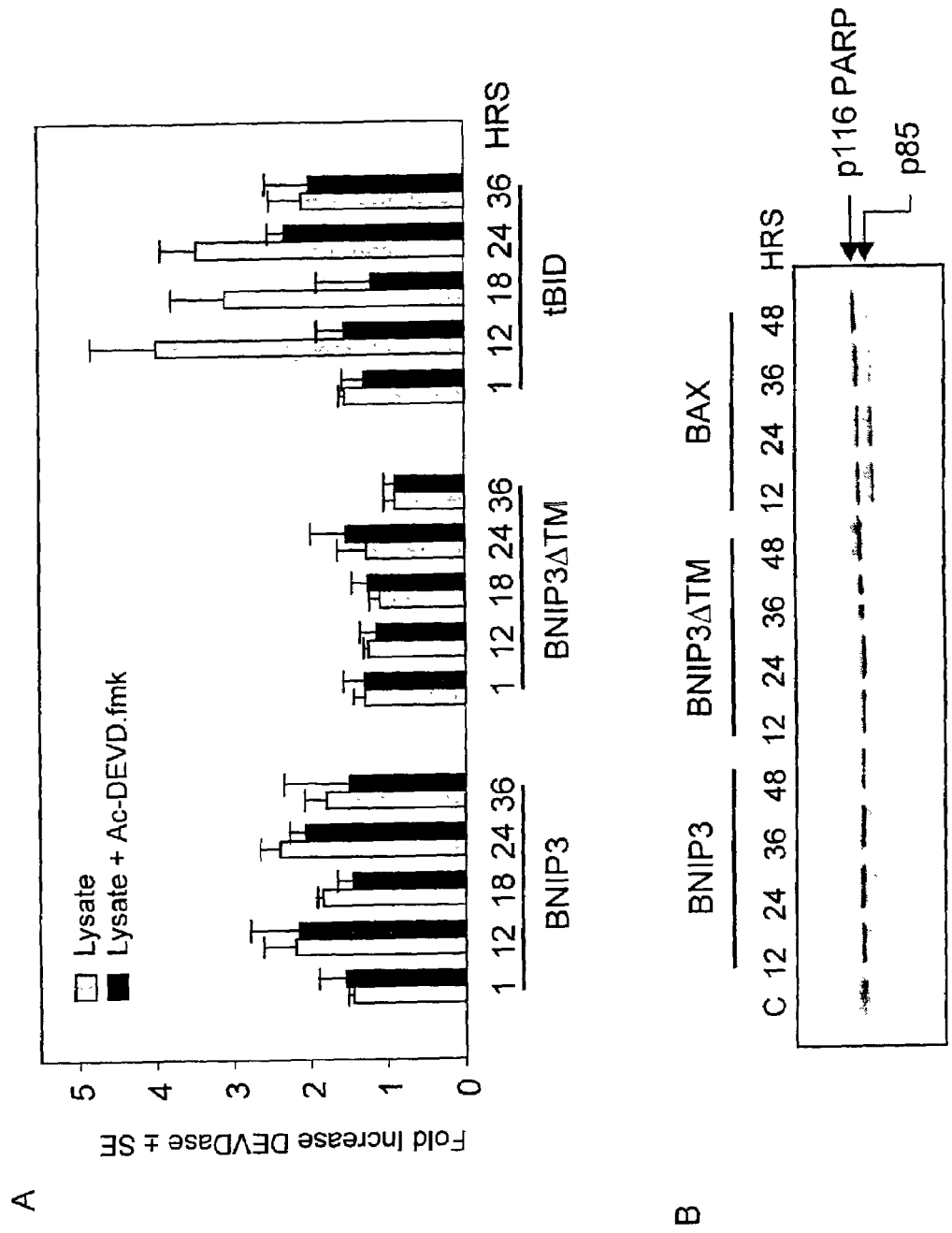
Figure 3A,B

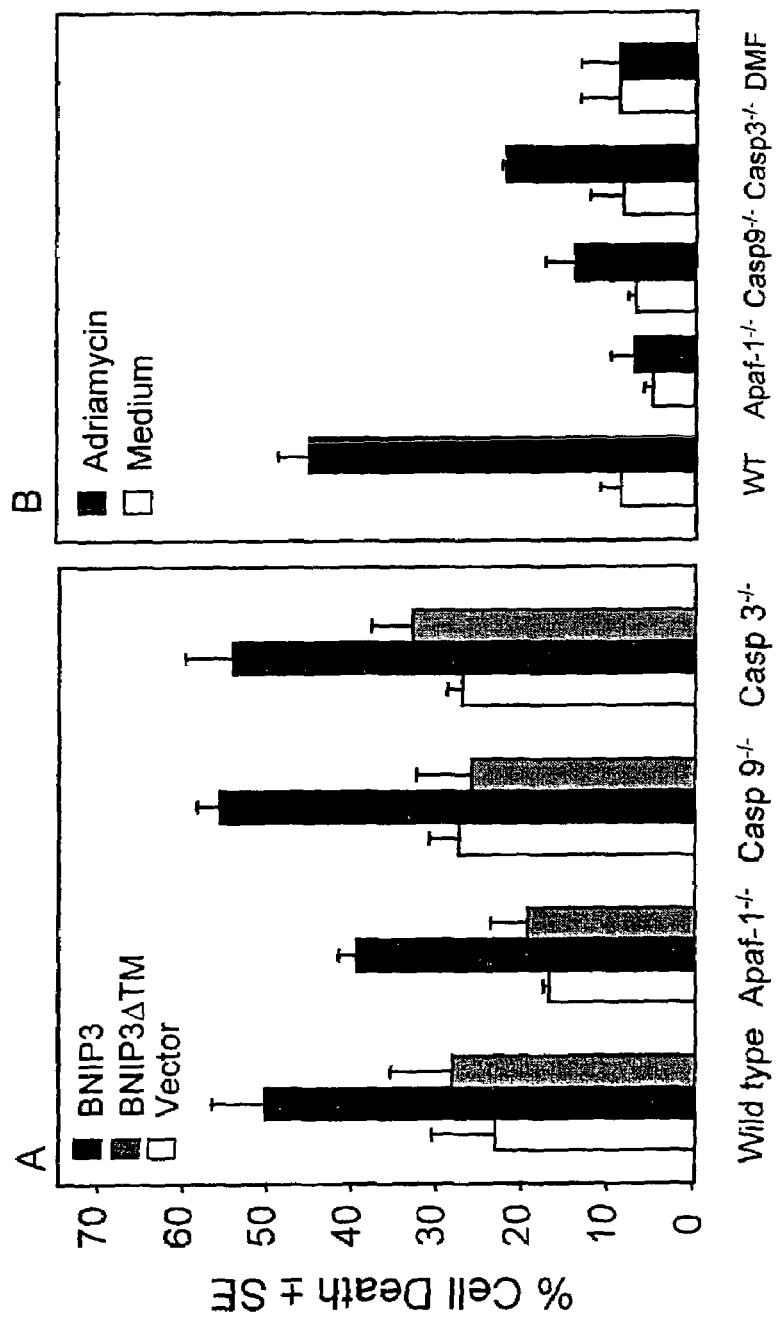
Figure 5A,B

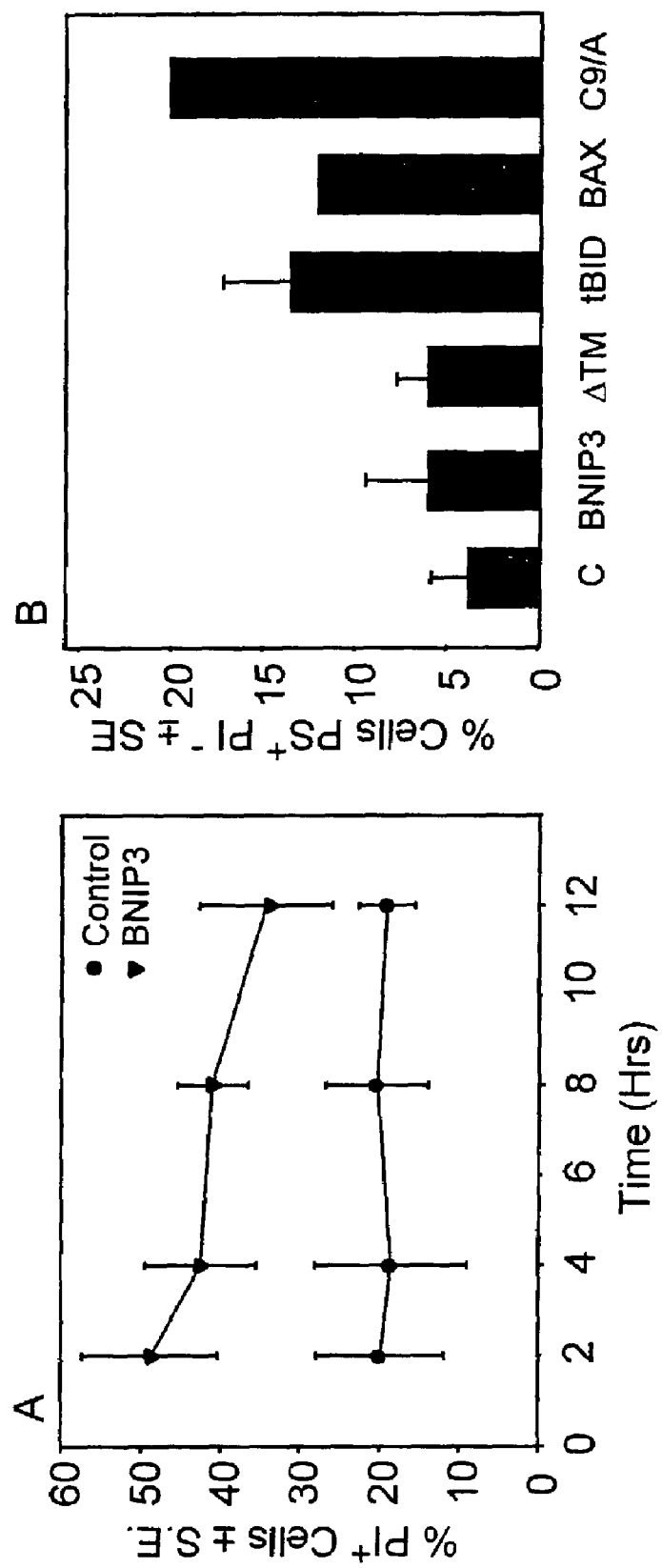
Figure 6 A,B

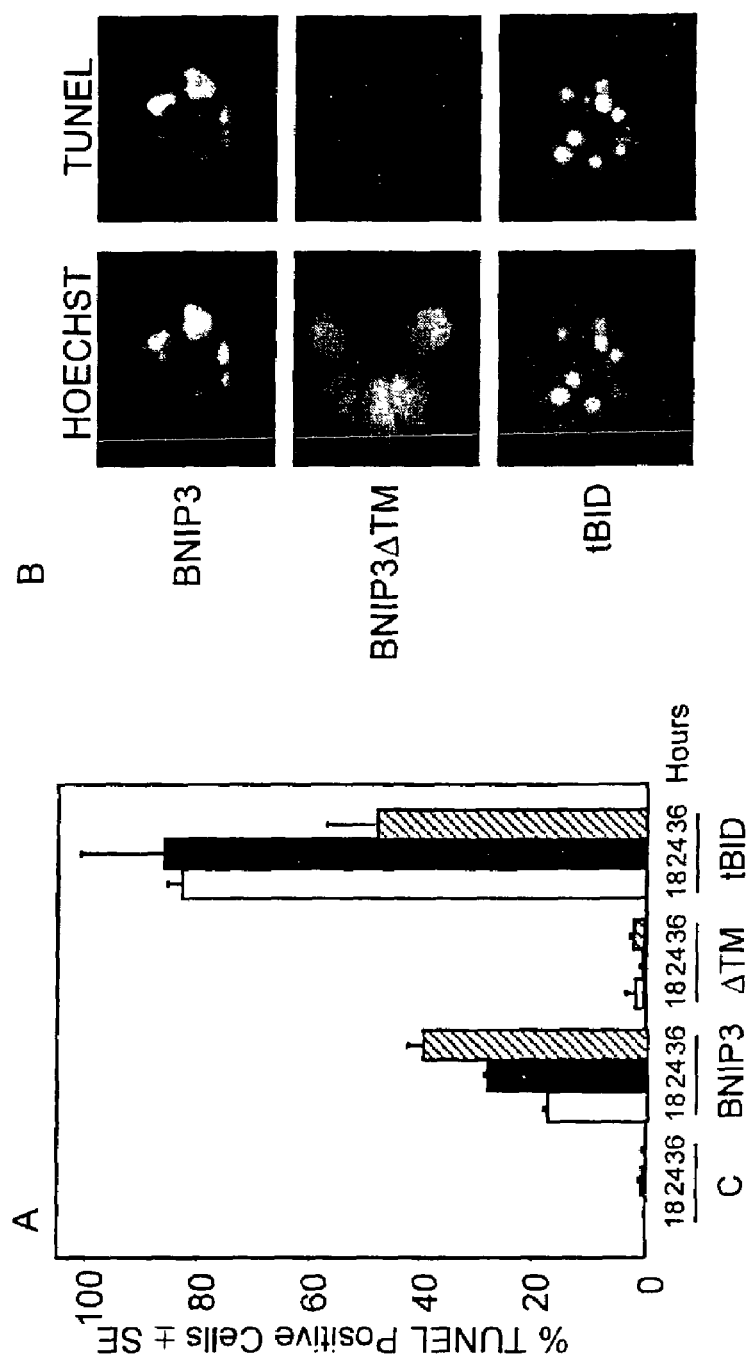
Figure 7A,B

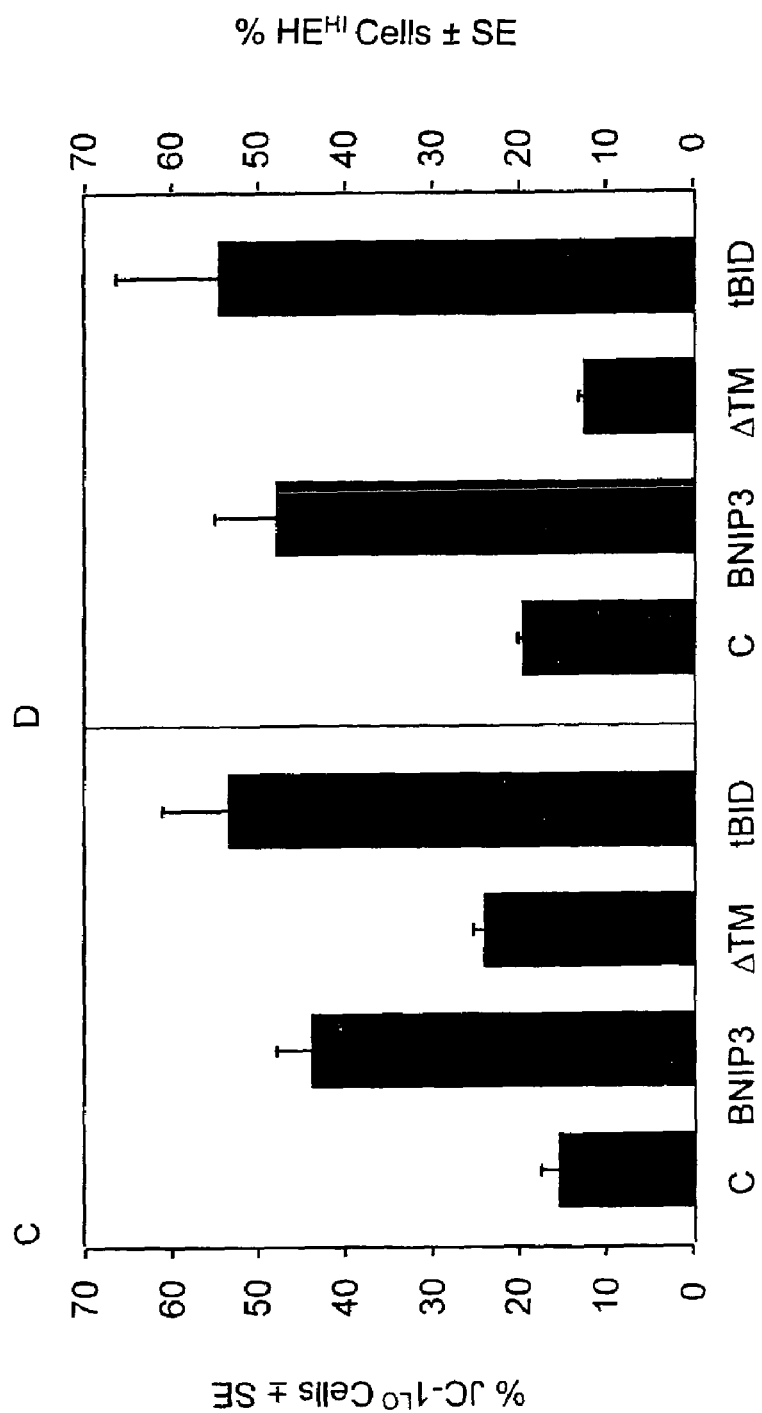
Figure 9 C,D

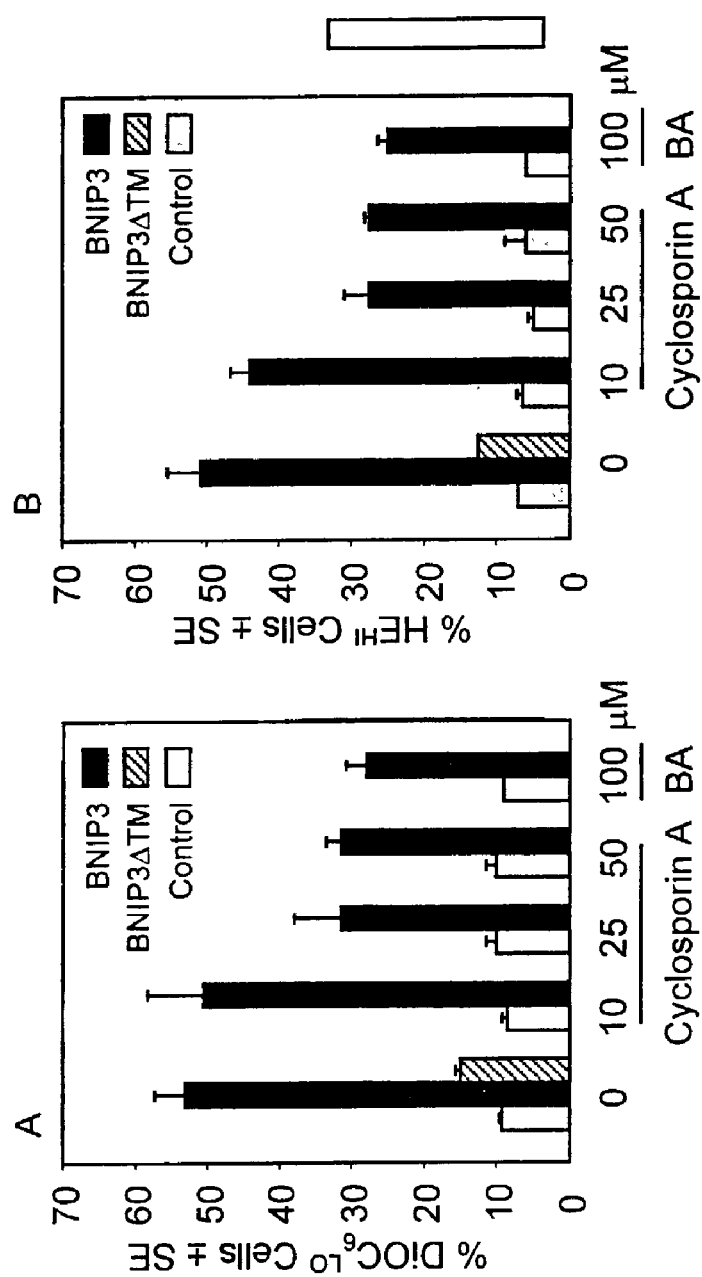
Figure 10A,B

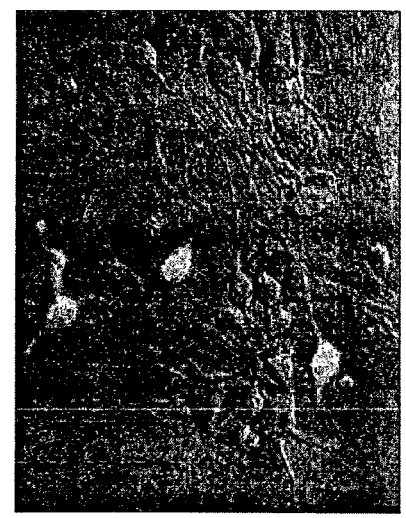
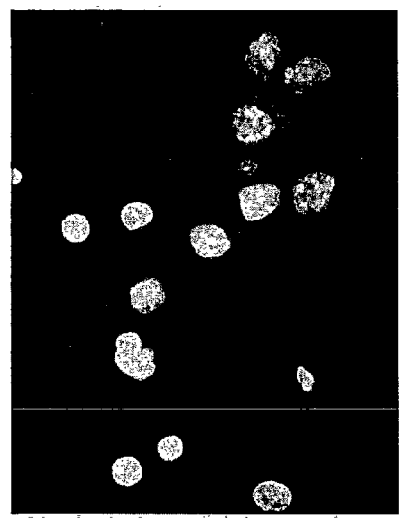
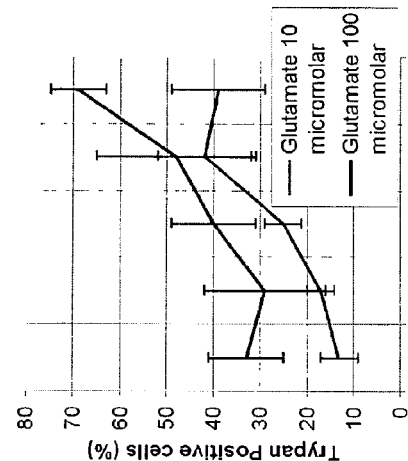
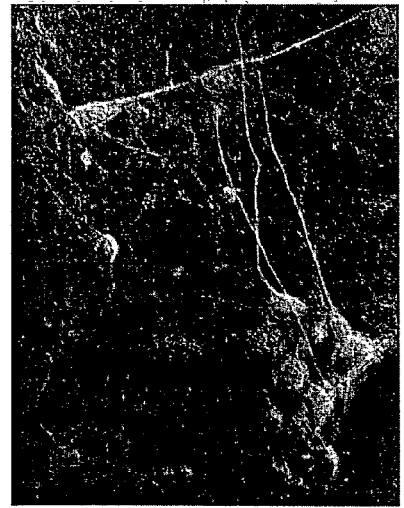
Figure 17

Figure 18
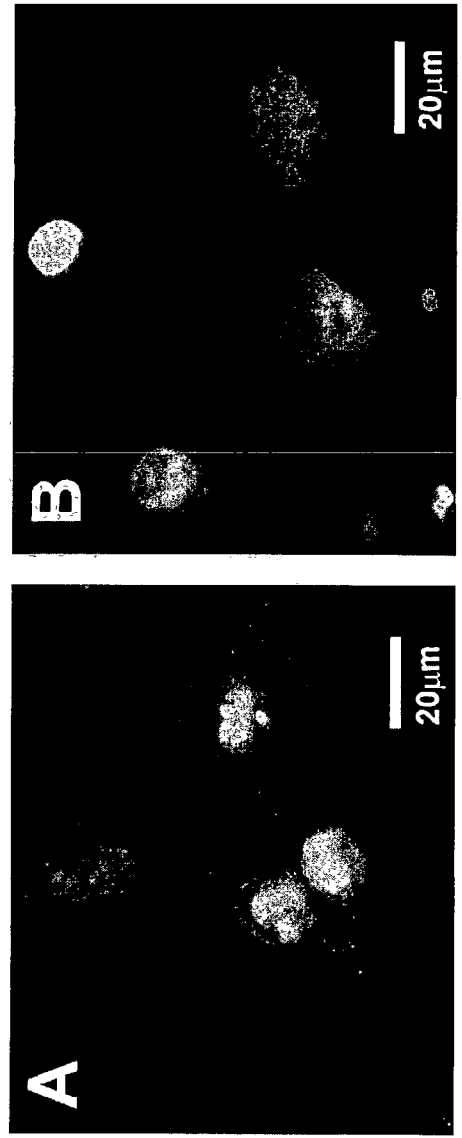
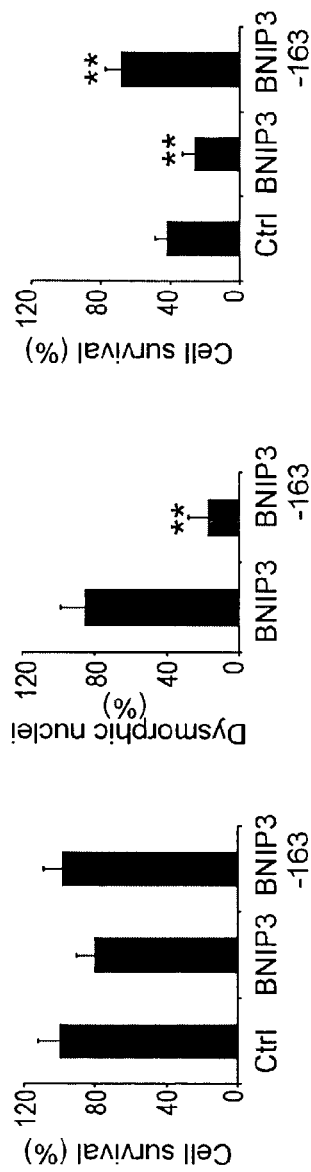

FIGURE 23
A
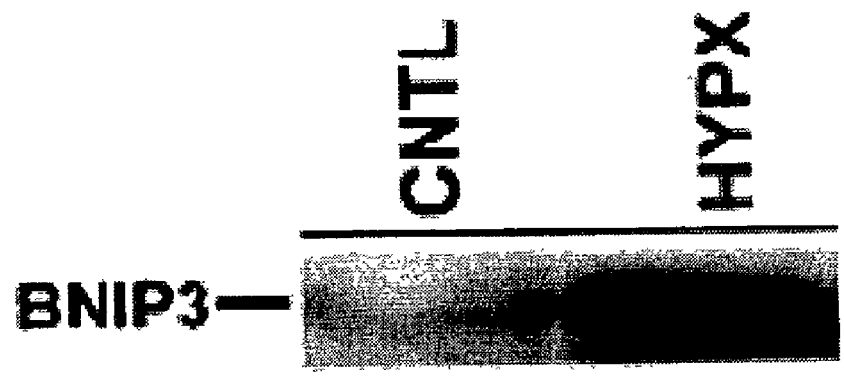
B
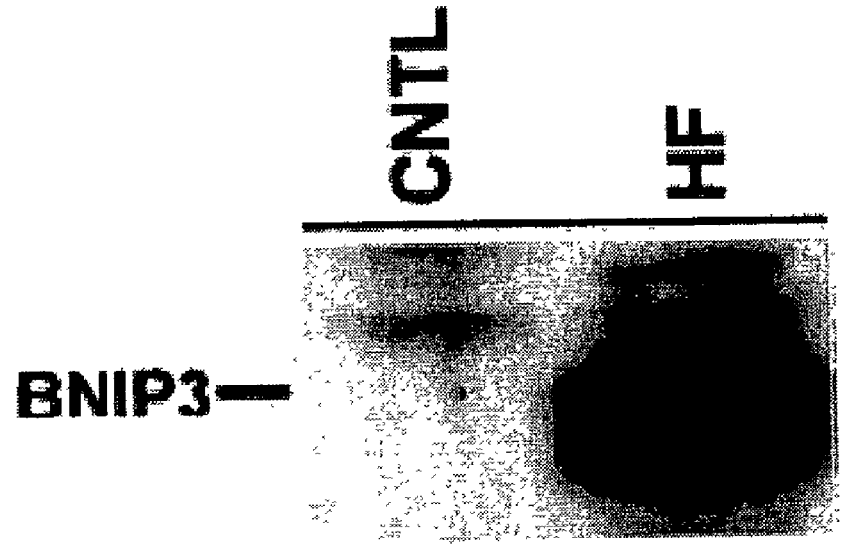

FIGURE 24
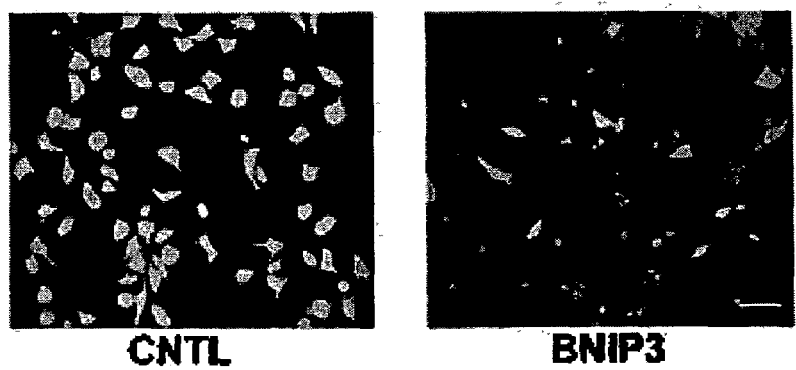
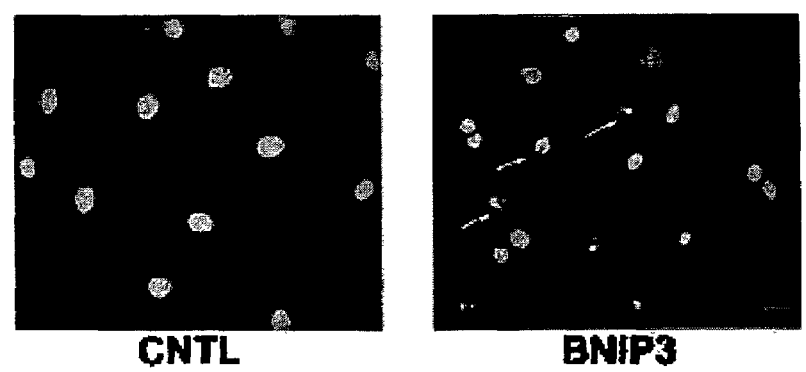
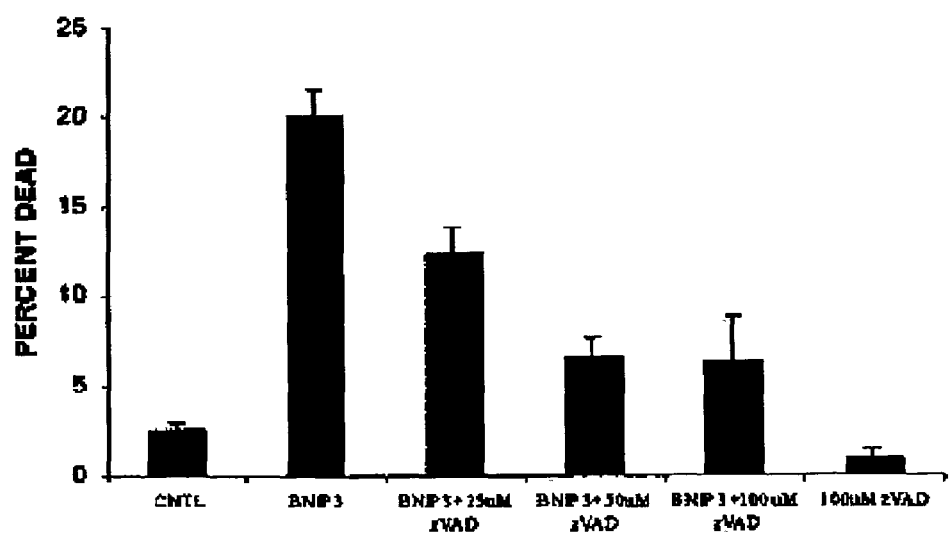

FIGURE 27
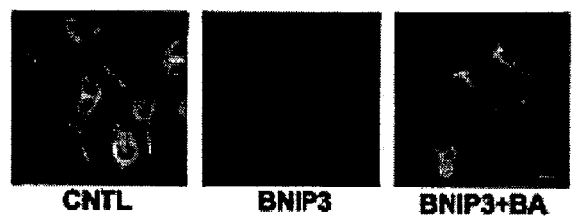
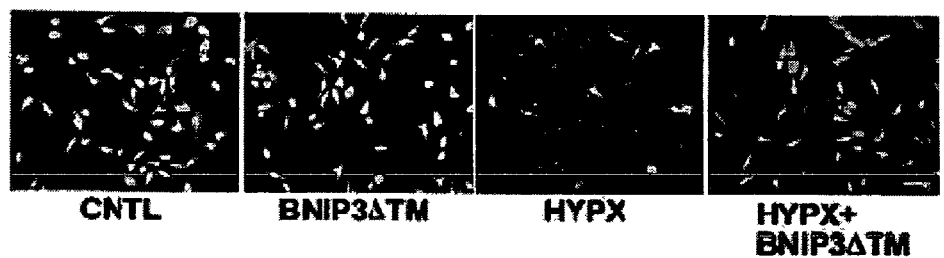
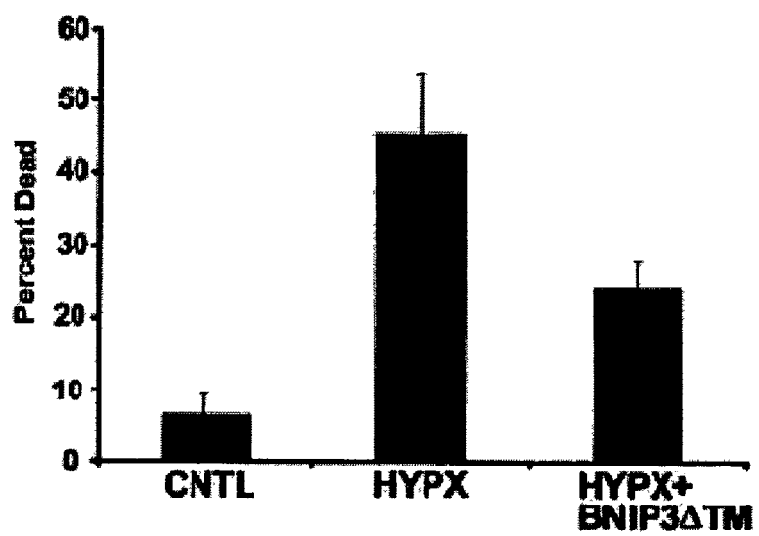

SEQUENCE LISTING

```
<160> NUMBER OF SEQ ID NOS: 18

<210> SEQ ID NO 1
<211> LENGTH: 1193
<212> TYPE: DNA
<213> ORGANISM: Artificial Sequence
<220> FEATURE:
<223> OTHER INFORMATION: BNIP3 wild type promoter

<400> SEQUENCE: 1
ctttcccgca agaccagaca cgactgtctg ggaagcagcg tttctggggc gcaccttgac      60
acttggattt ggatcaacaa tgctttcaag aagaaagact tttgatcaaa agcgggaaat     120
gagaaagcga ctttcctctg aaaagtgcct cccagtcccg aggctgcgag gccccacgc     180 caggctggct cccacggaag ccgggcaccc acccggaccg accaagcgcc actccgcccc    240
gtggacgggg cgtcccaccc cggggacgcc cgccccacac cgcgtttgca ccccggaggc    300
cccttgccgc agaggcggac ggcgcgcctc tcccgggccc ctggggtccg cgcctccctc    360
gggcagactc tttcgactct gctcgagcct ccgcttcttc ctgcgggcgg acgcccggga    420
cacaacgggc cccgctgttc acgcagggge gccccggcgg ggcgggcaaa gacccgggga    480
cgcggtcccg tcccgagacg ctcagctccg gcccaccgct cgcagctccc gccccgggcg    540
```

-continued

```
caggtcccga ccccacgggc cgtctcggag ccgcagcggc cgcttccctg cacgtcctca      600
cgccccccgc acggacgccg ccagccccgc gcctcagttt ccccactagc aggatggaaa      660
gacgggcccc gccccgaagc gtagcggcgt ctccgtggta gccagtgccc agagagtccg      720
ccggtcccac cgccccttca aggagaacc cggcccaccg cccgccgcgg cggcgaccgc       780
gcagcccact cgtcacgcgg cccgcggcgt ccagcccggg ccggctcacc tcaggcggtc      840
gctgccgccc tcgcgcctgc gcgcccctcg ccccgcccct ctcccgccc cgtcccgcg       900 caccggaggc ctctgcccct cgcccaccgc aggacccgcc ccgcgcacgc ccgcacgtg       960 ccacacgcac cccacgcccc tgcgcacgcg caggccccaa gtcgcggcca atgggcgacg     1020
cggccgcaga tccgcccggc cccgccctgc cctgtgagtt cctccggccg ggctgcgggg    1080
ctccgctcag tccgggagcg cagctgggcc gcggcgctcc gacctccgct ttcccaccgc    1140
ccgcagctga agcacatccc gcagcccggc gcggactccg atcgccgcag ttg           1193
```

<210> SEQ ID NO 2
<211> LENGTH: 1060
<212> TYPE: DNA
<213> ORGANISM: Artificial Sequence
<220> FEATURE:
<223> OTHER INFORMATION: BNIP3 D1: deletion mutant 1

<400> SEQUENCE: 2

```
tcctctgaaa agtgcctccc agtcccgagg ctgcgaggcc cccacgccag gctggctccc       60
acggaagccg ggcacccacc cggaccgacc aagcgccact ccgccccgtg acggggcgt      120 cccaccccgg ggacgccgc cccacaccgc gtttgcaccc cggaggcccc ttgccgcaga      180
ggcggacggc gcgcctctcc cgggcccctg gggtccgcgc ctccctcggg cagactcttt     240
cgactctgct cgagcctccg cttcttcctg cgggcggacg ccccggacac aacgggcccc     300
gctgttcacg caggggcgcc ccggcggggc gggcaaagac ccggggacgc ggtcccgtcc     360
cgagacgctc agctccggcc caccgctcgc agctcccgcc ccgggcgcag gtcccgaccc     420
cacgggccgt ctcggagccg cagcggccgc ttccctgcac gtcctcacgc ccccgcacg     480 gacgccgcca gccccgcgcc tcagtttccc cactagcagg atggaaagac gggccccgcc     540
ccgaagcgta gcgcgtctc cgtggtagcc agtgcccaga gagtccgccg gtcccaccgc     600
cccttcaaag gagaacccgg cccaccgccc gccgcggcgg cgaccgcgca gcccactcgt     660
cacgcggccc gcggcgtcca gcccgggccg gctcacctca ggcggtcgct gccgccctcg    720
cgcctgcgcg cccctcgccc cgccctctc ccgcccgcg tcccgcgcac cggaggcctc     780
tgcccctcgc ccaccgcagg acccgccccg cgcacgcgcc gcacgtgcca cacgcacccc    840
acgcccctgc gcacgcgcag gccccaagtc gcggccaatg ggcgacgcgg ccgcagatcc    900
gcccggcccc gccctgccct gtgagttcct ccggccgggc tgcggggctc cgctcagtcc    960
gggagcgcag ctgggccgcg gcgctccgac ctccgctttc ccaccgcccg cagctgaagc   1020
acatcccgca gccggcgcg gactccgatc gccgcagttg                           1060
```

<210> SEQ ID NO 3
<211> LENGTH: 827
<212> TYPE: DNA
<213> ORGANISM: Artificial Sequence
<220> FEATURE:
<223> OTHER INFORMATION: BNIP3 D2: deletion mutant 2

<400> SEQUENCE: 3

```
actctttcga ctctgctcga gcctccgctt cttcctgcgg gcggacgccc cggacacaac    60
gggccccgct gttcacgcag gggcgccccg gcggggcggg caaagacccg gggacgcggt   120
cccgtcccga gacgctcagc tccggcccac cgctcgcagc tcccgccccg ggcgcaggtc   180
ccgaccccac gggccgtctc ggagccgcag cggccgcttc cctgcacgtc ctcacgcccc   240
ccgcacggac gccgccagcc ccgcgcctca gtttccccac tagcaggatg aaagacggg    300
ccccgccccg aagcgtagcg gcgtctccgt ggtagccagt gcccagagag tccgccggtc   360
ccaccgcccc ttcaaaggag aacccggccc accgccccgcc gcggcggcga ccgcgcagcc   420
cactcgtcac gcggcccgcg gcgtccagcc cgggccggct cacctcaggc ggtcgctgcc   480
gccctcgcgc ctgcgcgccc ctcgccccgc ccctctcccc gcccgcgtcc cgcgcaccgg   540
aggcctctgc ccctcgccca ccgcaggacc cgccccgcgc acgcgccgca cgtgccacac   600
gcaccccacg cccctgcgca cgcgcaggcc caagtcgcg gccaatgggc gacgcggccg    660
cagatccgcc cggccccgcc ctgccctgtg agttcctccg gccgggctgc ggggctccgc   720
tcagtccggg agcgcagctg ggccgcggcg ctccgacctc cgctttccca ccgcccgcag   780
ctgaagcaca tcccgcagcc cggcgcggac tccgatcgcc gcagttg                 827
```

<210> SEQ ID NO 4
<211> LENGTH: 697
<212> TYPE: DNA
<213> ORGANISM: Artificial Sequence
<220> FEATURE:
<223> OTHER INFORMATION: BNIP3 D3: deletion mutant 3

<400> SEQUENCE: 4

```
gacgctcagc tccggcccac cgctcgcagc tcccgccccg ggcgcaggtc ccgaccccac    60
gggccgtctc ggagccgcag cggccgcttc cctgcacgtc ctcacgcccc ccgcacggac   120
gccgccagcc ccgcgcctca gtttccccac tagcaggatg aaagacggg ccccgccccg    180
aagcgtagcg gcgtctccgt ggtagccagt gcccagagag tccgccggtc ccaccgcccc   240
ttcaaaggag aacccggccc accgccccgcc gcggcggcga ccgcgcagcc cactcgtcac   300
gcggcccgcg gcgtccagcc cgggccggct cacctcaggc ggtcgctgcc gccctcgcgc   360
ctgcgcgccc ctcgccccgc ccctctcccc gcccgcgtcc cgcgcaccgg aggcctctgc   420
ccctcgccca ccgcaggacc cgccccgcgc acgcgccgca cgtgccacac gcaccccacg   480
cccctgcgca cgcgcaggcc caagtcgcg gccaatgggc gacgcggccg cagatccgcc    540
cggccccgcc ctgccctgtg agttcctccg gccgggctgc ggggctccgc tcagtccggg   600
agcgcagctg ggccgcggcg ctccgacctc cgctttccca ccgcccgcag ctgaagcaca   660
tcccgcagcc cggcgcggac tccgatcgcc gcagttg                            697
```

<210> SEQ ID NO 5
<211> LENGTH: 499
<212> TYPE: DNA
<213> ORGANISM: Artificial Sequence
<220> FEATURE:
<223> OTHER INFORMATION: BNIP3 D4: deletion mutant 4

<400> SEQUENCE: 5

```
gtggtagcca gtgcccagag agtccgccgg tcccaccgcc ccttcaaagg agaacccggc    60
ccaccgcccg ccgcggcggc gaccgcgcag cccactcgtc acgcggcccg cggcgtccag   120
cccgggccgg ctcacctcag gcggtcgctg ccgccctcgc gcctgcgcgc cctcgcccc   180
```

-continued

| | |
|---|---|
| gccctctcc ccgcccgcgt cccgcgcacc ggaggcctct gccctcgcc caccgcagga | 240 |
| cccgcccgc gcacgcgccg cacgtgccac acgcacccca cgcccctgcg cacgcgcagg | 300 |
| ccccaagtcg cggccaatgg gcgacgcggc cgcagatccg cccggccccg ccctgccctg | 360 |
| tgagttcctc cggccgggct gcggggctcc gctcagtccg ggagcgcagc tgggccgcgg | 420 |
| cgctccgacc tccgctttcc caccgcccgc agctgaagca catcccgcag cccggcgcgg | 480 |
| actccgatcg ccgcagttg | 499 |

<210> SEQ ID NO 6
<211> LENGTH: 293
<212> TYPE: DNA
<213> ORGANISM: Artificial Sequence
<220> FEATURE:
<223> OTHER INFORMATION: BNIP3 D5: deletion mutant 5

<400> SEQUENCE: 6

| | |
|---|---|
| caccggaggc tctgcccct cgccaccgc aggacccgcc ccgcgcacgc gccgcacgtg | 60 |
| ccacacgcac cccacgcccc tgcgcacgcg caggccccaa gtcgcggcca atgggcgacg | 120 |
| cggccgcaga tccgcccggc cccgccctgc cctgtgagtt cctccggccg ggctgcgggg | 180 |
| ctccgctcag tccgggagcg cagctgggcc gcggcgctcc gacctccgct ttcccaccgc | 240 |
| ccgcagctga agcacatccc gcagcccggc gcggactccg atcgccgcag ttg | 293 |

<210> SEQ ID NO 7
<211> LENGTH: 145
<212> TYPE: DNA
<213> ORGANISM: Artificial Sequence
<220> FEATURE:
<223> OTHER INFORMATION: BNIP3 D6: deletion mutant 6

<400> SEQUENCE: 7

| | |
|---|---|
| gccctgtgag ttcctccggc cgggctgcgg ggctccgctc agtccgggag cgcagctggg | 60 |
| ccgcggcgct ccgacctccg ctttcccacc gcccgcagct gaagcacatc ccgcagcccg | 120 |
| gcgcggactc cgatcgccgc agttg | 145 |

<210> SEQ ID NO 8
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 8

| | |
|---|---|
| cgccttccaa tgtagatccc c | 21 |

<210> SEQ ID NO 9
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 9

| | |
|---|---|
| ccccctttct tcataacgct t | 21 |

<210> SEQ ID NO 10
<211> LENGTH: 20
<212> TYPE: DNA
<213> ORGANISM: Artificial Sequence
<220> FEATURE:
<223> OTHER INFORMATION: antisense oligonucleotide -continued

```
<400> SEQUENCE: 10
gctgtgcgct cgggtgtta                                                    20

<210> SEQ ID NO 11
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 11
cgctgctccc attcccattg c                                                 21

<210> SEQ ID NO 12
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 12
cccgctctgc gacatggtgg c                                                 21

<210> SEQ ID NO 13
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 13
gacatggtgg ctccgcaaag g                                                 21

<210> SEQ ID NO 14
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 14
cgcaaaggag ccggagccca a                                                 21

<210> SEQ ID NO 15
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 15
cgacaggcct gggaagtgac c                                                 21

<210> SEQ ID NO 16
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 16
tgcagacacc caaggatcat g                                                 21
```

-continued

```
<210> SEQ ID NO 17
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 17
ggtaatggtg gacagcaagg c                                            21

<210> SEQ ID NO 18
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 18
tgcagacacc caaggatcat g                                            21
```

NIP3 FAMILY OF PROTEINS

RELATED APPLICATIONS

The present application is a continuation-in-part of PCT/US01/21043 filed Jun. 29, 2001 designating the United States and which claims the benefit of priority under 35 USC §119(e) to U.S. provisional application No. 60/215,643 filed Jun. 30, 2000 (now abandoned) and U.S. provisional application No. 60/219,554 filed Jul. 20, 2000 (now abandoned). The application also claims the benefit of priority under 35 USC §119(e) to U.S. provisional application No. 60/348,135 filed Nov. 9, 2001 and U.S. provisional application No. 60/344,196 filed Dec. 28, 2001. The contents of all of the related applications are incorporated herein by reference.

FIELD OF THE INVENTION

The present invention relates to methods and compositions for modulating necrosis and for treating neurological and cardiovascular diseases.

BACKGROUND OF THE INVENTION

Cell death is an important aspect during the embryonic or post-natal development of major organ systems. Apoptosis, or programmed cell demise, also plays a critical role in maintaining homeostasis in many adult tissues. Within vertebrates, bcl-2 is the best understood gene in a cell death pathway and functions as a cell death repressor.

Apoptosis is a term used to refer to the process(es) of programmed cell death and has been described in several cell types (Waring et al. (1991) *Med. Res. Rev.* 11: 219; Williams G. T. (1991) *Cell* 65: 1097; Williams G. T. (1992) *Trends Cell Biol.* 2: 263; Yonisch-Rouach et al. (1991) *Nature* 352: 345). Apoptosis is likely involved in controlling the amount of and distribution of certain differentiated cell types, such as lymphocytes and other cells of the hematopoietic lineage. The mechanism(s) by which apoptosis is produced in cells is incompletely understood, as are the regulatory pathways by which the induction of apoptosis occurs.

Apoptosis was first described as a morphologic pattern of cell death characterized by cell shrinkage, membrane blebbing and chromatin condensation culminating in cell fragmentation (Kerr et al., 1992). One hallmark pattern early in the process of cell death is internucleosomal DNA cleavage (Wyllie, 1980). The death-sparing effects of interrupting RNA and protein synthesis and the stereotyped patterns of cell death during development were consistent with a cell autonomous genetic program for cell death (Wyllie et al. (1980) *Int. Rev. Cytol.* 68: 251; Sulston, J. and Horvitz, H. (1977) *Develop. Biol.* 56: 110; Abrams et al. (1993) *Development* 117: 29). The isolation of mutants defective for development cell death in the nematode Caenorhabditis elegans supported this view (Ellis, H. and Horvitz, H. (1986) *Cell* 44: 817; Hengartner et al. (1992) *Nature* 365: 494).

The consistency of the morphologic and biochemical patterns defined as apoptosis within different cell types and species, during normal development and as a response to external stimuli are consistent with a common cause of cellular mortality. This thesis is supported by the concept of an endogenous program responsible for cell death and the presence of gene products which are positive and negative regulators of apoptosis. The best studied negative regulator of apoptosis is the bcl-2 proto-oncogene product. It provides the strongest evidence for a shared mammalian pathway of death by its ability to block a wide variety of cell death models.

This pattern of morphologic cell death is characterized by a dramatic plasma membrane blebbing, cell volume contraction, nuclear pyknosis, and internucleosomal DNA degradation following the activation of an endonuclease. Over expression of mitochondrial bcl-2 appears to function as an antidote to this process and has the unique function of blocking programmed cell death independent of promoting proliferation.

The maintenance of homeostasis in normal tissue, in many respects, reflects a simple balanced equation of input (cellular proliferation and renewal) versus output (cell death). This is most easily envisioned for encapsulated organs, such as the prostate, but is also true of the recirculating hematopoietic lineages. The maintenance of remarkably invariant cell numbers reflects tightly regulated death pathways as well as controlled proliferation. See for example S. J. Korsmeyer "bcl-2 Initiates a New Category of Oncogenes: Regulators of Cell Death", *Blood* Vol. 80 No. 4 pp. 879-886, Aug. 15, 1992.

Programmed cell death represents a cell autonomous suicide pathway that helps restrict cell numbers. The well-defined loss of specific cells is crucial during embryonic development as part of organogenesis. In the mature tissues, genetically programmed demise regulates the volume of cells. A morphologically distinct and temporally regulated cell death entitled apoptosis has been identified by Wyllie A. H.: "Apoptosis: Cell death in tissue regulation". *J. Pathol* 153: 313, 1987. Cells dying by apoptosis display marked plasma membrane blebbing, volume contraction, nuclear condensation, and the activation of an endonuclease that cleaves DNA into nucleosomal length fragments.

The genetic regulation of cell death is thought to be a central mechanism of cellular homeostasis and development (Bernardi, P. et al, 1999, Bossy-Wetzel, E. et al, 1998, Boyd, J. M. et al, 1994, Chautan, M. et al, 1999). The Bcl-2 family of genes (Bernardi, P. et al, 1999, Chen, G. et al, 1999), which are related to ced-9 of *C. elegans* (Chen, G. et al, 1997), were originally identified as repressors of cell death. It is known that both pro-and anti-apoptotic Bcl-2 homologs exist, however their exact biochemical function has not been determined. Recent studies suggest that Ced-9 and Bcl-2/BCl-$X_L$ may physically interact with proteins that are required for the execution of apoptosis, Ced-3 and Ced-4 (Chi, S. et al, 1999, Crompton, M. 1999, Datta, S. R. et al, 1997), however these proteins have not been isolated and purified. Ced-3 is a protease which in mammals is represented by a large family of cysteine proteases which cleave after aspartic acid, now called caspases (Chautan, M. et al, 1999, Deas, O. et al, 1998). In mammalian cells overexpression of bcl-2 prevents the processing and activation of caspase-3 (CPP32) (Earnshaw, W. C. et al, 1999, Finucane, D. M. et al, 1999).

Bcl-2 family members bear C-terminal transmembrane domains that allow their association with the outer mitochondrial membrane (Goping, 1. S. et al, 1998) and this mitochondrial localization is important for the suppressive function of Bcl-2 (Green, D. R. et al, 1998, Griffiths, G. J. et al, 1999). There is growing evidence that mitochondrial function is disturbed early in the apoptotic response and may be important in mediating apoptosis (Gross, A. et al, 1999, Hakem, R. et al, 1998, Harada, H. et al, 1999). This is often seen as the loss of mitochondrial membrane potential (Gross, A. et al, 1999, Hakem, R. et al, 1998) and the release of cytochrome c (Harada, H. et al, 1999), and cytochrome c has been implicated in the activation of caspase (Harada, H. et al, 1999, Horvitz, H. R. 1999, Imazu, T. et al, 1999). Bcl-2 can suppress the release of cytochrome c from mitochondria and prevent caspase activation (Horvitz, H. R. 1999, Imazu, T. et al, 1999).

Additionally, the protein encoded by the bcl-2 proto-oncogene has been reported to be capable of inhibiting apoptosis in many hematopoietic cell systems. The proto-oncogene bcl-2 was isolated and characterized as a result of its frequent translocation adjacent to the immunoglobulin heavy chain enhancer in the t (Green, D. R. et al, 1998; Harada, H. et al, 1999) chromosome translocation present in more than 80% of human follicular lymphomas (Chen-Levy et al. (1989) Mol. Cell. Biol. 9: 701; Clearly et al. (1986) Cell 47: 19). These neoplasias are characterized by an accumulation of mature resting B cells presumed to result from a block of apoptosis which would normally cause turnover of these cells. Transgenic mice expressing bcl-2 under the control of the Eu. enhancer similarly develop follicular lymphomas which have a high incidence of developing into malignant lymphomas (Hockenbery et al. (1990) Nature 348: 334; McDonnell T. J. and Korsmeyer S. J. (1991) Nature 349: 254; Strasser et al. (1991) Cell 67: 889).

The capacity of bcl-2 to enhance cell survival is related to its ability to inhibit apoptosis initiated by several factors, such as cytokine deprivation, radiation exposure, glucocorticoid treatment, and administration of anti-CD-3 antibody (Nunez et al. (1990) op. cit; Hockenbery et al. (1990) op. cit; Vaux et al. (1988) op. cit; Alnemri et al. (1992) Cancer Res. 52: 491; Sentman et al. (1991) Cell 67: 879; Strasser et al. (1991) op. cit). Upregulation of bcl-2 expression also inhibits apoptosis of EBV infected B-cell lines (Henderson et al. (1991) Cell 65: 1107). The expression of bcl-2 has also been shown to block apoptosis resulting from expression of the positive cell growth regulatory proto-oncogene, c-myc, in the absence of serum or growth factors (Wagner et al. (1993) Mol. Cell. Biol. 13: 2432). However, the precise mechanism (s) by which bci-2 is able to inhibit apoptosis is not yet fully defined.

The bcl-2 proto-oncogene is rather unique among cellular genes in its ability to block apoptotic deaths in multiple contexts (Korsmeyer, S. (1992) *Blood* 80: 879). Overexpression of bcl-2 in transgenic models leads to accumulation of cells due to evasion of normal cell death mechanisms (McDonnell et al. (1989) *Cell* 57: 79). Induction of apoptosis by diverse stimuli, such as radiation, hyperthermia, growth factor withdrawal, glucocorticoids and multiple classes of chemotherapeutic agents is inhibited by bcl-2 in vitro models (Vaux et al. (1988) *Nature* 335: 440; Tsujimoto, Y. (1989) *Oncogene* 4: 1331; Nunez et al. (1990) *J. Immunol.* 144: 3602; Hockenbery et al. (1990) *Nature* 348: 334; Sentman et al. (1991) *Cell* 67: 879; Walton et al. (1993) *Cancer Res.* 53: 1853; Miyashita, T. and Reed, J. (1993) *Blood* 81: 151). These effects are proportional to the level of bcl-2 expression. Additionally, the endogenous pattern of bc1-2 expression is highly suggestive of a role in the regulation of cell survival in vivo (Hockenbery et al. (1991) *Proc. Natl. Acad. Sci. USA* 88: 6961; LeBrun et al. (1993) *Am. J. Pathol.* 142: 743). The bcl-2 protein seems likely to function as an antagonist of a central mechanism operative in cell death.

Additionally, Kerr et al. (Kerr, J. F. R. et al, 1972), on the basis of distinct morphological criteria, identified apoptosis as a programmed and intrinsic cell death pathway, in contrast to necrosis, which was viewed as a passive response to injury. It is now clear that apoptosis is a highly regulated genetic program that is evolutionarily conserved in multicellular organisms and is essential for development and tissue homeostasis (Horvitz, H. R. 1999, 57). The genetic program results in the activation of cysteine aspartyl proteases (caspases) that cleave nuclear and cytoplasmic substrates and disassemble the cell (Earnshaw, W. C. et al, 1999, 54), yielding the characteristic morphological features such as chromatin condensation, DNA fragmentation, plasma membrane blebbing, and the formation of apoptotic bodies (Xue, L. Z., et al., 1999). In contrast to apoptosis, necrosis is considered an unregulated process occurring in response to toxicants and physical injury. This form of cell death is morphologically characterized by extensive mitochondrial swelling, cytoplasmic vacuolation, and early plasma membrane permeability without major nuclear damage (Kerr, J. F. R. et al, 1972, Kitanaka, C. et al, 1999, 55).

Mitochondria appear to play a central role in the induction of cell death. This is thought to occur by at least three possible mechanisms: (i) release of apoptogenic proteins that facilitate caspase activation, (ii) disruption of electron transport, oxidative phosphorylation, and ATP production that can result in an energetic catastrophe, and (iii) alteration of the redox potential, resulting in increased cellular oxidative stress (Green, D. R. et al, 1998). The main biochemical determinant of apoptosis is the activation of caspases, and this is in part regulated by mitochondria. All caspases are synthesized as an inactive polypeptide (zymogen) that must be proteolytically processed to form an active tetramer (Earnshaw, W. C. et al, 1999). Recent work proposes that this processing is initiated through autocatalytic activation. For example, the caspase 8 zymogen is aggregated for autoprocessing by ligand-induced clustering of trimeric death receptors such as CD95/Fas (Srinivasula, S. M., et al., 1998). Active caspase 8 cleaves the proapoptotic BCL-2 family member BID, which is then able to translocate to mitochondria (Li, H. et al, 1998, Luo, X. et al, 1998). BID, as well as many other apoptotic signals, induces mitochondria to release cytochrome c, which functions as a cofactor with dATP for Apaf-1 binding and activation of caspase 9 and downstream effector caspases (Li, P. et al, 1997, 51). Another less well studied mitochondrial apoptogenic protein is apoptosis-inducing factor (AIF), a flavoprotein released in response to apoptotic signals that translocates to the nucleus to induce DNA fragmentation and chromatin condensation in a caspase-independent manner (Tsujimoto, Y. 1997).

Apoptotic cell death signals induce other mitochondrial changes, such as opening of the permeability transition (PT) pore, a putative highly regulated ion channel located at the contact sites between the inner and outer mitochondrial membrane (Crompton, M. 1999). The PT pore is a large protein complex, primarily composed of the adenine nucleotide transporter (ANT), cyclophilin D, and voltage dependent anion channel (VDAC [also called porin]), that can interact with several other proteins (Crompton, M. 1999, Kroemer, G. et al, 1998). When the PT pore is in the open state, it permits the passage of solutes of; 1,500 Da and results in depolarization of mitochondria, which consequently decreases the measured proton electrochemical gradient (Dcm). This, in turn, can lead to the inhibition of respiration, generation of reactive oxygen species (ROS), and loss of ATP production (Bernardi, P. et al, 1999, Crompton, M. 1999). PT pore opening also increases the permeability of certain ions across the mitochondrial membrane, resulting in increased water influx into the matrix and consequent large-amplitude mitochondrial swelling (Gross, A. et al, 1999, Lemasters, J. J. et al, 1998).

The biochemical determinants of necrotic cell death are less well defined, but similar to apoptosis. It has been suggested that the PT pore might play a major role in necrosis. PT pore opening has been described in response to a rise in cytosolic free Ca 21, anoxia, and reperfusion oxidative stress with overproduction of ROS in cardiac myocytes (Crompton, M. 1999). Although both apoptosis and necrosis are associated with PT pore opening, necrosis is distinguished by an early loss of plasma membrane integrity and ATP, whereas both are maintained and ATP production is required for apoptosis (Leist, M. et al, 1997, Nicotera, P. et al, 1998).

In 1996 Dr. A. H. Greenberg's lab, isolated a protein called BNIP3 and soon thereafter determined that a homodimeric complex of BNIP3 was associated with the energy producing organelle of the cell, the mitochondria, and that BNIP3 had a function in cell death (Chen G et al, 1997). Along with human BNIP3, other family members NIX and NOX (NINA) were identified, as were homologues from other species namely mouse and *c. elegans* (Chen G et al, 1999; Cizeau J et al, 2000). Initially it was believed that BNIP3 in apoptosis; however, subsequent work on the biological mechanism of BNIP3 revealed that this was inaccurate (Vande Velde C et al, 2000).

It would therefore be useful to determine the role BNIP3 plays in cell death. It would also be useful to develop methods of using BNIP3 to treat diseases.

SUMMARY OF THE INVENTION

The present inventors have determined that BNIP3 induces a necrosis-like cell death that is mediated through permeability transition (PT) pore opening and mitochondrial dysfunction.

Accordingly, the present invention provides a method of modulating cell necrosis comprising administering an effective amount of an agent that can modulate a BNIP3 gene or protein to a cell or animal in need thereof.

In one embodiment, the present invention provides a method of inhibiting cell necrosis comprising administering an effective amount of an agent that can inhibit BNIP3 to a cell or animal in need thereof. Inhibiting cell necrosis can be useful in treating a variety of conditions including neurological and cardiovascular diseases.

In another embodiment, the present invention provides a method of inducing cell necrosis comprising administering an effective amount of an agent that can augment or enhance BNIP3 expression to a cell or animal in need thereof. Inducing cell necrosis can be useful in treating cancer.

In a further embodiment, the invention provides a method of treating a neurological disease comprising administering an effective amount of an agent that can inhibit BNIP3 to a cell or animal in need thereof.

In yet another embodiment, the present invention provides a method of treating a cardiovascular disease comprising administering an effective amount of an agent that can inhibit BNIP3 to a cell or animal in need thereof.

The present invention also includes screening assays for isolating BNIP3 modulators including agents that inhibit as well as agents that activate BNIP3.

The present invention further includes pharmaceutical compositions for carrying out any of the above methods of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A through C are photographs showing BNIP3 expression and integration into mitochondrial membranes;

FIGS. 2A and B are graphs showing that the broad spectrum caspase inhibitors Ac-zVAD-FMK and baculovirus p35 failed to inhibit BNIP3 induced cell deaths;

FIGS. 3A and B are graphs showing that BNIP3 does not activate caspases;

FIGS. 5A and B are graphs showing BNIP3 induced cell death in the absence of a PAF-1, caspase-9, or caspase-3;

FIGS. 6A and B are graphs showing that BNIP3 induces rapid plasma membrane permeability but not PE externalization;

FIGS. 7A and B are graphs showing BNIP3 induced cell death is characterized by late DNA fragmentation;

FIGS. 9A through E are photos and graphs showing that BNIP3 induced cell death is characterized by mitochondrial dysfunction;

FIGS. 10A through E show the inhibition of BNIP3 induced mitochondrial dysfunction cell death by PT inhibitors;

FIG. 17 shows that glutamate increased BNIP3 expression. A. Glutamate increased neuronal cell death in a dose-dependent manner. B. Expression of BNIP3 was not detectable immunohistochemically in the majority of untreated neurons; less than 15% of untreated neurons expressed low levels of BNIP3. C. More than 50% of cells treated with 100 μM glutamate for 6 hours stained positively for BNIP3. D. Nuclei in BNIP3 positive neurons showed a dysmorphic appearance atypical of cell death.

FIG. 18 shows that BNIP3 expression caused neuronal cell death. A. Transient transfection of rat hippocampal neurons resulted in DNA condensation and neuronal cell death. B. Transient transfection of rat hippocampal neurons with a dominant-negative form of BNIP3 (BNIP$^{3-163}$) did not cause DNA condensation or localization of BNIP3 to mitochondria; BNIP3 was diffusely distributed in the cytoplasm. C. Neuronal survival rates after 5 days of transfection with BNIP3. D. 85% of BNIP3-positive neurons in BNIP3-transfected cells showed DNA condensation compared to 17% in BNIP$^{3-163}$ transfected cells. E. Glutamate significantly decreased neuronal survival. BNIP3 transfection decreased significantly ($P<0.05$) neuronal survival following glutamate exposure. BNIP3-163 transfection protected significantly neuronal cell death induced by glutamate ($p<0.001$).

FIG. 23 shows the induction of BNIP3 in adult myocardium. A. Western blot analysis of cardiac cell lysate from ex vivo perfused Langendorff-adult rat hearts under normoxic conditions and global hypoxia for 1 hour. B. Western blot analysis of cardiac cell lysate derived from normal non-failing adult hearts (CNTL) and adult rat hearts with chronic heart failure (HF) after 8 weeks of myocardial infarction.

FIG. 24 shows that BNIP3 provokes widespread cell death of ventricular myocytes. A. Immunofluorescent staining of ventricular myocytes in the presence and absence of BNIP3. Cell viability was determined using the vital dyes calcein acetoxymethyl ester (green) and ethidium homodimer-1 (red) to distinguish the number of live versus dead cells, respectively. Compared with cells infected with a control adenovirus (AdCMV), BNIP3 provoked widespread cell death as indicated by the number of red staining myocytes. Bar=100 μm. B. Immunofluorescence images of myocytes stained for nuclear morphology by Hoechst 33258 staining (blue). CNTL indicates control cells; BNIP3, myocytes infected with adenovirus encoding BNIP3; and Arrows, apoptotic nuclei. Bar=10 μm. C. BNIP3-induced cell death of ventricular myocytes was suppressed by pan caspase inhibitor z-VADfmk in a dose-dependent manner (25 to 100 μmol/L). Cell viability was assessed as described for A. Data were obtained from at least n=3 independent myocyte isolations, counting at least ≧200 cells per condition.

FIG. 27 shows that BNIP3 induces perturbations to mitochondria. A. Mitochondrial permeability transition pore (PT) was monitored in ventricular myocytes using the membrane permeable dye calcein-AM in the presence of cobalt chloride to quench the cytoplasmic signal. Onset of PT is marked by a loss in green fluorescence from mitochondria. CNTL indicates normoxic control myocytes; BNIP3, myocytes infected with an adenovirus encoding BNIP3; BNIP3+BA, myocytes infected with an adenovirus encoding BNIP3 in the presence of Bongkrekic acid (50 μmol/L). B. Cell viability was determined as described for FIG. 24. CNTL indicates normoxic control cells; HYPX, cells subjected to hypoxia; HYPX+BNIP3ΔTM, cells subjected to hypoxia in the presence of BNIP3ΔTM. Bar=100 μm. C. Histogram of data shown in B. Data were obtained from at least n=3 independent myocyte isolations, counting at least ≧200 cells per condition.

DETAILED DESCRIPTION OF THE INVENTION

I. Therapeutic Methods (a) Modulating Necrosis

Figures 1B, 1C:
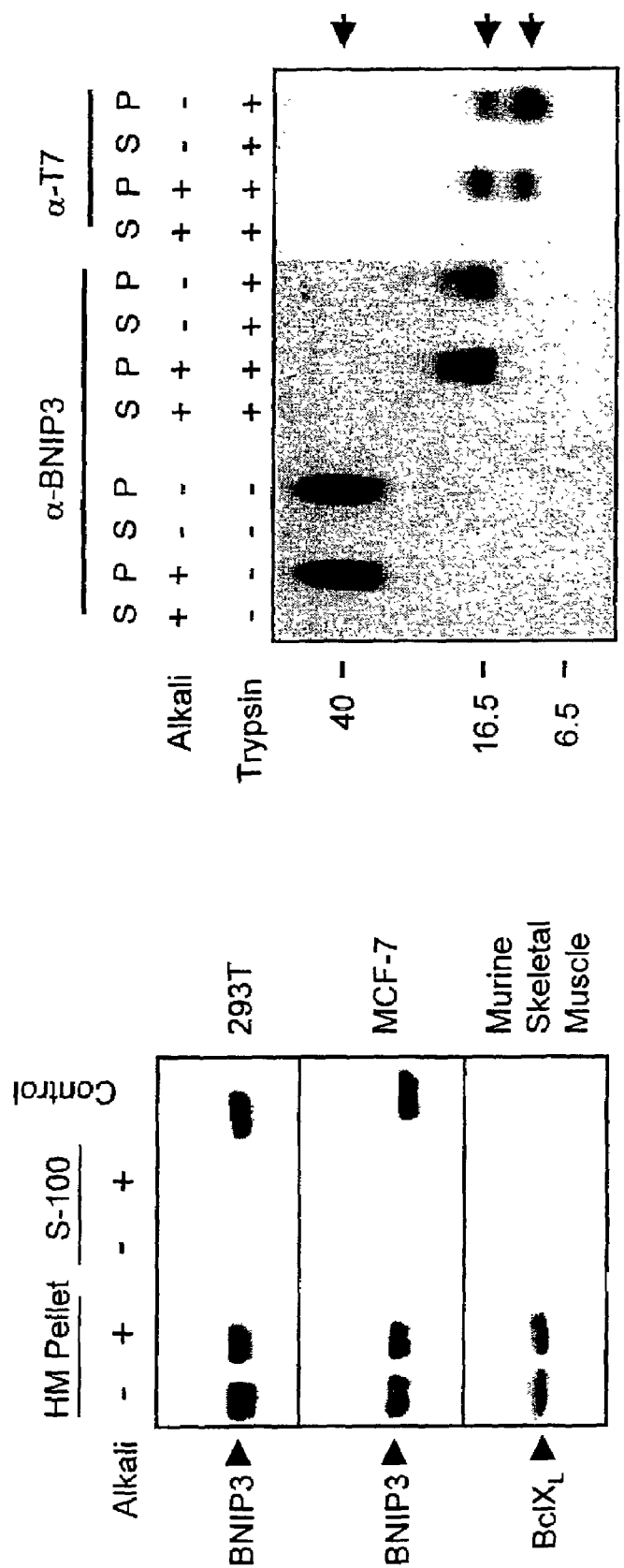

The present inventors have shown that, in certain instances, BNIP3-mediated cell death is independent of Apaf-1, caspase activation, cytochrome c release, and nuclear translocation of apoptosis-inducing factor. Cells transfected with BNIP3 exhibit early plasma membrane permeability, mitochondrial damage, extensive cytoplasmic vacuolation, and mitochondrial autophagy, yielding a morphotype that is typical of necrosis. These changes were accompanied by rapid and profound mitochondrial dysfunction characterized by opening of the mitochondrial PT pore, proton electrochemical gradient (Dcm) suppression, and increased reactive oxygen species production. The PT pore inhibitors cyclosporin A and bongkrekic acid blocked mitochondrial dysregulation and cell death. BNIP3 is a gene that mediates a necrosis-like cell death through PT pore opening and mitochondrial dysfunction.

Accordingly, the present invention provides a method of modulating cell necrosis comprising administering an effective amount of an agent that can modulate a BNIP3 gene or protein to a cell or animal in need thereof.

The term "modulate" as used herein includes the inhibition or suppression of a function or activity as well as the induction or enhancement of the function or activity. For example, modulating necrosis includes inhibiting and inducing necrosis. Agents that can modulate a BNIP3 gene or protein includes agents that can inhibit the expression of the gene or the activity of the protein as well as agents that can induce the expression of the gene or enhance the activity of the protein.

The term "necrosis" as used herein means a caspase-independent cell death which is mediated through the opening of the PT pore. The term includes genetically regulated or programmed necrosis.

The term "a cell" as used herein includes a single cell as well as a plurality of population of cells. Administering an agent to a cell includes both in vitro and in vivo administration.

The term "animal" as used herein includes all members of the animal kingdom including humans. Preferably, the animal to be treated is a human.

The term "effective amount" as used herein means an amount effective at dosages and for periods of time necessary to achieve the desired results (e.g. to modulate necrosis).

In one aspect, the present invention provides a method of inhibiting cell necrosis comprising administering an effective amount of an agent that can inhibit BNIP3 to a cell or animal in need thereof.

The term "inhibiting cell necrosis" means that the level of necrosis in the cells in the presence of the agent is decreased as compared to the level of necrosis observed in the absence of the agent. Necrosis can be assessed using a variety of techniques known in the art including the methods as described in the Examples.

The term "an agent that can inhibit BNIP3" means any molecule or compound that can inhibit the expression of the BNIP3 gene or can inhibit the activity of the BNIP3 protein. For example, the agent may be an antisense oligonucleotide that inhibits the expression of the BNIP3 gene or an antibody that inhibits the function of the BNIP3 protein. The agent may also be a competitive inhibitor of the BNIP3 protein such as a BNIP3 deletion mutant or peptide mimetic. In addition, the inhibitor may be an agent that can interfere with the association of BNIP3 with the mitochondrial membrane which is required for its necrotic ability or can block the PT pore opening which would also prevent necrosis. Agents that can inhibit BNIP3 are described in greater detail in Section II.

The method of the invention for inhibiting cell necrosis can be used to treat any condition wherein it is desirable to prevent cell death through necrosis. As used herein, and as well understood in the art, "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

There are various clinical conditions recognized where necrotic cell death has been identified. Examples of this are cardiac cell death caused by hypoxia during heart attacks or neuronal cell death caused by trauma to the brain. Both of these clinical conditions have been shown to involve an increased expression and tight mitochondrial association of BNIP3. Therefore by preventing BNIP3 action through a decrease in its expression or tight mitochondrial association, it is possible to limit cardiac damage during heart attacks as well as neuronal damage cause by brain trauma. Both of these indications are further described below. Inhibiting BNIP3 may also be useful in protecting normal cells or bone marrow during chemotherapy or immunotherapy.

In another embodiment, the present invention provides a method of inducing cell necrosis comprising administering an effective amount of an agent that can induce BNIP3 to a cell or animal in need thereof.

The term "inducing cell necrosis" means that the level of necrosis in the cells in the presence of the agent is increased as compared to the level of necrosis observed in the absence of the agent. Necrosis can be assessed using a variety of techniques known in the art including the methods as described in the Examples.

The term "agent that can induce BNIP3" means any molecule or compound that can induce or increase the expression of the BNIP3 gene or induce or enhance the activity of the BNIP3 protein. Administering an agent that can induce BNIP3 includes administering a nucleic acid molecule that encodes BNIP3 as well as administering the BNIP3 protein. In addition, BNIP3 activity may be enhanced by increasing the association of BNIP3 with the mitochondrial membrane. Agents that induce BNIP3 are described in greater detail in Section II.

The method of inducing necrosis can be used in any situation where one wishes to target cells for elimination. In one embodiment, the present invention provides a method of inducing necrosis in a cancer cell comprising administering an effective amount of an agent that can induce BNIP3 to a cell or animal in need thereof. The cancer cell can be any type, including but not limited to, cardiovascular and cardiac cancers, neurological cancers (including brain tumors), leukemias, lymphomas, myelomas, sarcomas, carcinomas, melanomas, adenomas, rhadomyosarcoma tumors (skeletal tumors) and genitourinary cancers.

Enhancing BNIP3 function may also be important in the treatment of certain genetic disorders. Since regulated cell death is critical in embryonic development, any disruption of cell death pathways results in genetic defects. Through the characterization of regulated necrosis involving BNIP3, it is now possible that certain genetic dysfunctions can be traced back to a defect in this regulated necrotic pathway. By compensating for this loss of BNIP3 function, it is possible to overcome the genetic anomaly.

One may also want to induce BNIP3 in stem cells to modulate neurogenesis and cardiogenesis; in HIV induced neural and cardiac diseases; in coxsachie virus; and in artherosclerosis of the coronary vessels and the cerebral vessels.

(b) Neurological Diseases

Excitotoxicity is a form of neuronal cell death that has been associated with a variety of neurodegenerative disorders including stroke, Alzheimer's disease, Parkinson's disease, and spinal cord and traumatic brain injury. The inventors have shown for the first time that BNIP3 levels are increased dramatically in in vivo and in vitro models of excitotoxicity, that overexpression of full length BNIP3 decreased the viability of hippocampal neurons grown in culture and increased significantly the susceptibility of these neurons to glutamate-induced cell death, that BNIP3-mediated cell death occurred independently of caspase activation, and that expression of a truncated (dominant negative) form of BNIP3 that lacked the functional transmembrane domain increased neuronal viability and protected neurons against glutamate-induced excitotoxicity. As a result, modulating BNIP3 can be useful in modulating neural cell death. In particular, it would be useful to inhibit BNIP3 expression or activity to prevent neural cell death in neurological diseases.

Accordingly, the present invention provides a method of preventing or inhibiting the death of a neural cell comprising administering an effective amount of an agent that can inhibit BNIP3 to a cell or animal in need thereof. Agents that can inhibit BNIP3 are described above in Section I (a) and below in Section II.

The term "neural cell" includes, but is not limited to, neurons, astrocytes, glial cells and peripheral schwann cells.

The present invention also provides a method of treating a neurological disease comprising administering an effective amount of an agent that can inhibit BNIP3 to a cell or animal in need thereof.

Neurological diseases that can treated by the present invention include, but are not limited to, acute and chronic neurological disorders such as traumatic brain injury, ischemic and hemorrhagic stroke, Alzheimer's disease, Huntington's disease, amyotropic lateral sclerosis (ALS), multiple sclerosis, neuro AIDS, Parkinson's disease, Pick's disease, epilepsy, excitotoxicity, genetic disorders, inborn errors of metabolism, and neurogenesis. BNIP3 may also be modulated in neural derived stem cells and used in the treatment of neurological diseases.

(c) Cardiovascular diseases

The inventors have shown that BNIP3 is a key regulator of mitochondrial function and cell death of ventricular myocytes during hypoxia. In contrast to normoxic cells, a 5.6-fold increase ($P<0.05$) in myocyte death was observed in cells subjected to hypoxia. Moreover, a significant increase in BNIP3 expression was detected in postnatal ventricular myocytes and adult rat hearts subjected to hypoxia. An increase in BNIP3 expression was detected in adult rat hearts in vivo with chronic heart failure. Subcellular fractionation experiments indicated that endogenous BNIP3 was integrated into the mitochondrial membranes during hypoxia. Adenovirus-mediated delivery of full-length BNIP3 to myocytes was toxic and provoked an 8.3-fold increase ($P<0.05$) in myocyte death with features typical of apoptosis. Mitochondrial defects consistent with opening of the permeability transition pore (PT pore) were observed in cells expressing BNIP3 but not in cells expressing BNIP3 missing the carboxyl-terminal transmembrane domain (BNIP3ΔTM), necessary for mitochondrial insertion. The pan-caspase inhibitor z-VAD-fmk (25 to 100 μmol/L) suppressed BNIP3-induced cell death of ventricular myocytes in a dose-dependent manner. Bongkrekic acid (50 μmol/L), an inhibitor of the PT pore, prevented BNIP3-induced mitochondrial defects and cell death. Expression of BNIP3ΔTM suppressed the hypoxia-induced integration of the endogenous BNIP3 protein and cell death of ventricular myocytes. To the inventors' knowledge, the data provide the first evidence for the involvement of BNIP3 as an inducible factor that provokes mitochondrial defects and cell death of ventricular myocytes during hypoxia. As a result, modulating BNIP3 can be useful in modulating cardiac cell death. In particular, it would be useful to inhibit BNIP3 expression or activity to prevent cardiac cell death in cardiovascular diseases.

Accordingly, the present invention provides a method of preventing or inhibiting the death of a cardiovascular cell comprising administering an effective amount of an agent that can inhibit BNIP3 to a cell or animal in need thereof.

Preferably, the cardiovascular cell is under hypoxic conditions. Accordingly, the present invention also provides a method of inhibiting hypoxia-induced cell death comprising administering an effective amount of an agent that can inhibit BNIP3 to a cell or animal in need thereof.

Agents that can inhibit BNIP3 are described above in Section I (a) and below in Section II.

The term "cardiovascular cell" includes, but is not limited to, cardiac myocytes, ventricular myocytes, atrial myocytes, cardiac stem cells, endothelial cells, vascular smooth muscle cells, pacemakers cells, myofibroblasts and fibroblasts.

The present invention also provides a method of treating a cardiovascular disease comprising administering an effective amount of an agent that can inhibit BNIP3 to a cell or animal in need thereof.

Cardiovascular diseases which may be treated by the present invention include, but are not limited to, acute and chronic cardiac conditions such as, cardiac hypoxia, cardiac hypoxia-reoxygenation, cardiac ischemia-reperfusion injury, ischemic heart disease, heart failure (including congestive heart failure), heart hypertrophy (all stages), by-pass surgery, coronary angioplarty, vascular defects (atherosclerosis), congenital heart (defects) disease, and cardiac cell muscle regeneration and chemotherapeutic induced cardiomyopathy. BNIP3 may also be modulated in cardiac derived stem cells and used in the treatment of cardiovascular diseases.

II. Agents that Modulate BNIP3

The present invention includes the use of any and all agents that modulate BNIP3 in the methods of the invention. The agent can be any type of substance, including, but not limited to, nucleic acids (including antisense oligonucleotides), proteins (including antibodies), peptides, peptide mimetics, carbohydrates, small molecules (including organic and inorganic compounds). In particular, the agent can be BNIP3, BNIP3 agonists, BNIP3 antagonists and agents that inhibit BNIP3 agonists, BNIP3 peptide mimetics, fusion proteins of any of the foregoing (e.g., with the constant domain of an antibody or with albumin), or modified derivatives of any of the foregoing. The agent can also be a chemical compound that can inhibit BNIP3 including agents that block PT pore opening such as cyclosporin A or bongkrekic acid. Examples of some of the agents that modulate BNIP3 are provided below.

(i) BNIP3 and BNIP3 Mutants

In one embodiment, the agent that can modulate BNIP3 is a nucleic acid moecule encoding a BNIP3 protein or is a BNIP3 protein. The nucleic acid encoding BNIP3 or the BNIP3 protein can be selected from any of the known BNIP3 sequences known in the art. In particular, the BNIP3 protein may have the sequence provided in GenBank under accession number NM-004052 (SEQ ID NO: 19).

Figure 14:
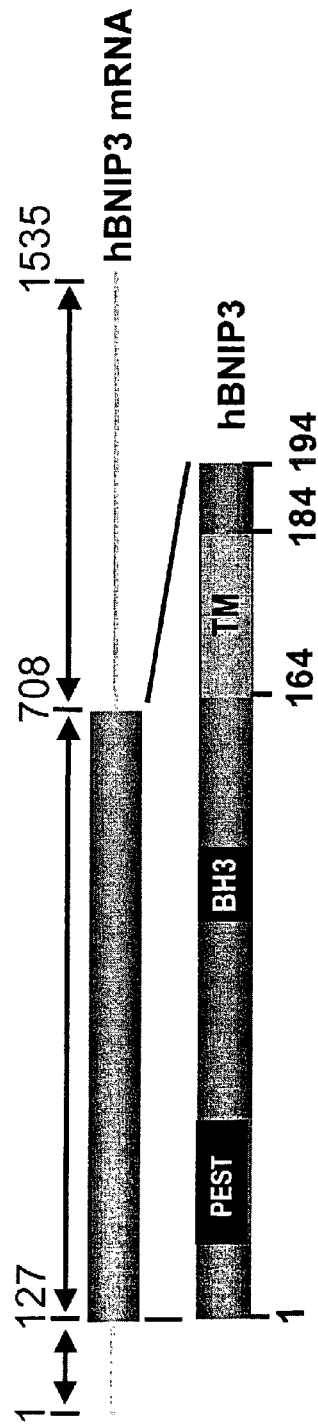
FIG. 14 shows the functional domains of hBNIP3.

To prevent necrosis, the BNIP nucleic acid or protein may be a BNIP3 mutant that can inhibit cell death caused by BNIP3. The functional domains of BNIP3 are shown in FIG. 14 and a series of structural and functional mutants were constructed and are listed in Table 1 and SEQ ID Nos. 2-7. All of these mutants exhibit a characteristic structural or functional loss. Some, for example BNIP3ΔTM, can act as dominant negatives, thereby interfering with the natural function of BNIP3, while other construct products have a point mutation that totally eliminates the cell death function of BNIP3.

In a specific embodiment, the BNIP3 mutant is a carboxyl terminal transmembrane deletion mutant of BNIP3 known as BNIP3ΔTM herein. BNIP3ΔTM has a deletion in amino acids 164 to 194 which is in the transmembrane domain. The BNIP3ΔTM mutant is unable to integrate into the mitochondria and the inventors have shown that it is able to block the cytotoxic effect of the endogenous BNIP3 protein.

In addition to the known BNIP3 proteins and mutants, the present invention also includes analogs, derivatives and fragments of BNIP3 and BNIP3 mutants that retain the ability to induce or inhibit cell death, respectively.

The term "analog" as used herein includes any peptide having an amino acid residue sequence substantially identical to any of the wild type BNIP3 or mutant BNIP3 sequences in which one or more residues have been conservatively substituted with a functionally similar residue and which displays the ability to induce cell death similar to endogenous BNIP3 or inhibit cell death similar to the BNIP3 mutants. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" as used herein refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of an BNIP3 protein, so long as the requisite activity is maintained.

The term "fragment" refers to any subject peptide having an amino acid residue sequence shorter than that of a BNIP3 protein or mutant (including analogs, derivatives or mimetics) that retains the ability to modulate cell death.

(ii) Antisense Oligonucleotides

In another embodiment, the agent that can modulate BNIP3 is an antisense oligonucleotide that inhibits the expression of the BNIP3 gene. The term "antisense oligonucleotide" as used herein means a nucleotide sequence that is complimentary to its target, e.g. the BNIP3 gene.

The term "oligonucleotide" as used herein refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides that contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene (e.g. phosphorothioate derivatives and acridine substituted nucleotides). The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

(iii) Antibodies

In another embodiment, the agent that can modulate BNIP3 is a BNIP3 specific antibody. Several antibodies to BNIP3 are readily available including both polyclonal and monoclonal antibodies as described in the Examples.

Antibodies to BNIP3 may be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')$_2$) and recombinantly produced binding partners.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell, having immortality, such as a myeloma cell, to provide a fused cell hybrid which has immortality and secretes the required antibody. The cells are then cultured, in bulk, and the monoclonal antibodies harvested from the culture media for use.

For producing recombinant antibodies (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art. (see for a general discussion Harlow & Lane *Antibodies: A Laboratory Manual,* Cold Spring Harbor Laboratory Publications, New York, 1988 and Borrebaeck, *Antibody Engineering-A Practical Guide,* W. H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}$C and iodination.

(iv) Peptide Mimetics

The present invention also includes peptide mimetics of the BNIP3 protein. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a BNIP3 peptide, or enhancer or inhibitor of the BNIP3 peptide. Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad, Sci USA 89:9367), and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

(v) Other Substances

In addition to the above agents, other substances that can modulate BNIP3 can also be identified and used in the methods of the invention. For example, substances which can bind BNIP3 may be identified by reacting BNIP3 with a substance which potentially binds to BNIP3, then detecting if complexes between the BNIP3 and the substance have formed. Substances that bind BNIP3 in this assay can be further assessed to determine if they are useful in modulating or inhibiting BNIP3 and useful in the therapeutic methods of the invention.

Accordingly, the present invention also includes a method of identifying substances which can bind to BNIP3 comprising the steps of:

(a) reacting BNIP3 and a test substance, under conditions which allow for formation of a complex between the BNIP3 and the test substance, and (b) assaying for complexes of BNIP3 and the test substance, for free substance or for non complexed BNIP3, wherein the presence of complexes indicates that the test substance is capable of binding BNIP3.

Conditions which permit the formation of substance and BNIP3 complexes may be selected having regard to factors such as the nature and amounts of the substance and the protein.

The substance-BNIP3 complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against BNIP3 or the substance, or labelled BNIP3, or a labelled substance may be utilized. The antibodies, BNIP3, or substances may be labelled with a detectable substance.

The BNIP3 or the test substance used in the method of the invention may be insolubilized. For example, the BNIP3 or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, silica, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized BNIP3 or substance may be prepared by reacting the material with a suitable insoluble carrier using known chemical or physical methods, for example, cyanogen bromide coupling.

The BNIP3 or test substance may also be expressed on the surface of a cell in the above assay.

The BNIP3 gene or protein may be used as a target for identifying lead compounds for drug development. The invention therefore includes an assay system for determining the effect of a test compound or candidate drug on the activity of the BNIP3 gene or protein.

Accordingly, the present invention provides a method for identifying a compound that modulates BNIP3 gene or protein activity comprising:

(a) incubating a test compound with a BNIP3 protein or a nucleic acid encoding a BNIP3 protein; and (b) determining the effect of the test compound on BNIP3 protein activity or BNIP3 gene expression and comparing with a control (i.e. in the absence of a test compound) wherein a change in the BNIP3 protein activity or BNIP3 gene expression as compared to the control indicates that the test compound is a potential modulator of the BNIP3 gene or protein.

III. Compositions

The present invention also includes pharmaceutical compositions containing the agents that can modulate, induce or inhibit BNIP3 for use in the methods of the invention. Accordingly, the present invention provides a pharmaceutical composition for modulating necrosis comprising an effective amount of an agent that can modulate BNIP3 in admixture with a suitable diluent or carrier. The present invention further provides a pharmaceutical composition for inhibiting necrosis comprising an effective amount of an agent that can inhibit BNIP3 in admixture with a suitable diluent or carrier. The present invention also provides a pharmaceutical composition for treating a neurological disease comprising an effective amount of an agent that can inhibit BNIP3 in admixture with a suitable diluent or carrier. The present invention also provides a pharmaceutical composition for treating a cardiovascular disease comprising an effective amount of an agent that can inhibit BNIP3 in admixture with a suitable diluent or carrier.

The compositions of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the methods of the present invention, the composition of the present invention can be administered in various ways. When the active agent is a compound, it can be administered as the compound or as pharmaceutically acceptable salt and can be administered alone or as an active ingredient in combination with pharmaceutically acceptable carriers, diluents, adjuvants and vehicles. The compositions can be administered orally, topically, rectally, subcutaneously or parenterally including intravenous, intraarterial, intramuscular, intracerebral intraperitoneally, and intranasal administration as well as intrathecal and infusion techniques. Implants of the compounds may also be useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than mice or other experimental animals which treatment has a length proportional to the length of the disease process and drug effectiveness. The doses can be single doses or multiple doses over a period of several days, but single doses are preferred.

The doses can be single doses or multiple doses over a period of several days. The treatment generally has a length proportional to the length of the disease process and drug effectiveness and the patient species being treated.

When administering the composition of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, cheating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the composition utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the composition of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered can vary for the patient being treated and can vary from about 100 ng/kg of body weight to 100 mg/kg of body weight per day and preferably can be from 10 mg/kg to 10 mg/kg per day.

When the agent to be delivered is in the form of a nucleic acid molecule (including nucleic acid molecules that encode BNIP3 or mutants thereof, as well as antisense oligonucleotides), the nucleic acid can be delivered to the cell or animal using standard gene therapy approaches. For example, see in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy, cells are removed from a patient and are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998). These genetically altered cells have been shown to express the transfected genetic material in situ.

The gene expression vehicle is capable of delivery/transfer of heterologous nucleic acid into a host cell. The expression vehicle can include elements to control targeting, expression and transcription of the nucleic acid in a cell selective manner as is known in the art. It should be noted that often the 5'UTR and/or 3'UTR of the gene can be replaced by the 5'UTR and/or 3'UTR of the expression vehicle. Therefore as used herein the expression vehicle can, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that can be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1989, 1992), in Ausubel et al., *Current Protocols in Molecular Biology,* John Wiley and Sons, Baltimore, Md. (1989), Chang et al., *Somatic Gene Therapy,* CRC Press, Ann Arbor, Mich. (1995), Vega et al., *Gene Targeting,* CRC Press, Ann Arbor, Mich. (1995), *Vectors: A Survey of Molecular Cloning Vectors and Their Uses,* Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation do not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention depends on desired cell type to be targeted and is known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed do not contain a genome and therefore cannot proceed through subsequent rounds of infection. The specific type of vector depends upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neurodegenerative diseases. Following injection, the viral vectors circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The following non-limiting examples are illustrative of the present invention:

EXAMPLES

Methods

General Methods in Molecular Biology

Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., Recombinant DNA, Scientific American Books, New York and in Birren et al (eds) *Genome Analysis: A Laboratory Manual Series*, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in *PCR Protocols: A Guide To Methods And Applications,* Academic Press, San Diego, Calif. (1990). In-situ (In-cell) PCR in combination with Flow Cytometry can be used for detection of cells containing specific DNA and mRNA sequences (Testoni et al, 1996, Blood 87: 3822).

General Methods in Immunology

Standard methods in immunology known in the art and not specifically described are generally followed as in Stites et al. (eds), *Basic and Clinical Immunology* (8th Edition), Appleton & Lange, Norwalk, Conn. (1994) and Mishell and Shiigi (eds), *Selected Methods in Cellular Immunology*, W. H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, New York, 1989.

Recombinant Protein Purification

Marshak et al, "Strategies for Protein Purification and Characterization. A laboratory course manual." CSHL Press, 1996.

Transgenic and Knockout Methods

The present invention can provide for transgenic gene and polymorphic gene animal and cellular (cell lines) models as well as for knockout models. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

Example 1

Materials and Methods

Cell Lines

MCF-7 and HeLa cells were cultured in a minimal essential medium (MEM) (Gibco-BRL) supplemented with 10% fetal bovine serum (FBS) (Cansera), 1% MEM sodium pyruvate (Gibco-BRL), 1% HEPES (Gibco-BRL), and 1% L-glutamine (Gibco-BRL). Mouse embryonic fibroblasts (MEFs) deficient in Apaf-1, caspase 9, or caspase 3 were cultured as previously described (Hakem, R. et al, 1998). 293T and 293-Bcl-2 cells were cultured in Dulbecco's modified Eagle's medium (DMEM) (Gibco-BRL) supplemented with 10% FBS.

Expression Plasmids

T7-tagged pcDNA3-BNIP3, T7-tagged pcDNA3-BNIP3ΔTM (Chen, G. et al, 1997), and HA-tagged pcDNA3-BNIP3 (Chen, G. et al, 1999) have been described previously. pcDNA3-caspase-9-His6 and pcDNA1-p35 were gifts from Emad Alnemri (Thomas Jefferson University, Philadelphia, Pa.). pcDNA3-Apaf-1 and pFLAG-CMV-5a-tBID were provided by Xiaodong Wang (Howard Hughes Medical Institute, Dallas, Tex.) and Junying Yuan (Harvard Medical School, Boston, Mass.), respectively.

Reagents

Murine monoclonal anti-T7 antibody was purchased from Novagen (Madison, Wis.). Murine monoclonal anti-cytochrome c antibodies for immunoblotting (65981A) and immunofluorescence (67971A) were purchased from Pharmingen. Mouse monoclonal anti-poly (ADP-ribose) polymerase, anti-BCL-XL, and antiactin antibodies were purchased from Alexis Biochemicals (San Diego, Calif.), Transduction Laboratories (Lexington, Ky.), and ICN Biochemicals (Montreal, Canada), respectively. Rabbit polyclonal anti-AIF was a gift from Guido Kroemer (CNRS, Paris, France). Rabbit anti-FLAG polyclonal antibody and mouse anti-HA monoclonal antibody were purchased from Zymed (South San Francisco, Calif.) and Boehringer Mannheim (Indianapolis, Ind.), respectively. Secondary antibodies, goat anti-mouse immunoglobulin G (IgG)-horseradish peroxidase, goat anti-mouse IgG-fluorescein isothiocyanate (FITC), and goat anti-rabbit IgG-FITC were all purchased from Sigma Chemical Co. (St. Louis, Mo.). Goat anti-mouse IgG-Cy3 was from Chemicon (Temecula, Calif.).

Assessment of Mitochondrial Protein Targeting and Orientation

MCF-7 and 293T cells (106) were transiently transfected with LipofectAmine reagent (Gibco-BRL) with 8 mg of DNA for 12 hours. Mitochondria were isolated according to Goping et al. (Goping, I. S. et al, 1998) with modifications. Briefly, at 4° C., thigh muscle from the mouse hind limb or transfected cells were isolated or scraped, respectively, and washed twice in 5 ml of HIM (0.2% [wt/vol] bovine serum albumin, 200 mM mannitol, 70 mM sucrose, 10 mM HEPES-KOH, 1 mM EGTA [pH 7.5]). Cells were resuspended in 2 ml of HIM and homogenized on ice three times for 3 to 10 seconds using a Poltron homogenizer (setting 6.5). Large cellular debris was removed from the homogenate via centrifugation at 430 3 g for 10 minutes. The supernatant was diluted in HIM (minus bovine serum albumin), and mitochondria were collected by centrifugation at 5,400 3 g for 10 minutes and resuspended in cMRM (250 mM sucrose, 10 mM HEPES-KOH, 1 mM ATP, 5 mM sodium succinate, 0.08 mM ADP, 2 mM K2 HP04 [pH 7.5]) to 1 mg of mitochondrial protein per ml and adjusted to 1 mM dithiothreitol just prior to use.

To assess the association of proteins with the mitochondrial membrane, 30 or 100 mg of mitochondria isolated from transfected cells or tissue, respectively, were pelleted and resuspended to 0.25 mg of protein per ml in freshly prepared 0.1 M Na2 C03 (pH 11.5) and incubated on ice for 30 minutes (Goping, I. S. et al, 1998). Mitochondrial membranes were collected via ultracentrifugation at 100,000 3 g for 1 hour at 4° C. in a Beckman Optima TLX ultracentrifuge (Beckman Instruments, Fullerton, Calif.). Association of the proteins with the mitochondrial membrane was assessed via Western blot analysis of the pellets and the lyophilized supernatants. To determine protein orientation, 293T cells were transiently transfected with T7tagged BNIP3 and incubated with 3 mg of trypsin (Sigma) per ml for 10 minutes on ice. Trypsin was inactivated with a 100-fold excess of soybean trypsin inhibitor (Sigma). Trypsin-treated mitochondria were pelleted, subjected to alkali elution, and immunoblotted with mouse monoclonal anti-BNIP3 (Ana40) or anti-T7 (Novagen) antibodies.

b-Galactosidase Cell Death Assay

Various doses of the peptide caspase inhibitor Ac-zVAD-fmk (Enzyme System Products, Dublin, Calif.) were applied to $1 \times 10^5$ 293T cells cotransfected, using LipofectAmine reagent (Gibco-BRL), with 0.01 mg of the reporter plasmid pcDNA3bgal plus the indicated expression plasmids to a final amount of 0.75 mg of DNA (see FIG. 2), as adjusted with empty vector. Cells were fixed, stained, and evaluated 27 hours posttransfection as described previously (Miura, M. et al., 1993). Similar strategies were used to evaluate the expression of pcDNA1-p35 as a caspase inhibitor (1.95 mg of DNA total) and to determine the killing efficiency of BNIP3 expressed in MEF cells (1.2 mg of DNA with 0.3 mg of b-galactosidase).

Assessment of Caspase Activation

Lysates were collected from 293T cells, transiently transfected via the CaP04 method (Ray, R., et al., 1999), at the indicated times. Aliquots of these lysates were run under Laemmli sodium dodecyl sulfate-polyacrylamide gel electrophoresis (SDS-PAGE) conditions and immunoblotted with mouse monoclonal anti-PARP. Results were visualized with an enhanced chemiluminescence system (Amersham Pharmacia Biotech, Amersham, U. K.). Transfected 293T cells were also assayed for caspase cleavage via colorigenic cleavage of the peptide Ac-DEVD-pNA (Biomol, Plymouth Meeting, Pa.), according to the conditions outlined by Quignon et al. (Scaffidi, C., et al., 1998), using 100 mM peptide. Where appropriate, samples were preincubated with 500 nM Ac-DEVD-fmk for 30 minutes at room temperature. Data were acquired on a Multiskan MCC/340 (Titertek) plate reader at 405 nm.

Assessment of Cytochrome c Release

Mitochondria were isolated from CaPO4-transfected 293T cells using 70 strokes (tight pestle) in a 1-ml Dounce homogenizer (Wheaton) in 300 ml of CFS buffer as previously described (Thornberry, N. A., et al., 1998). Mitochondria were resuspended in H buffer (Thornberry, N. A., et al., 1998). Aliquots of 5 mg of protein were analyzed on Laemmli SDS-15% PAGE gels and immunoblotted with anticytochrome c monoclonal antibody. Equal loading was ensured by probing the same blot with monoclonal antiactin. Results were visualized with enhanced chemiluminescence. Cytochrome c release was also determined via indirect immunofluorescence of transfected MCF-7 and 293T cells. Briefly, cells grown on coverslips were costained with Cy3-conjugated mouse anti-cytochrome c monoclonal antibody and an appropriate tag (HA for BNIP3 and FLAG for tBID), which was visualized with FITC-conjugated goat anti-rabbit IgG. Cells were also stained with Hoechst dye to determine apoptotic nuclear morphology. No fewer than 200 cells were scored for each sample. Fluorescence was visualized and captured using a Zeiss axiophot microscope equipped with a cooled charge-coupled device camera.

DNA Fragmentation Assays and Annexin V Staining

DNA fragmentation was detected using the in situ cell death detection kit with fluorescein (Boehringer Mannheim) as per the manufacturer's recommendations in the presence or absence of 50 mM Ac-zVAD-fmk or Ac-FA-fmk. Images were captured as described earlier. No fewer than 200 nuclei were scored manually for each sample. Annexin V staining was performed exactly as described by the manufacturer (Boehringer Mannheim), and samples were analyzed via flow cytometry.

Assessment of PT Pore Opening by Confocal Imaging

Aliquots of 293T cells were grown on coverslips, and 9 to 10 hours after BNIP3 or control transfections using the CaPO4 method, the cells were washed with Hanks' balanced salt solution-10 mM HEPES (pH 7.2) (HH buffer) before staining with 1 mM calcein-AM ester (Molecular Probes, Eugene, Oreg.) and 5 mM CoCl2 at room temperature for 15 minutes. The CoCl2 was added to quench the cytoplasmic staining so only the fluorescent mitochondria were imaged (Bernardi, P. et al, 1999). Cells were washed four times and resuspended in HH buffer before imaging on an Olympus IX70 inverted confocal laser microscope using Fluoview 2.0 software (Carson Group Inc., Markham, Ontario, Canada). A bandpass filter of 488 nm was used for capturing the calcein images, while Nomarski optics were used to obtain transmitted light images of the cells. To determine the mitochondrial calcein fluorescence levels, individual cells were identified using Nomarski optics and total mitochondrial fluorescence per cell was measured using Northern Eclipse software, version 5.0 (Empix Inc., Toronto, Ontario, Canada).

Mitochondrial Dcm and ROS Production

Changes in mitochondrial function were determined by incubating 10 6 293T cells, transiently transfected via the CaPO4 method, with either 1 mM JC-1, 40 nM DiOC6, or 2 mM dihydroethidium (HE) (all from Molecular Probes, Inc.) for 30 minutes at 37° C. in Hanks' balanced salt solution (Gibco-BRL). Cells were scored using a FACScalibur flow cytometer (Becton-Dickinson, San Jose, Calif.), and data were analyzed on Celiquest software, version 3.1 (Becton-Dickinson). Controls were performed in the presence or absence of 50 mM mClCCP (Sigma) or an excess of 30% H2 02. For inhibition experiments, cyclosporin A (Sigma) or bongkrekic acid (a gift from J. A. Duine, Delft University, Delft, The Netherlands) was added 2 hours prior to transfection. All cells were harvested 8 hours after transfection and stained with 40 nM DiOC6, 2 mM HE, or 1 mg of propidium iodide (PI) (Sigma) per ml. In all cases, samples were gated to exclude cellular debris.

Electron Microscopy

Transfected 293T cells were fixed with 2% paraformaldehyde-0.1% gluteraldehyde in 0.1 M sodium cacodylate for 1 to 2 hours at room temperature. Cells were postfixed with 1% osmium tetroxide for 1.5 hours, washed, and block stained for 1 hour in 3% aqueous uranyl acetate. The samples were then washed again, dehydrated with graded alcohol, and embedded in Epon-Araldyte resin (Maynard Scientific). Ultrathin sections were cut on a Reichert ultramicrotome, counterstained with 0.3% lead citrate, and examined on a Philips EM420 electron microscope.

Results

Mitochondrial Membrane Expression and Integration of BNIP3

Polyclonal and monoclonal antibodies to BNIP3 were developed to examine protein expression in tissues and cell lines. Surprisingly, high levels of protein expression were found only in postnuclear lysates of murine and human skeletal muscle but not in other tissues (e. g., thymus, spleen, lung, kidney, heart, and brain) (FIG. 1A) or in many human and murine cell lines examined. Following subcellular fractionation, the skeletal muscle BNIP3 protein was recovered in heavy membrane fractions enriched for mitochondria but not in the S-100 cytosol (FIG. 1A, left panel). Subsequent reexamination of several human cell lines that had been negative in cell lysates by Western blotting revealed small amounts of BNIP3 protein in purified mitochondrial fractions using monoclonal anti-human BNIP3 (hBNIP3) Ana40. Again, no protein was detected in S-100 cytosol (FIG. 1A, right panel). The significance of these observations was unclear, as skeletal muscle is a terminally differentiated tissue and largely unaffected by programmed cell death, and the cell lines were completely viable. However, it did indicate that the endogenous BNIP3 in skeletal muscle must be inactive. Recent studies by Goping et al. (Goping, I. S. et al, 1998) found that endogenous BAX is only loosely associated with the mitochondrial membrane in normal cell lines, but following death signals, it integrates fully and becomes active. The mitochondrial membrane association of BNIP3 in normal skeletal muscle and following transient transfection and initiation of apoptosis was examined.

The membrane association of BNIP3 was determined following alkali extraction of mitochondria, which dissociates arid solubilizes unintegrated protein. BNIP3 in mouse skeletal muscle was exclusively associated with the mitochondrionenriched heavy membrane pellet in normal buffers (FIG. 1A), but following alkali treatment, the majority of the protein was soluble and detected in the S-100 supernatant. In contrast, endogenous BCL-XL from murine muscle remained tightly associated with the heavy membrane fractions following alkali treatment, as expected of an integral membrane protein (FIG. 1B, lower panel). A similar experiment was performed using mitochondria derived from 293T or MCF-7 cells transiently transfected with BNIP3. In contrast to the endogenous protein, transfected BNIP3 remained tightly associated with the heavy membrane fractions following alkali elution (FIG. 1B).

Integrated BNIP3 has an Ncyto-Cin Orientation in the Mitochondrial Outer Membrane The orientation of a protein in any membrane can be a contributing factor to its function and regulation (Nguyen, M. et al, 1993). The trypsin cleavage sites in the BNIP3 TM domain (amino acids 164 to 184) were exploited and the epitope recognized by the monoclonal anti-BNIP3 antibody Ana40 (amino acids 112 to 124) to determine the mitochondrial membrane orientation of transfected BNIP3 bearing a C-terminal T7 tag.

There are three possible orientations for BNIP3 in the mitochondrial membrane that can be detected by this method: (i) mitochondrial inner membrane, (ii) mitochondrial outer membrane with an Ncyto-Cin orientation, or (iii) mitochondrial outer membrane with an Nin-Ccyto orientation. Integration of BNIP3 into the mitochondrial inner membrane would prevent exposure to trypsin and thus result in an undigested 40-kDa BNIP3 homodimer detectable by both Ana40 and anti-T7 antibodies. Alternatively, orientation of BNIP3 such that the C terminus is cytosolic would permit cleavage at R185 and R186, yielding a truncated BNIP3 homodimer of 38 kDa that would be detected by Ana40 but not by anti-T7 antibody since the C-terminal T7 tag would be lost. Finally, a cytosolic N-terminal orientation would yield truncated fragments detectable by one or both antibodies. Following isolation of mitochondria from BNIP3-transfected cells and trypsin digestion, a prominent 18-kDa band was recognized by both antibodies and an 8-kDa band was detected by the anti-T7 but not the Ana40 antibody (FIG. 1C). The 8-kDa band was detected in the heavy membrane pellet fraction. Thus, the 8-kDa band would contain the extreme C-terminal T7 epitope and is likely a dimer of two 4-kDa monomeric C-terminal fragments representing approximately amino acids 154 to 194. This pattern is consistent with the integration of BNIP3 in the mitochondrial outer membrane in the Ncyto-Cin orientation.

BNIP3-induced Cell Death is Caspase Independent and does not Induce Cytochrome c Release To determine if BNIP3-induced cell death was mediated by caspases, the effectiveness of the broad-spectrum peptide caspase inhibitor Ac-zVAD-fmk and the baculovirus antiapoptotic gene p35 were evaluated in ability of preventing BNIP3-induced cell death following transient transfection of 293T cells. BNIP3-induced cell death was unaffected by the same concentration of inhibitor that effectively suppressed either tBID or caspase 9/Apaf-1 transfectants by greater than 50% (FIG. 2A). Furthermore, p35 plasmid was similarly ineffective in abrogating BNIP3 cell death at concentrations of up to 1.5 mg, well above the 0.5 mg of p35 plasmid required to block caspase 9/Apaf-1-induced cell death (FIG. 2B).

The caspase substrate Ac-DEVD-pNA was used to detect the activation of caspase 3-like proteases in 293T cells transiently transfected with either BNIP3, tBID, or the inactive mutant BNIP3DTM. Cells were harvested at 1, 12, 18, 24, and 36 hours posttransfection, and lysates were prepared and incubated with the substrate. Lysates from cells transfected with either BNIP3 or BNIP3DTM revealed only marginal increases in proteolytic activity and were not inhibited by the caspase inhibitor of the same specificity as Ac-DEVD-fmk (FIG. 3A). In contrast, tBID- transfected cells exhibited a fourfold increase in substrate cleavage, and this was blocked by treatment with Ac-DEVD-fmk (FIG. 3A). Lysates from BAX transfectants were similar to those of tBID transfectants (data not shown).

Whole-cell lysates of BNIP3-expressing 293T cells collected at 12, 24, 36, and 48 hours posttransfection were immunoblotted for the caspase substrate PARP and found little evidence of proteolysis (FIG. 3B) and no processing of procaspase 3 (FIG. 3C). In contrast, efficient processing of PARP from 116 to 86 kDa (FIG. 3B) and procaspases 3 (FIG. 3C), 7, and 9 were detected in lysates from BAX transfectants. No processing of caspases 7 and 9 was detected in BNIP3 lysates up to 36 hours.

Figure 4A:
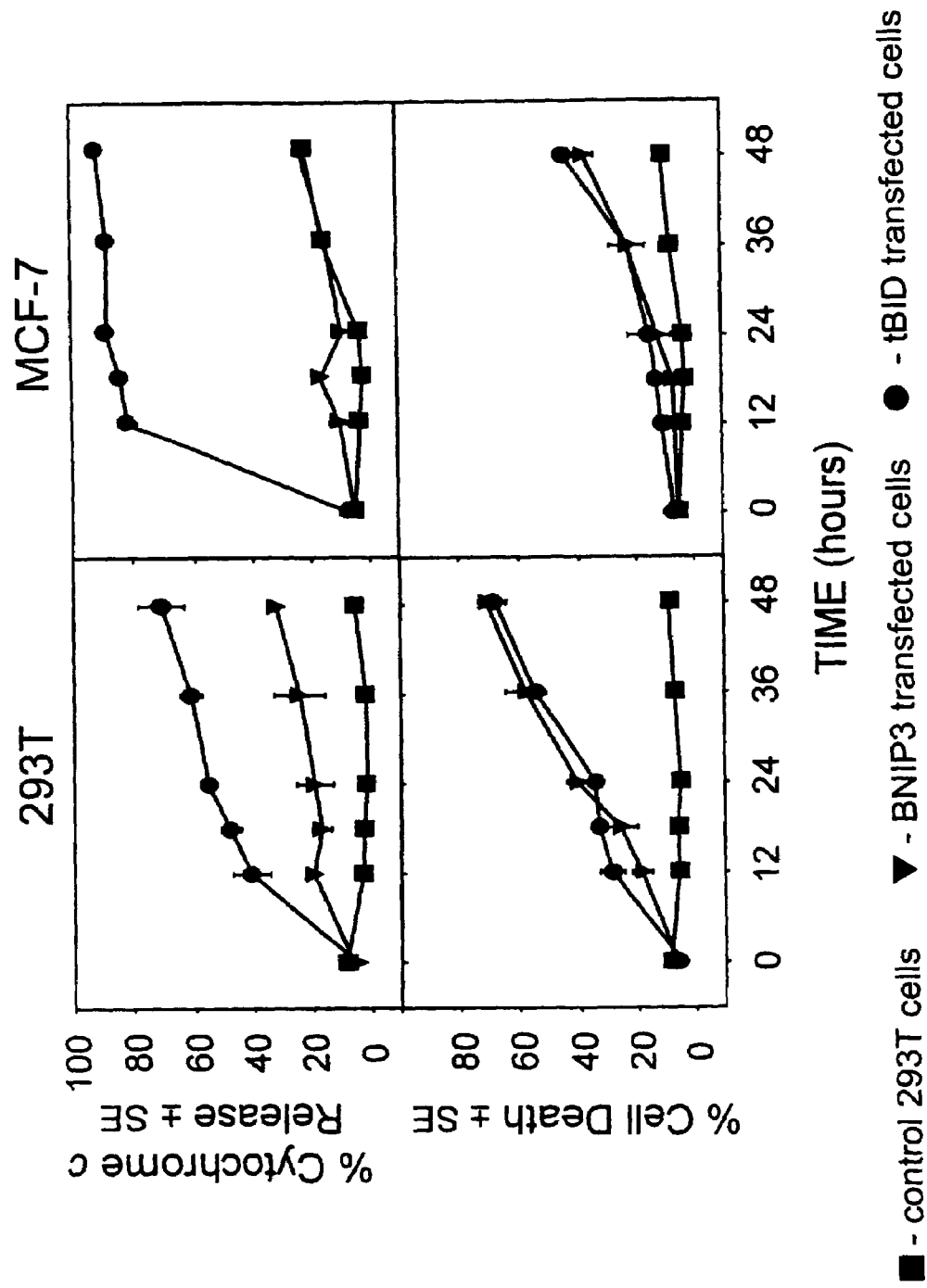
FIGS. 4A and B show that BNIP3 does not induce mitochondrial cytochrome c release.

Since BNIP3 integrates into the mitochondrial outer membrane, it can act to initiate cell death by mitochondrial perturbation and the release of cytochrome c, a cofactor for Apaf-1. Indirect immunofluorescence was initially used to examine cytochrome c release from cells expressing BNIP3 following transient transfection. BNIP3- and BNIP3DTM-expressing cells, detected by immunostaining for the C-terminal epitope tag, showed no significant cytochrome c release in MCF-7 cells, which are caspase 3 deficient, and only very low levels in 293T cells (FIG. 4A). On the other hand, 91% of MCF-7 and 71% of 293T cells released cytochrome c 48 hours after transfection with tBID, while the level of cell death induced by tBID and BNIP3 was equivalent (FIG. 4A). In tBID-transfected cells, cytochrome c was released prior to apoptosis, as determined by Hoechst dye staining.

Figure 4B:
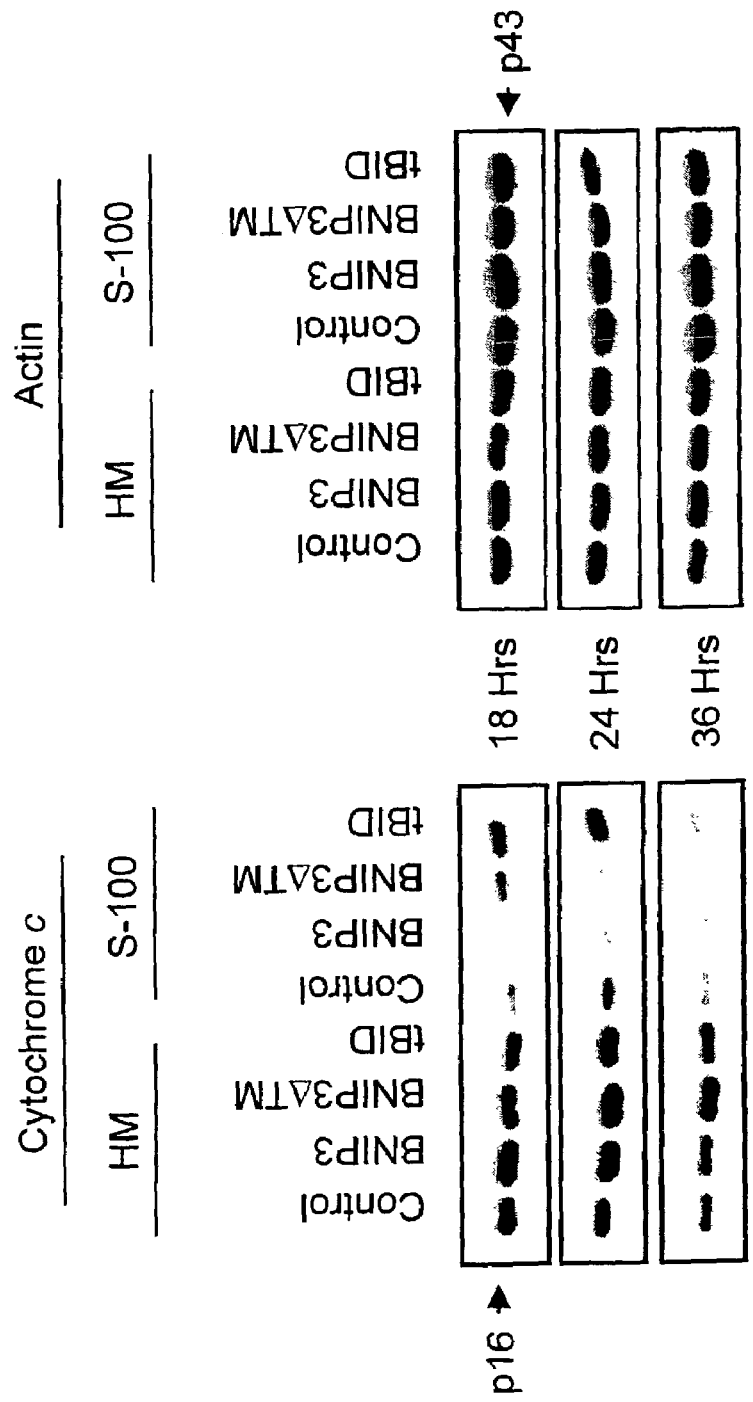

Cytochrome c release was reexamined by Western blotting heavy membrane (HM) and S-100 subcellular fractions of 293T cells at 18, 24, and 36 hours posttransfection. A significant increase in cytochrome c was seen in the S-100 fractions of tBfD but not BNIP3 transfectants at 18 and 24 hours (FIG. 4B). Loss of cell viability of tBID and BNIP3 transfectants was equivalent, as determined by trypan blue dye exclusion. The decrease in cytochrome c levels in S-100 of tBID-expressing cells at 36 hours was concomitant with extensive cell death. S-100 cytochrome c levels in BNIP3-transfected cells were similar to that of the inactive BNIP3DTM and control cells despite a fivefold difference in viability (FIG. 4B). A time course revealed that chromatin condensation following BNIP3 transfection preceded the release of cytochrome c, indicating that it could not be responsible for the nuclear changes.

BNIP3 Induces Cell Death in Fibroblasts Deficient in Apaf-1, Caspase 9, or Caspase 3

Since the above experiments suggested that BNIP3 induced cell death without cytochrome c release or caspase activation, the function of BNIP3 in cells lacking Apaf-1 or Apaf-1-activated caspases 9 and 3 was examined. Using the bgalactosidase cell death assay, wild-type, Apaf-1 2/2, caspase 9 2/2, and caspase 3 2/2 MEFs were transiently transfected with either BNIP3 or BNIP3DTM. BNIP3 was able to induce cell death (50%) in the wild-type and all mutant MEF lines tested (FIG. 5A). In contrast, the mutant cells exhibited profound resistance to adriamycin-induced cell death (FIG. 5B), confirming an earlier report (Hakem, R. et al, 1998). Immunoblot analysis of whole-cell lysates showed equal expression of BNIP3 and BNIP3DTM in all of the MEF cell lines.

Rapid Loss of Plasma Membrane Permeability in BNIP3-transfected Cells

Cells undergoing apoptosis externalize phosphatidylserine (PS) while maintaining an intact plasma membrane (McConkey, D. J. 1998). A time course following BNIP3 transfection identified increased plasma membrane permeability as early as 2 hours posttransfection and did not increase further over the following 12 hours as determined by the failure of cells to exclude PI (FIG. 6A). Cells gated to determine annexin binding as a measure of phosphatidylserine externalization in PI 2 populations at 12 hours revealed no increase in annexin staining of BNIP3-transfected in cells that excluded PI, in contrast to cells transfected with tBID, BAX, or caspase 9/Apaf-1 (FIG. 6B). BNIP3-expressing cells analyzed at 18 and 24 hours similarly did not show any increase in annexin staining in PI 2 cells. Thus, BNIP3 induces early permeability of the plasma membrane but not PS externalization.

BNIP3 Induces Late DNA Fragmentation that is Independent of AIF Translocation

DNA fragmentation and chromatin condensation are hallmarks of caspase dependent apoptotic cell death and have been consistently seen in BNIP3-transfected cells (Chen, G. et al, 1999, Chen, G. et al, 1997). Since it was demonstrated that plasma membrane was damaged early following BNIP3 expression, the relative rate at which DNA fragmentation occurred was examined using the TUNEL (terminal deoxynucleotidyltransferase-mediated dUTP-biotin nick end labeling) assay. BNIP3 transfectants showed increasing levels of TUNEL-positive cells over time, but no activity was detected until 18 to 24 hours and maximal levels were not reached until 36 hours, much slower than tBID-induced DNA damage (FIG. 7A). This contrasts with the initiation of plasma membrane damage by BNIP3 at 8 hours and its completion by 18 hours. In addition, it was observed that only two or three TUNEL-positive foci in BNIP3-expressing cells, while tBID-transfected cells exhibited much more extensive nuclear fragmentation, with six to ten TUNEL-positive foci per cell (FIG. 7B). DNA fragmentation could only be partially inhibited with 50 mM Ac-zVAD-fmk in BNIP3 transfectants but was nearly completely inhibited in tBID-expressing cells (FIG. 7C). No effect was observed in parallel populations treated with 50 mM Ac-FA-fmk. The DNA fragmentation observed by TUNEL staining on agarose gels stained with ethidium bromide was confirmed. An oligonucleosomal ladder was easily detected in tBID transfectants at 18, 24, and 36 hours, while little DNA degradation and ladder formation was observed in BNIP3 transfectants even at 36 hours.

Since wild-type BNIP3-induced chromatin condensation and DNA fragmentation were not completely blocked by treatment with Ac-zVAD-fmk, AIF can also mediate the BNIP3 effects. AIF is a mitochondrial flavoprotein which, in response to an apoptotic stimulus, translocates to the nucleus to induce chromatin condensation and high-molecular weight DNA fragmentation (Tsujimoto, Y. 1997). Immunofluorescence analysis and immunoblotting of heavy membrane fractions of BNIP3-transfected 293T cells at 18, 24, and 36 hours posttransfection found no AIF nuclear translocation despite increases in the proportion of cells with condensed chromatin by Hoechst staining (C. Vande Velde, J. Cizeau, E. Daugas, G. Kroemer, and A. H. Greenberg, unpublished data).

BNIP3-expressing Cells have Ultrastructural Features of Necrosis

To determine the fine ultrastructural features of cells following BNIP3 expression, transmission electron microscopy of 293T cells 24 hours posttransfection was performed. These experiments revealed a nuclear phenotype of lightly dispersed foci of chromatin condensation and heterochromatin (FIG. 8B) rather than the globular condensation typical of apoptosis. During a detailed examination of cellular organelles, many rounded mitochondria were detected in which the internal cisternae had been destroyed, while the inner and outer membranes of the mitochondria appeared to be intact in most cells (FIG. 8C). The mitochondria did not appear to be undergoing gross swelling. Surprisingly, BNIP3 transfectants were characterized by extensive cytoplasmic vacuolation and dense bodies. High-power examination of these structures revealed a heterogeneous mixture of electronlucent and electrondense regions, many of which appear to be vacuoles and autophagosomes (FIGS. 8D and E), and some of the autophagic vacuoles contained whorls of membranous material (FIG. 8F) that have been observed during autophagic cell death (Yasuda, M., et al., 1998).

BNIP3 Induces Mitochondrial PT Pore Opening, Loss of Dcm, and Increased ROS Production Since the studies to this point had established that BNIP3 was a mitochondrial outer membrane protein and electron micrographs of BNIP3-transfected cells featured disturbances in mitochondrial structure, it was established that BNIP3 can directly induce mitochondrial dysfunction. Opening of the mitochondrial PT pore often accompanies both apoptotic and necrotic cell death, with the consequent loss of transmembrane potential (Dcm) and respiratory inhibition with ROS production. The status of the PT pore can be, determined with the membrane-permeating fluorescent probe calcein-AM, which freely enters mitochondria but cannot exit except through an open PT pore following processing by cellular esterases. Using $CoCl_2$ quenching of cytosolic fluorescence as described by Bernardi et al. (Bernardi, P. et al, 1999), the release of calcein from mitochondria was analyzed by confocal laser microscopy and quantitative image analysis. Following BNIP3 transfection, 293T cells lose mitochondrial calcein staining as early as 8 hours posttransfection (FIGS. 9A and B), indicating rapid opening of the PT pore.

To determine if BNIP3-expressing cells also decrease their transmembrane potential and produce ROS, cell-permeating lipophilic dyes JC-1 and HE were used and the dyes assessed the staining by flow cytometry using gates established from normal untransfected 293T cells. At 24 hours posttransfection, cells were collected, stained, and analyzed. BNIP3 was almost as efficient as tBID at suppressing Dcm, increasing ROS generation, and inducing cell death (FIGS. 9C to E). These changes were identified as early as 2 hours posttransfection and did not increase further during 12 hours of analysis, indicating that the mitochondrial dysfunction was maximal and occurred as early as plasma membrane permeability and cell death (FIG. 6A).

Inhibition of PT Pore Opening Prevents Mitochondrial Dysfunction and Cell Death

Figure 10C:
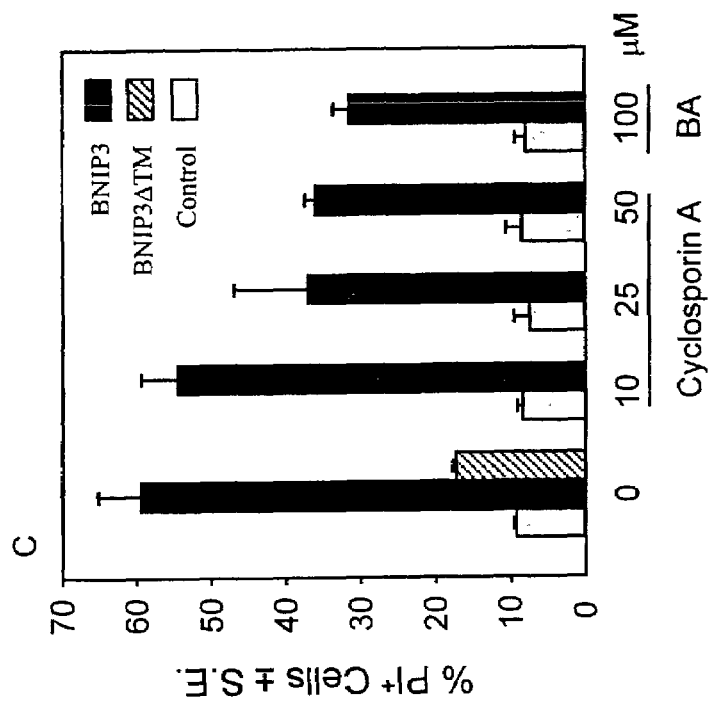
Figure 10D:
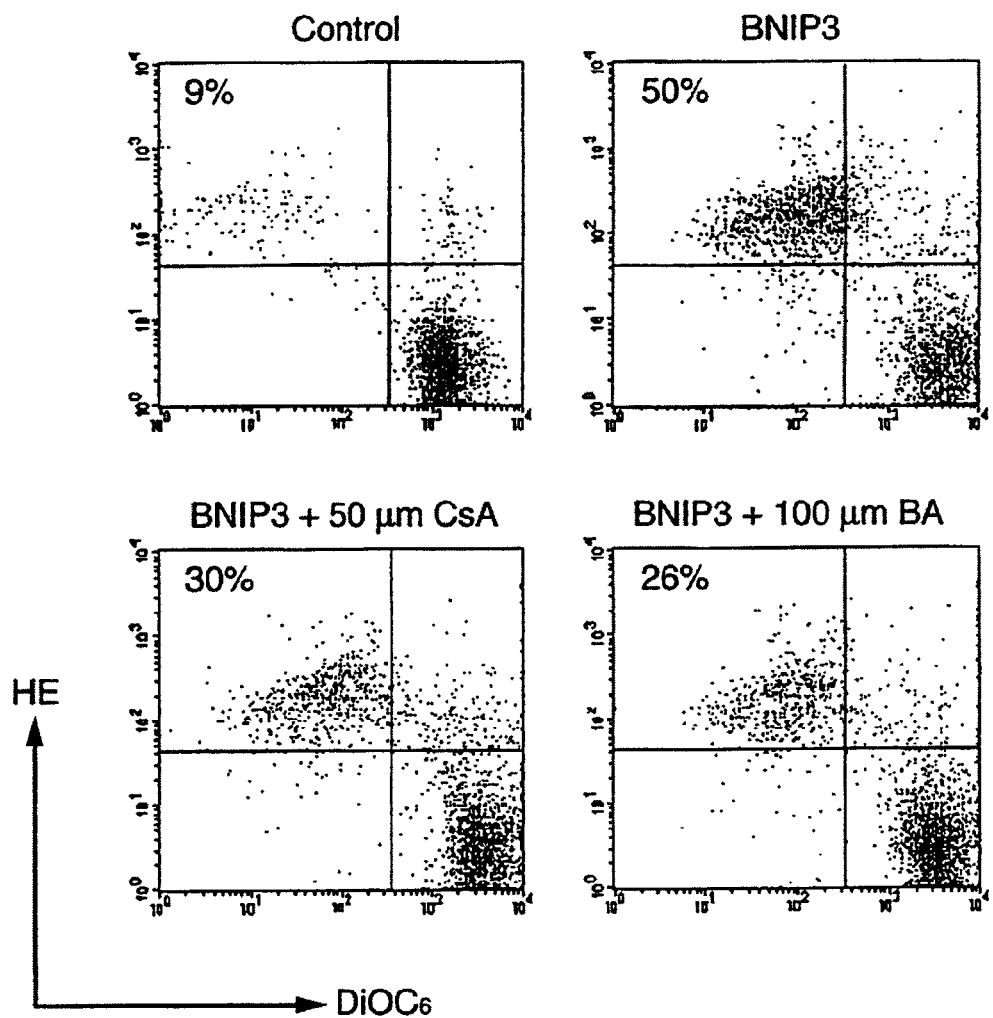
Figure 10E:
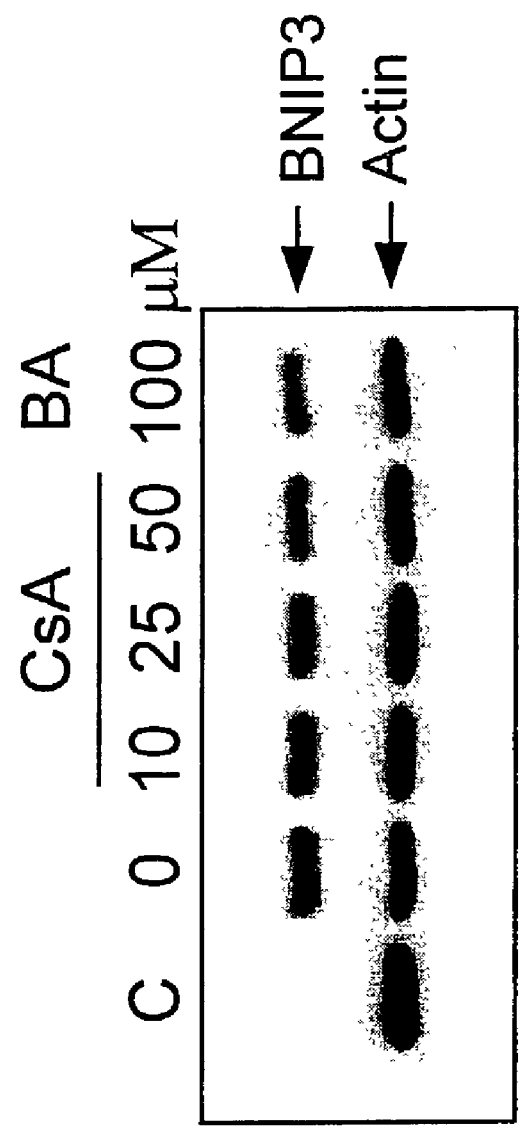

To confirm that the loss of Dcm, increase in ROS production, and the ensuing cell death were the result of opening of the PT pore, the effect of PT pore inhibitors on BNIP3-induced cell death and mitochondrial deregulation was examined using the potentiometric fluorescent probe DiOC6 in combination with HE. BNIP3-expressing cells showed 55% DiOC6-low and HE-high cells as detected in the upper left quadrant of FIG. 10D, consistent with previous experiments using JC-1, while BNIP3DTM-transfected cells were not affected compared to untreated controls. As noted earlier, opening of the PT pore can be inhibited by cyclosporin A, which interacts with cyclophilin D, or bongkrekic acid, which binds to the ANT. Treatment of BNIP3 transfectants with either cyclosporin A or bongkrekic acid revealed a dose-dependent reversal in Dcm suppression, ROS generation, and cell death (PI staining) (FIG. 10A to D). Maximum suppression was about 50% of that in control cells. Cells were treated with the drugs for 2 hours and washed prior to transfection, a procedure that did not affect BNIP3 expression in the 293T cells (FIG. 10E). Addition of either drug during the transfection suppressed BNIP3 expression. The drugs did not affect mitochondrial function and cell death when added after the transfection. BNIP3 physically interacts with Bcl-2 (Boyd, J. M. et al, 1994, Chen, G. et al, 1997), and Bcl-2 and Bcl-XL overexpression can partly suppress BNIP3-induced cell death, although this is overcome at high BNIP3 expression levels (Chen, G. et al, 1999, Chen, G. et al, 1997). The effect of Bcl-2 on BNIP3-induced cell death as measured by PI staining was examined and a reduction in plasma membrane damage in Bcl-2-expressing cells was found (FIG. 10F).

Referring specifically to the figures, FIG. 1 shows BNIP3 expression and integration into the mitochondrial membrane. FIG. 1A, in the left panel shows mitochondrion-enriched heavy membrane (HM) and S-100 cytosol (S-100) subcellular fractions of mouse tissues were isolated and alkali extracted as described in Materials and Methods, then Western blotted with polyclonal anti-BNIP3 antibody. BNIP3 lanes are lysates of 293T cells transfected with BNIP3. Right panel:HeLa cells were fractionated as described above, and fractions were Western blotted with monoclonal anti-BNIP3 antibody Ana40. Nonspecific staining was evaluated by adding GST-hBNIP3 to a parallel incubation mixture. FIG. 1B shows that subcellular fractions of hBNIP3-T7-transfected 293T (top) and MCF-7 (middle) cells were alkali extracted and blotted with mouse monoclonal anti-BNIP3 Ana40 antibody. Mouse skeletal muscle tissue prepared in the same manner was blotted for BCL-XL (bottom). FIG. 1C shows mitochondrial heavy membrane fractions from hBNIP3-T7-transfected 293T cells were trypsin digested and/or alkali extracted, as described in Materials and Methods, and blotted with either Ana40 mouse monoclonal anti-hBNIP3 or anti-T7 antibodies. Arrows indicate specific antibody reactive bands at 40, 18, and 8 kDa. P, heavy membrane pellet; S, S-100 supernatant.

FIG. 2 shows that the broad-spectrum caspase inhibitors Ac-zVAD-fmk and baculovirus p35 fail to inhibit BNIP3-induced cell death. FIG. 2A shows that 293T cells were transiently cotransfected with the reporter plasmid pcDNA3-bgal and either BNIP3-T7 (F) or inactive mutant BNIP3DTM-T7. Cells transfected with tBID-FLAG (n) or caspase 9-His6 plus Apaf-1 served as positive controls. All groups were treated with increasing concentrations of Ac-zVAD-fmk. FIG. 2B shows that in a parallel experiment, 293T cells were transfected as above with increasing concentrations of pcDNA1-p35. At 27 hours posttransfection, cells were fixed, stained, and evaluated for dead cells as described in Materials and Methods. The data represent one of three independent experiments with similar results.

Additionally, FIG. 3 shows that BNIP3 does not activate caspases. FIG. 3A shows that BNIP3 expression does not activate a DEVDase. Lysates from 293T cells transfected with BNIP3-T7, BNIP3DTM-T7, or BID-FLAG were harvested at 1, 12, 18, 24, and 36 hours and then incubated with the substrate DEVD-PNA in the presence (solid bars) or absence (shaded bars) of 500 nM Ac-DEVD-fmk. Fold activation was determined as the ratio of transfected cells to untransfected controls. Results are expressed as the mean 6 standard error (SE) from at least three independent experiments. FIG. 3B shows that BNIP3 expression fails to activate PARP cleavage. Lysates from BNIP3-T7-, BNIP3DTM-T7-, or BAX-transfected 293T cells were harvested at 12, 24, 36, and 48 hours posttransfection and immunoblotted with mouse monoclonal anti-PARP antibody. Arrows indicate the unprocessed p116 and processed p85 bands. FIG. 3C shows that BNIP3 expression fails to activate procaspase 3 processing. Lysates from BNIP3-T7-, BNIP3DTM-T7-, or BAX-transfected 293T cells were harvested 24 hours posttransfection and immunoblotted with mouse monoclonal anti-procaspase 3 antibody. The arrow indicates the unprocessed p32 band. Lane C is the untreated control.

FIG. 4 shows that BNIP3 does not induce mitochondrial cytochrome c release. More specifically, FIG. 4A shows 293T cells transiently transfected with BNIP3-T7, BNIP3DTM-T7, or BID-FLAG were stained with monoclonal anti-cytochrome c antibody and Cy3-labeled anti-mouse IgG antibody then evaluated by fluorescent microscopy. Time course of cytochrome c release and apoptosis following BNIP3-T7 ("), BNIP3DTM-T7 (n), or BID-FLAG (F) transfection of 293T (left panels) and MCF-7 (right panels) cells is shown. Cytochrome c release was scored as the loss of cytoplasmic granular staining. Apoptotic cells were scored based on chromatin condensation following Hoechst staining. The data from three independent experiments are shown as the mean 6 SE for each time point. FIG. 4B shows Western blot analysis of the time course of release of cytochrome c from mitochondria into S-100 cytosol. Aliquots of 5 mg of heavy membrane (HM) and S100 fractions from 293T cells transiently transfected with BNIP3, BNIP3DTM, or tBID were harvested at 18, 24, and 36 hours posttransfection and Western blotted with mouse anti-cytochrome c antibody (p16). The same membrane was blotted with mouse antiactin antibody (p43) to demonstrate equal loading. Control, untransfected cells.

FIG. 5 shows BNIP3-induced cell death in the absence of Apaf-1, caspase 9, or caspase 3. FIG. 5A shows wild-type, Apaf-1 2/2, caspase 9 2/2, and caspase 3 2/2 MEFs were transiently cotransfected with pcDNA3-bgal vector alone, BNIP3-T7, or BNIP3DTM-T7 and then scored for dead cells as described in Materials and Methods. Results are expressed as the mean 6 SE from three independent experiments. FIG. 5B shows that the same cell aliquots of wild-type (WT), Apaf-1 2/2, caspase 9 2/2 (Casp 9 2/2), and caspase 3 2/2 (Casp 3 2/2) MEFs used for the experiments in panel A were transfected with pcDNA3-bgal and treated with medium or with 3 mg of adriamycin per ml for 24 hours, and dead cells were enumerated in three experiments. N, N-Dimethyl formamide (DMF) was used to dilute the adriamycin.

FIG. 6 shows that BNIP3 induces rapid plasma membrane permeability but not PS externalization. FIG. 6A shows untransfected and BNIP3-T7-transfected 293T cells which were harvested at 2, 4, 8, and 12 hours posttransfection and stained with PI. PI 1 cells are expressed as the mean 6 SE of three or four experiments for each time point. FIG. 6B shows untransfected 293T cells and 293T cells (FIG. 6C) transfected with BNIP3-T7 (BNIP3), BNIP3DTM-T7 (DTM), BID-FLAG (tBID), BAX, or caspase 9/Apaf-1 (C9/A) were harvested at 12 hours posttransfection and stained for annexin V and PI. Cells that were gated as PS 1 PI 2 are expressed as the mean 6 SE of three independent experiments.

FIG. 7 shows BNIP3-induced cell death is characterized by late DNA fragmentation. FIG. 7A shows the quantification of TUNEL-positive 293T cells transiently transfected with BNIP3-T7, BNIP3DTM-T7, or BID-FLAG and stained at 18, 24, and 36 hours. Values for BNIP3-and tBID-transfected cells were significantly higher than those for controls at all time points (P, 0.01). FIG. 7B shows an illustration of transfected cells as in panel A harvested 24 hours posttransfection and stained with the TUNEL reagent (right) or Hoechst dye (left). FIG. 7C shows cells which were transfected as in panel A in the absence (open bars) or presence of 50 mM Ac-FA-fmk (solid bars) or 50 mM Ac-zVAD-fmk (hatched bars). Cells were TUNEL stained 24 hours posttransfection, and the percent positive was scored by fluorescent microscopy.

Figure 8:
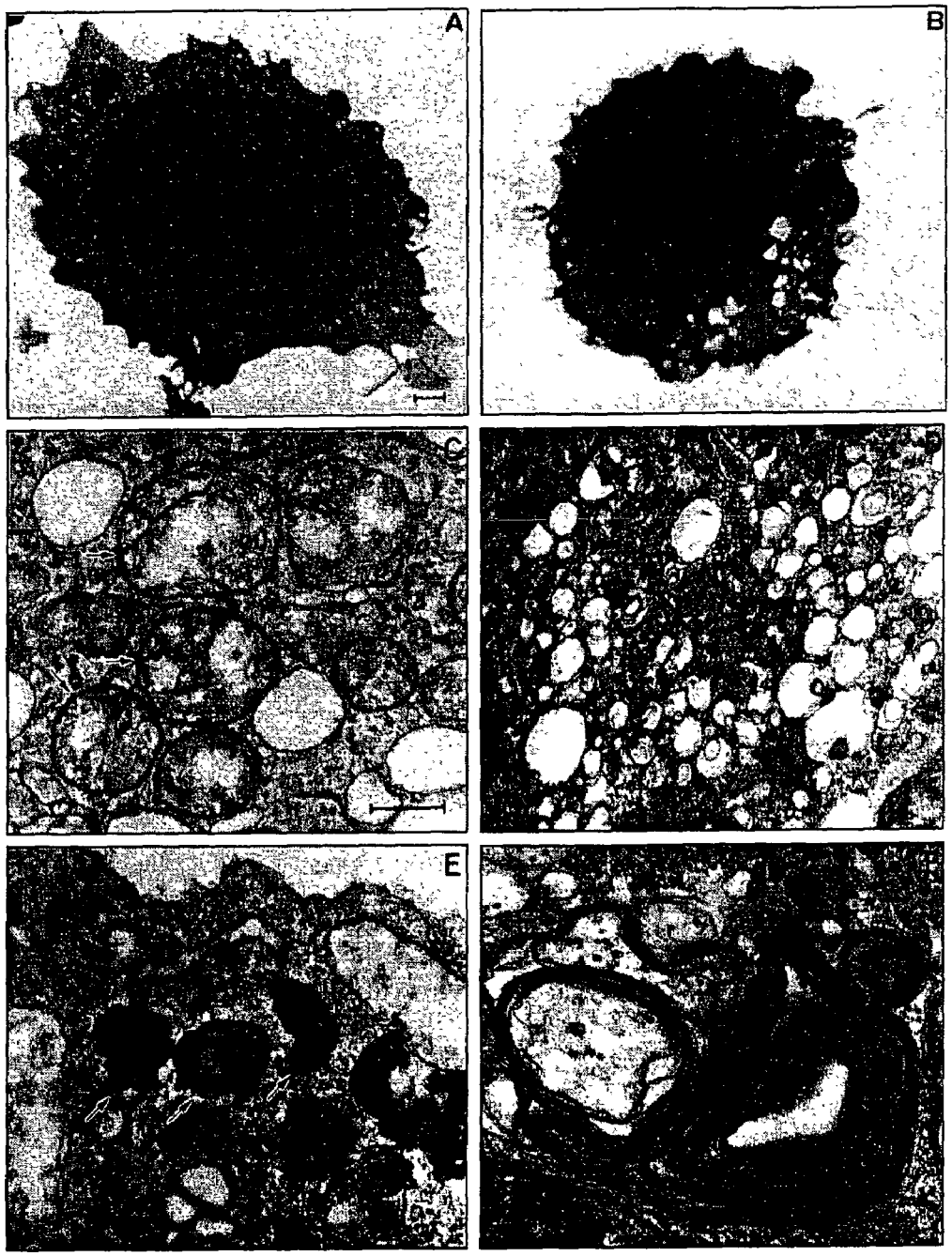
FIGS. 8A through F are photographs showing BNIP3 induces the ultrastructural changes of necrosis.

FIG. 8 shows that BNIP3 induces ultrastructural changes of necrosis. Normal 293T cells (FIG. 8A) and BNIP3-expressing 293T cells (FIGS. 8B to F) were examined 24 hours posttransfection by transmission electron microscopy. Nuclei of BNIP3-expressing cells exhibited dispersed foci of chromatin condensation and heterochromatin (FIG. 8B) compared to control cells (FIG. 8A). High-power magnifications of BNIP3 transfectants showed rounded mitochondria with disrupted internal structures (arrows) (FIG. 8C), extensive cytoplasmic vacuolation (FIG. 8D), autophagosomes (arrows) (FIG. 8E), and autophagic vacuoles containing membranous whorls (FIG. 8F). (FIGS. 8A and B), bar, 1 mm; (FIGS. 8C to F) bar, 0.5 mm.

Figure 9A:
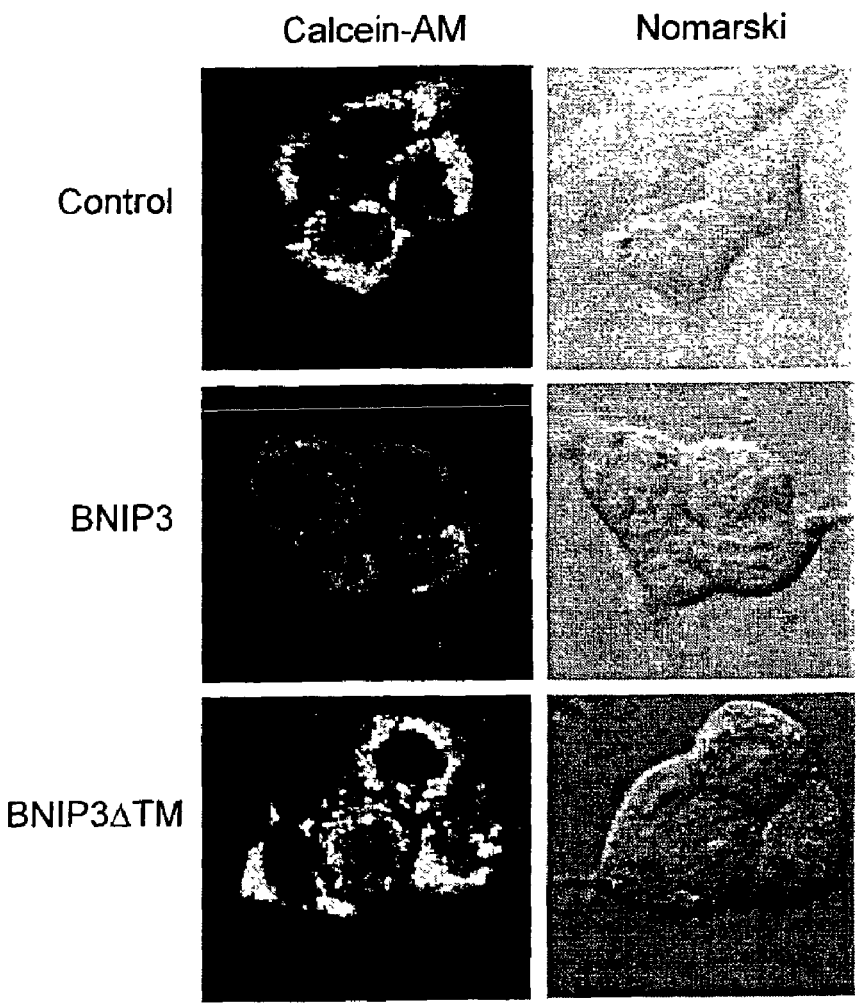
Figure 9B:
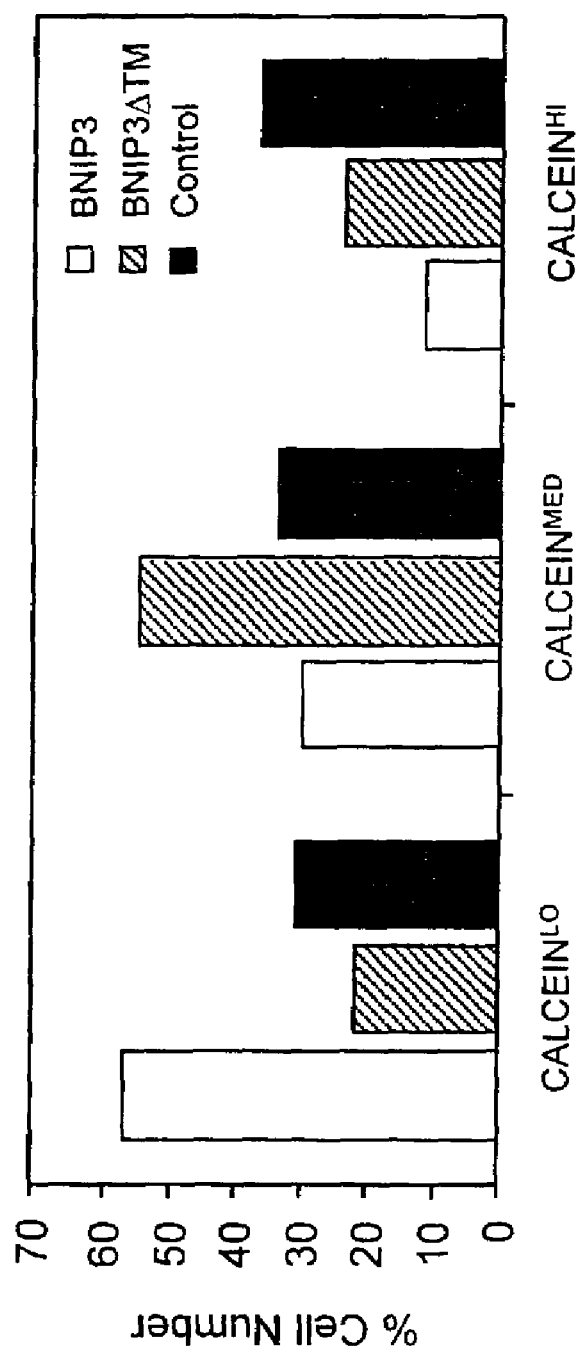
Figure 9E:
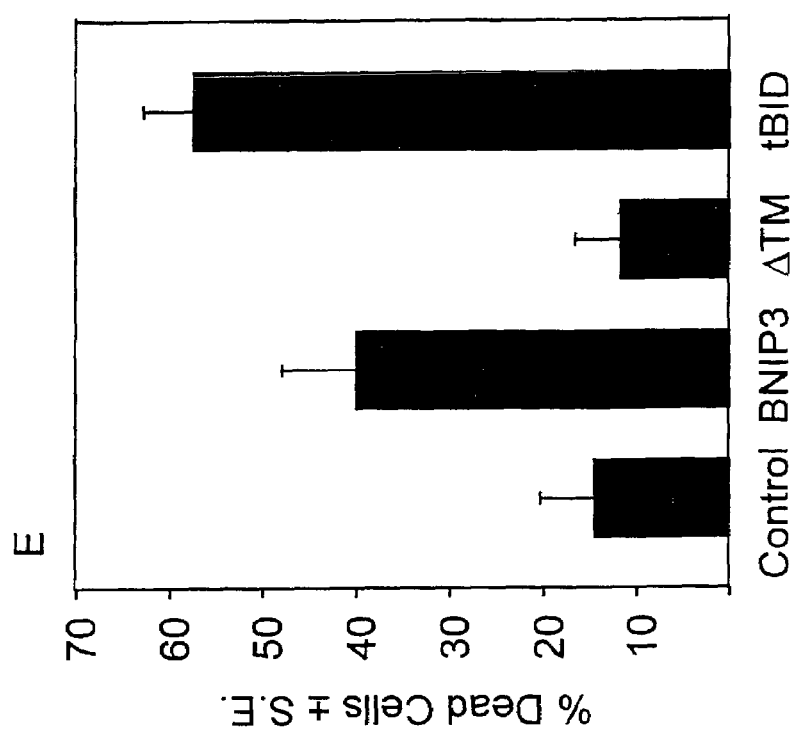

FIG. 9 shows that BNIP3-induced cell death is characterized by mitochondrial dysfunction. FIG. 9A shows the untransfected (control), BNIP3-T7 (BNIP3)-and BNIP3DTM-T7 (BNIP3DTM)-transfected 293T cells were harvested 24 hours after transfection and incubated with calcein-AM in the presence of CoCl2 to quench cytoplasmic fluorescence. Cells were visualized by confocal laser microscopy (left) and Nomarski optics (right). FIG. 9B shows the quantitation of calcein fluorescence of cells transfected as described for panel A. The percentages of cells measured as low (CALCIN LO), intermediate (CALCIN MED), or high (CALCEIN HI) total fluorescence units per cell are shown. The experiment was repeated with similar results. By chi analysis, P, 0.001 for the comparison of control versus BNIP3 and BNIP3DTM versus BNIP3. FIG. 9C shows the untransfected (control) and BNIP3-T7 (BNIP3)-, BNIP3DTM-T7 (DTM)-, or BID-FLAG (tBID) transfected 293T cells were harvested at 24 hours, stained with JC-1, and analyzed by flow cytometry as a measure of Dcm. JC-1 LO cells were defined as cells that were gated within the same range as those treated with 50 mMCICCP (99%). BNIP3- and tBID-but not BNIP3DTM-transfected cells were significantly suppressed compared to controls (P, 0.01). FIG. 9D shows cells treated as in panel C were stained with HE to measure ROS production. HE HI cells were defined as cells that were gated within the same range as those treated with 30% H2 02 for 15 minutes (98%). Levels in BNIP3-and tBID-expressing cells were significantly increased compared to untreated controls or BNIP3DTM (P, 0.03; the Student t test). FIG. 9E shows samples from the control and each of the transfections in panel C were trypan blue stained as a measure of cell death. BNIP3-and tBID-transfected cells were significantly increased compared to untreated controls or BNIP3DTM (P, 0.01; the Student t test).

FIG. 10 shows the inhibition of BNIP3-induced mitochondrial dysfunction and cell death by PT pore inhibitors and Bcl-2. Untransfected (control) and BNIP3-T7-transfected 293T cells harvested 8 hours posttransfection were treated with increasing doses of cyclosporin A or 100 mM bongkrekic acid (BA) and stained with DiOC6 (FIG. 9A), HE (FIG. 9B), or PI (FIG. 9C) as described above. BNIP3DTM-T7-transfected 293T cells were used as a negative transfection control. Results are expressed as the mean 6 SE for at least three independent experiments. FIG. 9D shows the flow cytometric histograms of HE and DiOC6 staining of BNIP3-transfected cells treated with 50 mM cyclosporin A (CsA) or 100 mM bongkrekic acid (BA). FIG. 9E shows the Western blot of BNIP3-transfected cells treated as described above using anti-T7 epitope antibody. Antiactin antibody was used as a loading control. Suppression of DiOC6 levels in BNIP3 cells was significantly inhibited compared to BNIP3 cells at 25 mM (P, 0.05) and 50 mM (P, 0.02) cyclosporin A and 100 mM bongkrekic acid (P, 0.02). Increase in HE fluorescence was inhibited at 25 mM (P, 0.03) and 50 mM (P, 0.02) cyclosporin A and 100 mM bongkrekic acid (P, 0.02). Cell death was significantly suppressed at 50 mM cyclosporin A (P, 0.02), and 100 mM bongkrekic acid (P, 0.02). (F) BNIP3-induced cell death (solid bars) in 293T cells and 293 cells overexpressing BCL-2 (BCL-2) compared to the inactive BNIP3DTM mutant (open bars). Eight hours following BNIP3 transfection, cells were stained with PI and evaluated by flow cytometry. The percent dead cells were calculated as the proportion of cells that were PI positive. Equivalent transfection efficiency was obtained in both cell lines, as detected by immunostaining.

Figure 11:
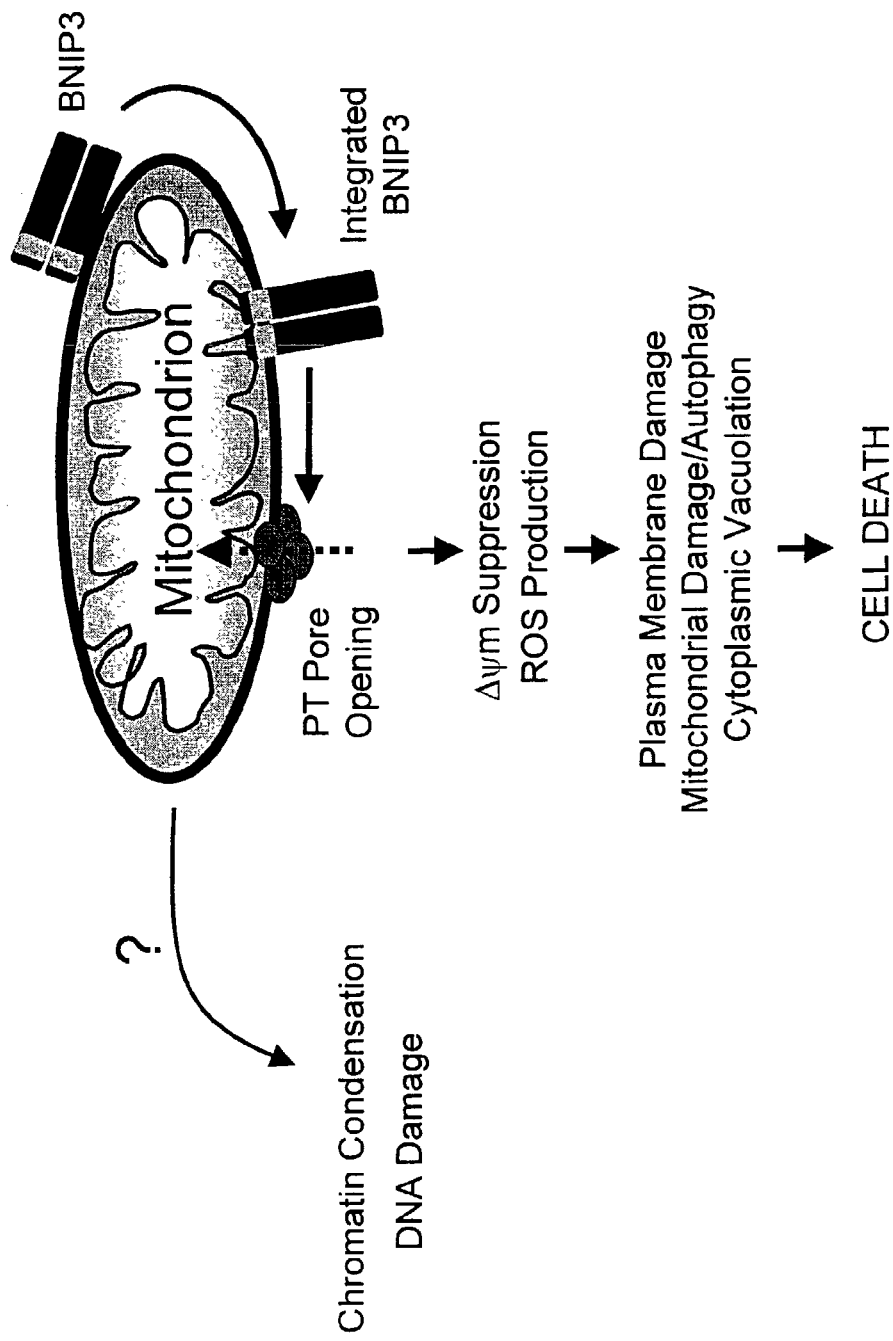
FIG. 11 shows a model of BNIP3 induced cell death.
Figure 12:
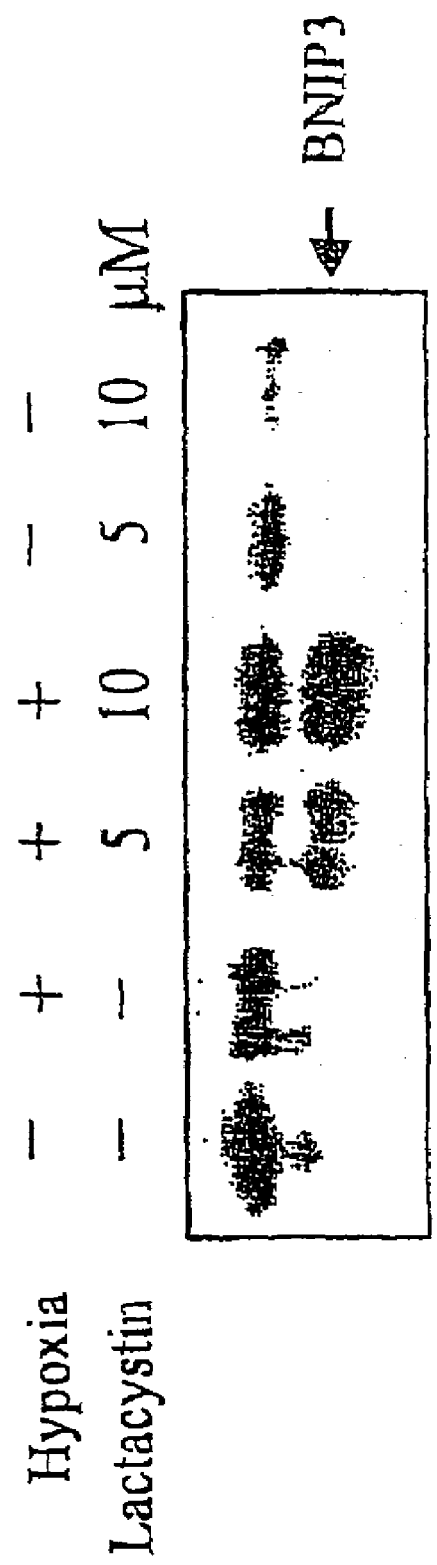
FIG. 12 shows BNIP3 protein expression in hypoxic or normoxic conditions. Neonatal cardiac myocytes were incubated in hypoxic (+) or normoxic (−) conditions for 24 hours. Cells were treated with lactacystin at the indicated concentrations and lysates harvested for western blotting with anti-BNIP3 antibody. BNIP3 band is indicated with an arrow. Lactacystin slows the degradation of the BNIP3 protein and allows its detection by western blot.
Figure 13:
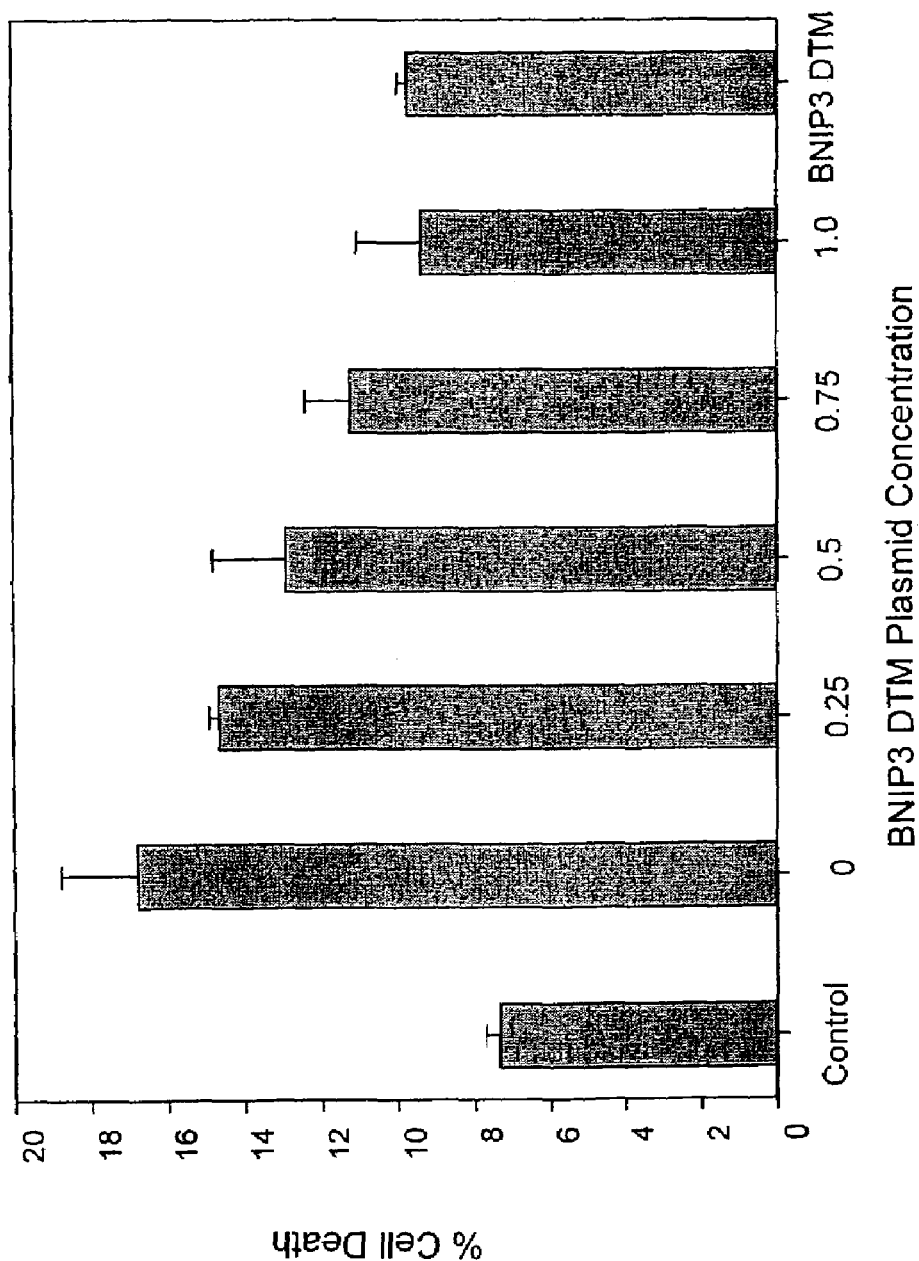
FIG. 13 is a graph showing that BNIP3 induced cell death is inhibited by the inactive BNIP3 deletion mutant, BNIP3 DTM. Increasing concentrations of BNIP3 DTM plasmid (0.25 to 1.0 μg) were added to a constant amount of BNIP3 (1.0 μg). Cell death was determined by exclusion of propidium iodide. BNIP3 DTM was able to suppress the cell death induced by BNIP3 to background levels at a 1.0 to 1.0 μg plasmid ratio. The BNIP3 DTM mutant contains amino acids 1-163, which is a deletion of the C-terminus of the protein that contains the transmembrane domain.

Finally, FIG. 11 shows a model of BNIP3-induced cell death. Overexpression permits integration of BNIP3 into the outer mitochondrial membrane in an Ncyto-Cin orientation through its TM domain. BNIP3 then initiates permeability transition pore opening and Dcm suppression with increased ROS production in an undefined sequence, leading to cell death. Late DNA fragmentation and chromatin condensation are also induced as a consequence of BNIP3 integration via an unidentified pathway.

Discussion

In the present study, it was determined that BNIP3 is capable of activating a novel form of cell death resembling necrosis as a consequence of mitochondrial PT pore opening. This mechanism is independent of caspases and the Apaf-1/cytochrome c mitochondrial pathway and occurs before the appearance of nuclear damage.

The mitochondrial membrane integration of many proapoptotic BCL-2 family members induces mitochondrial dysfunction, which plays an important role in the cell death pathway. One of the key events in apoptosis is the release of cytochrome c, which functions with dATP as a cofactor for Apaf-1 activation of the caspase cascade (Green, D. R. et al, 1998). There are currently three proposed models to explain the mechanism of cytochrome c release: (i) PT pore-induced mitochondrial swelling and subsequent outer membrane rupture (Wyllie, A. H., et al., 1980); (ii) cytochrome c exit from the mitochondria through the PT pore (Susin, S. A., et al., 1999a); and (iii) an undefined cytochrome c-specific channel in the mitochondrial outer membrane (Kluck, R. M. et al., 1999). In one model, the PT pore is hypothesized to serve as a conduit for cytochrome c release into the cytoplasm. This is supported by experiments that show a direct interaction between BAX and components of the PT pore, including ANT (Marzo, I. et al, Science 1998) and VDAC/porin (Narita, M. et al, 1998), and evidence that BAX can open the pore sufficiently to allow cytochrome c release (Susin, S. A., et al., 1999a). In contrast to BAX, BNIP3 does not induce cytochrome c release despite evidence of rapid PT pore opening. Therefore, a model in which opening of the PT pore is sufficient to release cytochrome c is not supported by the data. BAX must have other effects on mitochondrial membrane proteins to account for the difference with BNIP3. Although BNIP3 kills without cytochrome c release, it has been observed that the BNIP3 homolog NIX/BNIP3L/ BNIP3a/B5 recombinant protein induces cytochrome c release from isolated mitochondria (Imazu, T. et al, 1999). The reason for this difference from BNIP3 is not known, but there are clear structural differences between the proteins that can account for this effect.

Another mechanism for cytochrome c release occurs as a result of nonselective PT pore-induced mitochondrial matrix swelling and outer membrane rupture (Wyllie, A. H., et al., 1980). Although electron micrographs of BNIP3-transfected 293T cells show mitochondrial rounding and destruction of cristae, the large-amplitude swelling seen during growth factor withdrawal in interleukin-3dependent FL5.12 cells or Fas-treated Jurkat cells were not observed (Wyllie, A. H., et al., 1980). It is therefor established that cytochrome c release and PT pore opening can be completely separated during BNIP3-induced cell death and thus are independent events in the cell death program.

The absence of mitochondrial cytochrome c release does not exclude the activation of a caspase-dependent apoptotic pathway. For example, two different death pathways have been described in Fas-induced apoptosis, one of which leads to direct activation of caspase 3 through receptor-activated caspase 8 and does not require cytochrome c, and a second that requires mitochondrial release of cytochrome c to activate caspase 3 and apoptosis (Susin, S. A., et al., 1999). BNIP3, on the other hand, requires neither Apaf-1/cytochrome c nor the downstream caspases, as BNIP3-induced cell death was unaffected by broad-spectrum caspase inhibitors and was fully functional in MEF cell lines deficient in Apaf-1, caspase 9, or caspase 3. Thus, BNIP3-induced cell death is primarily caspase independent. Induction of caspase-independent cell death has been increasingly observed, and examples include the adenoviral protein E40RF4 (Lavoie, J. et al., 1998) and cellular proteins PML (Scaffidi, C., et al., 1998), anti-CD2 (Deas, O. et al, 1998), oncogenic Ras (Chi, S. et al, 1999), and FADD (Kawahara, A. et al, 1998). Furthermore, BAX and BAK are able to induce cell death, as opposed to the nuclear changes of apoptosis, in the presence of the general caspase inhibitor Ac-zVAD-fmk (McCarthy, N. J. et al, 1997,59). Although cell death can be caspase independent, DNA fragmentation and chromatin condensation following most apoptotic signals require downstream caspases (Earnshaw, W. C. et al, 1999). Nuclei in BNIP3 transfectants exhibit DNA fragmentation and focal chromatin condensation, although these nuclear changes are preceded by loss of plasma membrane integrity, and thus the cells are likely already committed to die. Nevertheless, it is unclear how the nuclear changes are mediated, as there is only minimal DEVDase activation, even at the late time points. Furthermore, DNA fragmentation is only partially inhibited by AczVAD-fmk Immunofluorescence and immunoblotting of subcellular fractions exclude the participation of AIF, a caspase-independent mediator (Tsujimoto, Y. 1997), as it was not translocated from the mitochondria to the nucleus in BNIP3-transfected cells. Ultrastructural analysis of BNIP3-transfected cells revealed that the nuclei have a peculiar mottled appearance, with dispersed foci of chromatin condensation rather than the global large-scale condensation normally observed in caspase-dependent apoptosis.

BNIP3 transfectants exhibit a rapid loss in plasma membrane integrity, and this precedes the appearance of DNA fragmentation detected by TUNEL. In contrast, cells expressing tBID, BAX, and caspase 9/Apaf-1 showed both the expected apoptotic phenotype of an intact plasma membrane and PS externalization (PS 1 PI 2) as well as some cells with rapid plasma membrane disruption. This observation suggests that the primary cause of BNIP3-induced cell death is the loss of membrane integrity, which would be more typical of a necrotic type of cell death. Electron micrograph analysis of BNIP3-transfected cells supports this interpretation. The morphological changes show extensive cytoplasmic vacuolation and mitochondrial deformation with minimal nuclear damage. Similar vacuole formation has been observed in caspase-independent forms of cell death, including anti-CD2 treated cells (Deas, O. et al, 1998), neuronal cells subjected to nerve growth factor withdrawal (Yasuda, M., et al., 1998), and Ac-zVAD-fmk-treated BAX and BAK transfectants (McCarthy, N. J. et al, 1997). BNIP3-expressing cells contain a heterogeneous population of electron-dense and electronlucent vacuoles, some of which appear to be autophagic and are very similar to the structures recently observed in sympathetic neurons after nerve growth factor withdrawal (Yasuda, M., et al., 1998). In this study, autophagic degeneration and vacuole formation were blocked by treatment with an autophagy inhibitor, 3-methyladenine, but not the caspase inhibitor Ac-zVAD-fmk, and can be similar to BNIP3-induced cell death. BNIP3-mediated cell death also resembles the caspase-and Apaf-1-independent cell death in the interdigital spaces of mouse limb buds, including mottled nuclei and cytoplasmic vacuolation (Chautan, M. et al, 1999). A morphologically similar form of caspase-independent cell death has been reported in the slime mold *Dictyostelium discoideum*, which was also inhibitable by cyclosporin A (Quignon, F., et al., 1998).

Opening of the PT pore, loss of Dcm, and increased ROS production are important contributors to cellular destruction (63) and are early events in both apoptosis and necrosis (Crompton, M. 1999, Kroemer, G. et al, 1998). PT pore opening has also been described in several models of apoptotic cell death as an amplification step that is secondary to initial caspase activation (Bossy-Wetzel, E. et al, 1998, Finucane, D. M. et al, 1999, Marzo, I. et al, 1998). As noted earlier, necrotic cell death is similarly characterized by rapid PT pore opening that can be inhibited by cyclosporin A, which also effectively blocks cell death (Kroemer, G. et al, 1998). BNIP3-induces PT pore opening with Dcm suppression and ROS production occurs concurrently with plasma membrane permeabilization and is blocked by the PT pore specific inhibitors cyclosporin A and bongkrekic acid. Thus, PT pore opening is a pivotal event for BNIP3-induced cell death. This is summarized in FIG. 11. In earlier studies, there remains a controversy as to the sequence of mitochondrial events in cell death. Zamzami et al. (63) demonstrated that ROS were generated only after dissipation of Dcm following dexamethasone treatment of splenic T cells. The loss of mitochondrial membrane potential and ROS production can be both an inducer and a consequence of PT pore opening depending on the death signal (Crompton, M. 1999, Kroemer, G. et al, 1997). Considering the mechanism by which BNIP3 affects the PT pore, it interacts either directly or indirectly with components of the pore, resulting in its opening. Alternatively, BNIP3 targets another protein that suppresses transmembrane potential and induces ROS production, which secondarily opens the PT pore. Thus, although PT pore opening is a key mechanism that mediates BNIP3-induced cell death, the specific mitochondrial proteins that are targeted remain to be identified. Based on the observed function of BNIP3 as a mediator of cell death resembling necrosis when overexpressed, it is reasonable to postulate that some forms of necrotic cell death can be mediated by endogenous BNIP3.

Recently, increased endogenous BNIP3 mRNA and protein expression has been observed in HeLa cells grown in hypoxic conditions (K. Guo, G. Searfoss, C. Franks, M. Pagnoni, D. Krolikowsky, K. T. Yu, M. Jaye, K. Clark, and Y. Ivashchenko, Proceedings of the AACR Special Conference on Programmed Cell Death Regulation, abstract A-56,2000). Hypoxia is a well-known inducer of necrotic cell death (Crompton, M. 1999). Thus, it is interesting to speculate that BNIP3 plays a role in mediating death associated with hypoxic stress and possibly other forms of necrotic cell death. Endogenous BNIP3 protein is abundant in murine and human skeletal muscle and is not detectable in lysates of all other nonskeletal musclebearing tissues and over 15 cell lines, including myoblasts and differentiated myocytes (D. Dubik and A. H. Greenberg, unpublished data). However, it was found that some (e. g., HeLa, 293T, and K562) but not all (e. g., MCF-7) cell lines have small amounts of BNIP3 protein detectable in enriched mitochondrial fractions. Endogenous muscle BNIP3 is alkali extractable and thus loosely associated and not integrated into the mitochondrial membrane, similar to the observations for endogenous BAX intracellular localization by Goping et al. (Goping, I. S. et al, 1998). When overexpressed, BNIP3 (and BAX) integrates into the mitochondrial membrane through the C-terminal transmembrane domain (amino acids 164 to 184) with the orientation of the protein in an Ncyto-Cin direction. A 17- to 18-kDa portion of the C terminus is detected after trypsin digestion of mitochondria. This would be consistent with a dimer of two trypsin-resistant fragments of 8.5 to 9.0 kDa from approximately amino acids 104 to 194. The Ana40 monoclonal reacts with amino acids 112 to 124, and this epitope is present in the trypsin-resistant fragment. The question remains how the endogenous BNIP3 remains in an inactive, nonintegrated state. At least two non-mutually exclusive mechanisms are possible: (i) endogenous BNIP3 assumes a conformation that prevents integration of the TM domain until it is altered by some posttranslational modification, or (ii) endogenous BNIP3 interacts with a regulatory protein that maintains it in an unintegrated form at the surface of the mitochondria until it dissociates. Since overexpression induces cell death, BNIP3 is able to overcome this inhibition in high concentrations, suggesting that the regulatory mechanism is saturable. Translocation from the cytoplasm to the mitochondria during induction of apoptosis has been reported for several members of the BCL-2 proapoptotic family, including BID (Li, H. et al, 1998, Luo, X. et al, 1998), BAX (Goping, I. S. et al, 1998), BAK (Griffiths, G. J. et al, 1999), BAD (Datta, S. R. et al, 1997,64), and BIM (Salvesen, G. S., et al., 1999). These molecules can be regulated by phosphorylation, dimerization, or proteolytic cleavage (Gross, A. et al, 1999). In the absence of an apoptotic stimulus, BAD is phosphorylated by Akt (64) and by mitochondrion-anchored protein kinase A (Harada, H. et al, 1999) and sequestered in the cytoplasm by 14-3-3 protein (64). BAX, BAK, and BIM are held inactive in the cytoplasm and are translocated to the mitochondria after a cell death signal. Further regulation is suspected for BAX, which is permitted to integrate into the mitochondrial membrane following proteolytic cleavage of an inhibitory element in the N terminus (Goping, I. S. et al, 1998). Similarly, BID is cleaved by caspase 8 following Fas ligation, resulting in mitochondrial translocation (Li, H. et al, 1998, Luo, X. et al, 1998). Whether endogenous BNIP3 translocation to the mitochondrial membrane is regulated by a posttranslational mechanism similar to these proteins remains to be determined. In conclusion, BNIP3 overexpression initiates a cell death pathway that is activated by protein integration into the outer mitochondrial membrane. This pathway requires PT pore opening and is independent of caspases, Apaf-1, and cytochrome c release. Cell death manifests as mitochondrial dysfunction, plasma membrane damage, and the morphology of necrosis.

Example 2

Neuronal cell death has been shown to occur by apoptotic, necrotic and alternative cell death mechanisms. Recently, it was reported that the gene BNIP3, a member of the Bcl-2 family without a functional BH3 domain, induces cell death in a necrotic-like manner and that this gene-regulated cell death pathway involves opening of the mitochondrial permeability transition pore without caspase activation and cytochrome c release; BNIP3-mediated cell death was induced by hypoxic challenge in non-neuronal cells. BNIP3 is a gene that when activated in brain is capable of inducing necrotic (possibly paraptotic) cell death. In rat brain, BNIP3 staining was not detectable by immunohistochemistry. However, BNIP3 expression was increased dramatically in models of brain injury and excitotoxicity. After blunt trauma to brain or intrastriatal injection of kainic acid, BNIP3 immunopositive cells were observed adjacent to the sites of injury and the BNIP3 positive cells showed DNA fragmentation as demonstrated by TUNEL and Hoechst 33342 staining. Western blot analysis showed a 30 kDa band from kainic acid injected brain; positive immunoblot was blocked by a BNIP3-GST recombinant protein. Similar results were observed using a chronic seizure model using i.p. injections of kainic acid. In situ hybridization results using a RNA riboprobe revealed that intrastriatal injections of kainic acid increased levels of BNIP3 mRNA in sites of brain injury. These results show that BNIP3 is a new target for neuronal rescue strategies.

Example 3

Neuronal cell death has been shown to occur by apoptotic, necrotic, and alternative cell death mechanisms. Recently, it was reported that BNIP3, a member of the Bcl-2 protein family without a functional BH3 domain, induces cell death in a necrotic-like manner and that this gene-regulated cell death pathway involves opening of the mitochondrial permeability transition pore without caspase activation and cytochrome c release. However, to date nothing is know about the role of BNIP3 in neuronal cell death. BNIP3, when expressed in neurons, is capable of inducing necrotic (possibly parapoptotic) cell death. Glutamate was applied to cultures of rat hippocampal neurons, expression of BNIP3 was detected using immunohistochemical techniques, and cell death was measured morphologically and by using trypan blue exclusion. BNIP3 expression following application of glutamate was both time- and glutamate concentration-dependent. Cell death was also found to be time-and concentration-dependant; increased numbers of trypan blue positive cells paralleled the increased number of cells immunopositive for BNIP3. Expression of BNIP3 was seen in those cells with morphological features associated with necrotic rather than apoptotic cell death. BNIP3 is involved in excitotoxic cell death and is a mediator of parapoptotic neuronal cell death.

Example 4

Cardiac cell death has been shown to occur by apoptotic, necrotic and alternative cell death mechanisms. Recently, it was reported that the gene BNIP3, a member of the Bcl-2 family without a functional BH3 domain, induces cell death in a necrotic-like manner and that this gene-regulated cell death pathway involves opening of the mitochondrial permeability transition pore without caspase activation and cytochrome c release; BNIP3-mediated cell death was induced during hypoxic challenge in non-cardiac cells. BNIP3 is a gene when activated in heart is capable of inducing necrotic (possibly paraptotic) cell death. In the rat heart, BNIP3 staining was not detectable by immunocytochemistry. However, BNIP3 expression was increased markedly in models of heart injury. After myocardial infarction induced by coronary artery blood flow insufficiency, BNIP3 positive staining was detected in cells in the peri-infarct zone including scar tissue and in cells adjacent to primary site of injury (necrotic core). Western Blot analysis showed monomeric and homodimeric bands at 30 kDa and 60 kDa respectively. BNIP staining cells displayed dismorphoric nuclei and DNA structure by Hoechst 33258 staining. These studies indicate that BNIP3 is a new target for cardiac cell rescue strategies.

Example 5

Cardiac cell death has been shown to occur by apoptotic, necrotic and alternative cell death mechanisms. Recently, it was reported that the gene BNIP3, a member of the Bcl-2 family without a functional BH3 domain, induces cell death in a necrotic-like manner and that this gene-regulated cell death pathway involves opening of the mitochondrial permeability transition pore without caspase activation and cytochrome c release; BNIP3-mediated cell death was induced during hypoxic challenge in non-cardiac cells. BNIP3 is a gene when activated in heart is capable of inducing necrotic (possibly paraptotic) cell death. In rat cardiac myocytes BNIP3 expression was not detectable. BNIP3 was localized to mitochondrial membrane under normoxic conditions. However, BNIP3 expression was increased dramatically in cardiac myocytes subjected to hypoxic challenge. BNIP3 protein mitochondrial and sub-cellular membrane factions. Western Blot analysis showed monomeric and homodimeric bands at 30 kDa and 60 kDa respectively. Cardiac myocyte death by Hoechst 33258 staining was increased in cells during hypoxia along with BNIP3 expression. These studies indicate that BNIP3 is a new target for cardiac cell rescue strategies.

Example 6

Cardiac cell death has been shown to occur by apoptotic, necrotic and alternative cell death mechanisms. Recently, it was reported that the gene BNIP3, a member of the Bcl-2 family without a functional BH3 domain, induces cell death in a necrotic-like manner and that this gene-regulated cell death pathway involves opening of the mitochondrial permeability transition pore without caspase activation and cytochrome c release; BNIP3-mediated cell death was induced during hypoxic challenge in non-cardiac cells. BNIP3 is a gene when activated in heart is capable of inducing necrotic (possibly paraptotic) cell death. In rat cardiac myocytes BNIP3 expression was not detectable. BNIP3 was localized to mitochondrial membrane under normoxic conditions. However, BNIP3 expression was increased dramatically in cardiac myocytes subjected to hypoxic challenge. BNIP3 protein was integrated to mitochondrial and sub-cellular membrane fractions during hypoxia. Western Blot analysis showed monomeric and homodimeric bands at 30 kDa and 60 kDa respectively. Adenovirus mediated gene transfer of a viral vector designed to express a mutant of BNIP3 (DN BNIP3 protein) was delivered to cardiac myocytes with uniformity and high efficiency. Mitochondrial defects including changes to mitochondrial membrane potential and permeability transition pore opening associated with hypoxic injury were observed in cardiac myocytes. Nuclear defects associated with changes to DNA structure were observed in hypoxic cardiac myocytes by Hoechst 33258 staining. However, mitochondrial defects in cardiac myocytes subjected to hypoxia were suppressed in cardiac myocytes genetically modified to express the DN BNIP3 protein. Nuclear defects in cardiac myocytes were suppressed in cells expressing the DN BNIP3 protein. Expression of the DN BNIP3 protein suppressed morphological features of cardiac myocyte cell death during hypoxia as determined by calcein acteoxy-methyl ester (AM) and ethidium homodimer staining. These studies indicate that BNIP3 is a mediator of apoptotic and necrotic cell death of cardiac myocytes. BNIP3 is a new target for cardiac cell rescue strategies.

Methods

Recombinant Adenovirus

The AdBNIP3 CrmA adenovirus, consisting of the wild type and mutant DN BNIP3 cDNA, was generated by homologous recombination in human embryonic 293 kidney cells, by a method that has previously been reported (Kirshenbaum, L A et al, 1993). Twenty-four hours after myocyte isolation, cells were infected in serum-free DMEM with AdCrmA virus at a titer of 20 plaque-forming units per cell for 4-6 hours. The viral suspension was removed and cells were incubated for an additional 20 hours in supplement DMEM prior to experimentation (Kirshenbaum, L A et al., 1997).

Hypoxia

Post-natal ventricular myocytes were subjected to hypoxia for 24 hours in an airtight chamber in culture media that was continually gassed with 95% $N_2$-5% $CO_2$. These conditions were modeled after preliminary studies (de Moissac, D et al., 2000; Bialik, S et al, 1999) demonstrating that this duration of hypoxia was sufficient to trigger apoptosis of neonatal ventricular myocytes.

Assays of Apoptosis

Genomic DNA was subjected to gel electrophoresis as previously reported (Bialik, S et al, 1999). Nuclear morphology was assessed by Hoechst 33258 dye (Molecular Probes, Eugene, Oreg.) as reported. Cells were visualized using a Olympus AX70 epifluorescence microscope as described previously (de Moissac, D et al., 2000).

Immunofluorescence Microscopy

Following interventions, myocytes were incubated with 0.1 µM Mito Tracker Red, (chloromethyl-rosamine CMX-Ros, Molecular Probes, Eugene, Oreg.) for the detection of intact respiring mitochondria. Fixed cells were incubated with 1 µg/ml of a murine antibody directed toward cytochrome c (Pharmingen) followed by anti-mouse conjugated fluorescein IgG (1:150) (Roche Diagnostics) and detected using an Olympus Fluoview confocal microscope.

Western Blot Analysis

For detection of BNIP3 proteins the Western Blot filter was probed with a rabbit antibody directed toward BNIP3 proteins. The cytoplasmic S-100 fraction was prepared by methods previously described (Bialik, S et al, 1999). Appropriate control experiments were employed to ensure purity and completeness of separation of mitochondrial and S100 fractions. Bound proteins were visualized using enhanced chemiluminesence (ECL) reagents (Amersham).

Mitochondrial Membrane Potential $\Delta\psi m$ and MPT

Mitochondrial membrane potential $\Delta\psi m$, was monitored using the potential sensitive dyes JC-1 dye (1 µM, 5,5',6,6'-tetraethylbenzimidazolylcarbocyanine iodide) or TMRM (50 nM, tetramethyl rhodamine methyl ester perchlorate, Molecular Probes, Eugene, Oreg.). A fluorescence distribution curve of individual cells was generated for each condition tested. Fluorescent intensities were then compared to each respective control group. To monitor mitochondrial permeability transition (PT), ventricular myocytes were loaded with 5 µM catcein-acetoxymethyiester (caicein-AM, Molecular Probes, Eugene, Oreg.) in the presence of 2-5 mM cobalt chloride to quench the cytoplasmic signal (Petronilli, V, et al., 1998).

Example 7

Materials and Methods

Reagents

Murine monoclonal anti-T7 antibody was purchased from Novagen (Madison, Wis). Anti-human and mouse BNIP3 antibodies, T7-tagged pcDNA3-BNIP3, T7-tagged pcDNA3-$BNIP3^{3-163}$ plasmids were provided by Dr. A. H. Greenberg.

Animal Model

Male Sprague-Dawley rats, with body weights ranging between 200 to 250 g, were obtained from the University of Manitoba Central Animal Care breeding facility. All procedures followed Canadian Council on Animal Care guidelines and were approved by the Animal Care Committee at the University of Manitoba. Animals were anesthetized with 74 mg/kg sodium pentobarbital (i.p.) and placed in a stereotaxic surgery frame. Unilateral intrastriatal injections were performed using the following coordinates (in mm); AP 9.0, ML 3.0 and DV 4.5 (Paxinos, G. et al. (1986)). Drugs were administered over a 5 minute period in a volume of 1 µl using a 10 µl syringe fitted with a 30-gauge needle. Following injection, the needle was left in place for 5 minutes before being slowly withdrawn to allow diffusion of the drug away from the injection site. Kainic acid, dissolved in 50 mM Tris-HCl with the pH adjusted to 7.4 with NaOH, was administered at a dose of 2.5 nmol. Control rats received unilateral injections of 1 µl 50 mM Tris-HCl, pH 7.4. To confirm the role of kainate receptors, the receptor antagonist CNQX (dissolved in 0.1 N NaOH with volumes adjusted with 50 mM Tris-HCl pH 7.4) was administered at a dose of 5 nmol in a volume of 1 µl by itself or in combination with 2.5 nmol kainic acid. Following injection, wounds were sutured and animals were allowed to recover for periods up to 5 days. From pilot studies, the inventors found BNIP3 expression to be increased from 24 hours to 5 days after kainic acid injection (data not included). In the present study, all animals were killed 48 hours after intrastriatal injections.

Cell Culture

Primary hippocampal neurons were prepared from 18-day-old embryonic Sprague-Dawley rats as described previously by Haughey, N. J. et al. (2001). Briefly, hippocampal tissue was dissociated by gentle tituration in a calcium-free Hank's balanced salt solution and was centrifuged at 1000×g. Cells were resuspended in Dulbecco's modified Eagle's medium (DMEM)/F12 nutrient mixture containing 10% heat-inactivated fetal bovine serum and 1% antibiotic solution (104 IU of penicillin G/ml, 10 mg streptomycin/ml and 25 µg amphotericin B/ml) in 0.9% NaCl (Sigma, St Louis, Mo., USA). Hippocampal neurons were plated at a density of $2 \times 10^5$ cells/ml on 12-mm diameter poly d-lysine-coated glass coverslips. Three hours after plating, the media was replaced with serum-free Neurobasal media containing 1% B-27 supplement (Gibco, Rockville, Md., USA). Immunofluorescent staining for microtubule-associated protein-2 (MAP-2) on neurons and glial fibrillary acidic protein (GFAP) in astrocytes showed that cultures were >98% neurons; the remainder of cells were predominantly astrocytes.

Pharmacological Studies

To determine the extent to which NMDA-type glutamate receptors were involved in BNIP3 expression and excitotoxic cell death, the inventors used the agonist NMDA (100 µM) in the absence or presence of the NMDA receptor antagonist MK-801 (10 µM). To determine the extent to which caspase activation contributes to BNIP3-mediated cell death, hippocampal cells were incubated in the absence or presence of the broad spectrum cell permeable caspase inhibitors z-VAD-FMK (50 µM) and BOC-D-FMK (50 µM); these inhibitors were applied 30 minutes prior to application of glutamate or NMDA. To determine the role of protein translation in glutamate-mediated toxicity, actinomycin D (1.0 µg/ml) was used.

Cell Transfections

Transfection of cells was performed on day four in culture with LipofectAMINE 2000 (Roche) according to manufacturer's protocol. Cells were transfected with a pcDNA3-BNIP3 plasmid encoding the full length of BNIP3 and a pcDNA3-BNIP3-163 plasmid that encodes a truncated form (the first 163 amino acids) of BNIP3 that lacks the functional transmembrane domain. Cells were used after 9 days in culture for excitotoxicity experiments. Neuronal cell death was assessed using trypan blue exclusion, morphological changes, and Hoescht 33342 staining. Morphological characteristics were examined on a Nikon Eclipse TE200 microscope and fluorescence was examined on a Zeiss Axioskop 2.

Immunohistochemistry and in situ Hybridization

For immunohistochemistry and in situ hybridization, rats were perfused transcardially with 0.9% saline and then 4% paraformaldehyde. Brains were carefully removed and post-fixed overnight in PBS containing 4% paraformaldehyde. After rinsing in PBS, the brains were placed in PBS containing 0.5 M sucrose (pH 7.3) at 4° C. until buoyancy was lost. Eight mm sections were cut on a cryostat (Shandon) and mounted on silane treated slides. Frozen brain sections cut from KA-injected and control rats were blocked and permeabilized with PBS containing 2% BSA, 5% normal goat serum, and 0.3% Triton X-100 for 30 minutes at room temperature. The sections were then incubated overnight at 4° C. with a polyclonal antibody against BNIP3 (1:200) followed by rhodamine-conjugated goat anti-rabbit (1:200, Jackson ImmunoResearch Laboratories Inc., West Grove, Pa.) for 2 hours at room temperature. The anti-BNIP3 polyclonal antibody recognizes both human and rat BNIP3 and was used as well to detect BNIP3 expression in primary rat hippocampal neurons after exposure to glutamate and NMDA. A monoclonal anti-T7 antibody (1:200) that recognizes the T7 epitope tag of pcDNA3 plasmid was used to determine transfection efficiency. For detection of BNIP3 expression in primary hippocampal neurons after plasmid transfection, a monoclonal BNIP3 antibody that is specific for human BNIP3 was used. Fluorescent pictures were taken on a Zeiss (Thornwood, N.Y.) microscope equipped with an AxioCam digital camera (Carl Zeiss, Jena, Germany). For in situ hybridization, an RNA probe (specific for BNIP3) was synthesized using a DIG RNA labeling kit (Roche) according to manufacturer's protocol. Brain sections were hybridized with the probe, incubated with an alkaline phosphatase-conjugated anti-digoxigenin antibody, and labeled cells were detected with BCIP/NBT.

Detection of Cell Death

In vitro cell death was estimated using trypan blue exclusion. Cells were incubated in 0.4% trypan blue solution for 30 minutes and then counted on a bright-field microscope. Non-viable cells were distinguished by their dark blue staining. To examine nuclear morphology, nuclear DNA was stained with Hoescht 33342. DNA fragmentation was detected by TUNEL using an in situ cell death detection kit with fluorescein. Statistical analyses were by ANOVA with Tukey's post-test.

Western Blots

For immunoblotting assays, samples were prepared from rat brains or from cultured cells. Rats were killed by decapitation, brains were rapidly removed and striata were dissected out, frozen rapidly on dry ice, and stored at −80° C. Protein concentration was determined by the Bradford method with bovine serum albumin as standard. Protein samples were separated using SDS-PAGE, Tris-Tricine buffer, and transferred to polyvinylidene difluoride membranes suitable for small molecular weight peptides. Proteins were probed with anti-BNIP3 antibody and were digitized. Controls were run in the presence of BNIP3-GST protein.

Results

Figure 15:
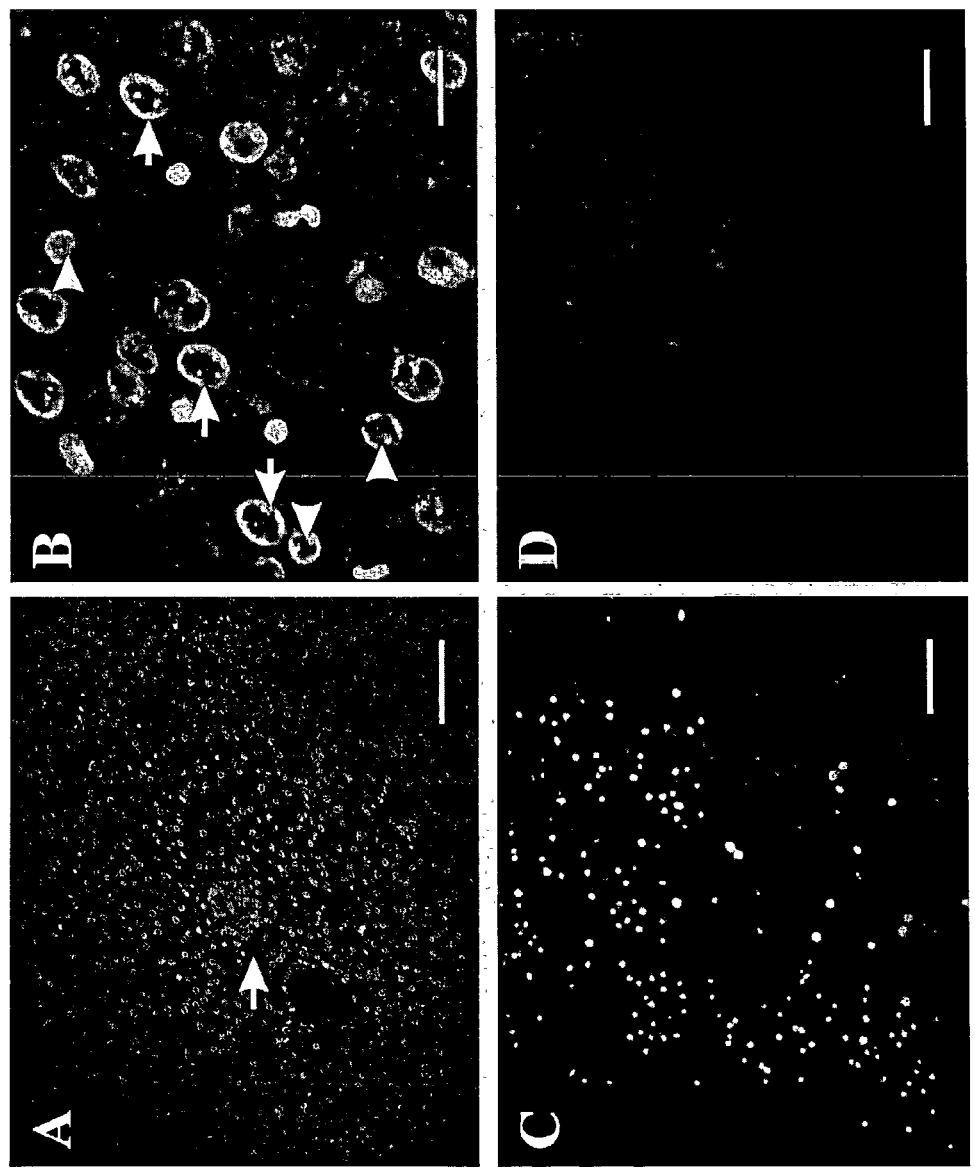
FIG. 15 shows that BNIP3 expression in brain increased with excitotoxicity and correlated with measures of cell death. A. BNIP3 immunopositive neurons were present adjacent to sites of kainic acid injection. Arrow points to site of injection. B. DNA fragmentation was observed in BNIP3-immunopositive neurons (arrows). BNIP3-immunonegative neurons showed normal nuclear morphology (arrow heads). C. TUNEL-positive nuclei, surrounded sites of kainic acid injection. D. TUNEL-positive neurons were not detected in normal brain. Scale bars: A.=500 μm, B.=50 μm, C. and D.=200 μm.

Under control conditions, the inventors were able to only barely detect BNIP3 in brain tissue or hippocampal neurons. As a first step to testing the hypothesis that BNIP3 expression plays an important role in neuronal cell death, the inventors examined levels of BNIP3 expression by immunohistochemistry in brains of rats injected intrastriatally with kainic acid. Two days after unilateral injection of kainic acid, BNIP3 immunopositive neurons were present in striatal areas adjacent to the site of injection (FIG. 15A). High levels of BNIP3 immunostaining were found in the cytoplasm of striatal neurons affected by the kainic acid, and almost all the BNIP3 positive neurons showed signs of DNA damage when stained with Hoescht 33342 (FIG. 15B). BNIP3-immunonegative neurons showed normal nuclear morphology. DNA fragmentation in kainic acid-induced neuronal cell death was confirmed further by TUNEL labeling with TUNEL positive nuclei being detected only in areas adjacent to sites of kainic acid injection and not in contralateral striatum (FIG. 15C, D). To confirm that the increased expression of BNIP3 by kainic acid was due to activation of kainate receptors, brain tissue was processed from rats that received intrastriatal injections (1 µl) of 2.5 nmol kainic acid, 5 nmol CNQX, a mixture of 5 nmol CNQX and 2.5 nmol KA, or 50 mM Tris-HCl pH 7.4. BNIP3 expression was observed only in those rats that received kainic acid alone and not in those rats receiving CNQX or buffer (data not shown).

Figure 16:
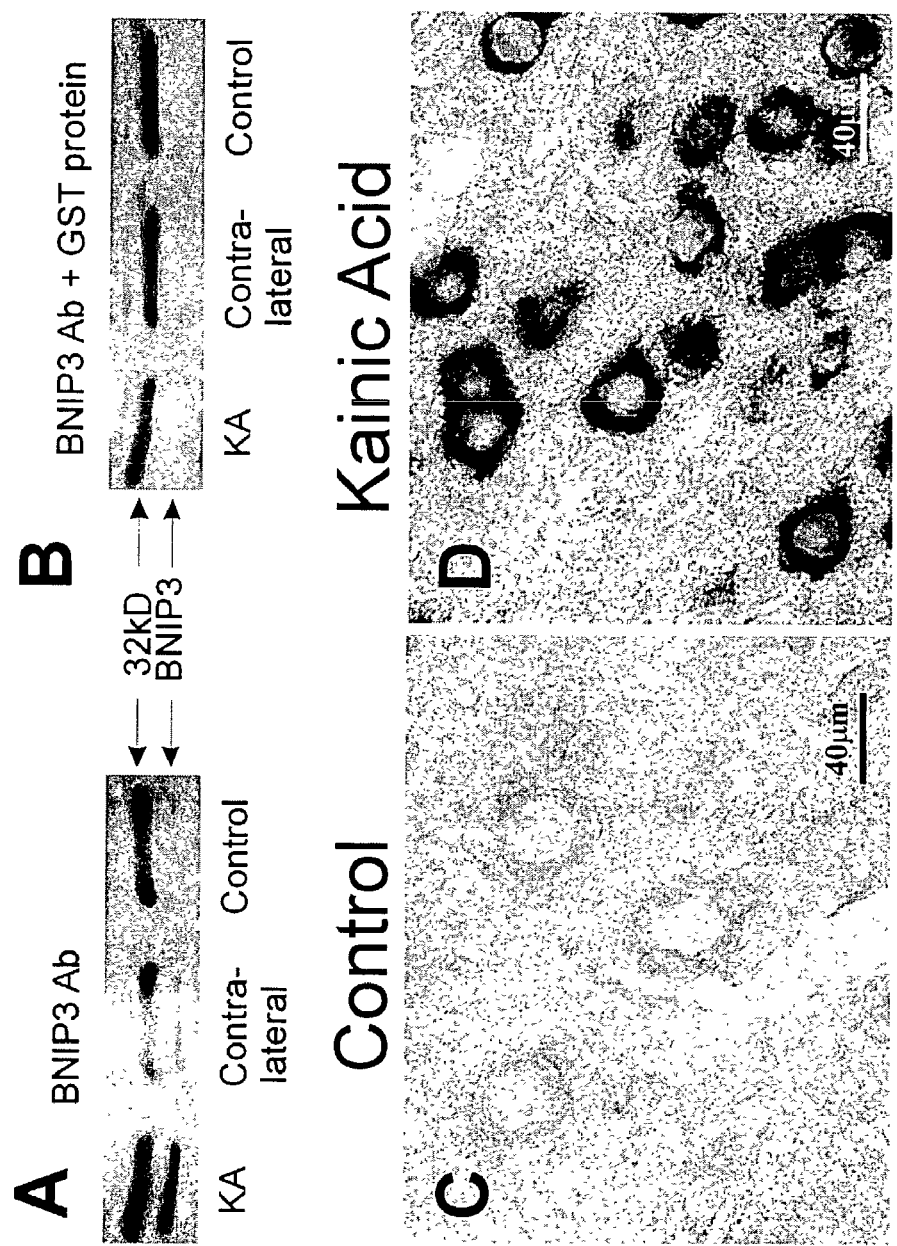
FIG. 16 shows that BNIP3 mRNA and protein levels increased with excitotoxicity. A. Immunoblot for BNIP3 demonstrated increased levels of BNIP3 in kainic acid-injected striatum as compared to uninjected contralateral striatum and normal control rats. B. Immunopositive blotting for BNIP3 was completely absent when BNIP3 antibody was first incubated with BNIP3-GST protein. C. Levels of BNIP3 mRNA as demonstrated by in situ hybridization were very low in uninjected contralateral rat striatum. D. Levels of BNIP3 mRNA were increased dramatically following kainic acid injections.

To more quantitatively determine the levels of BNIP3 and determine the molecular mass of the BNIP3 expressed, immunoblots were run for samples derived from kainic acid-injected striata, contralateral uninjected striata, Tris-HCl-injected striata and contralateral uninjected striata from Tris-HCl injected rats. A 30 kD band was present in kainic acid-injected striata (FIG. 16A); this band was much weaker in contralateral striata and was absent in samples from Tris-HCl injected rats. To demonstrate the specificity of the BNIP3 immunoblotting, control experiments were run where the BNIP3 antibody was first incubated for 30 minutes with a BNIP3-GST protein. As shown in FIG. 16B, immunoblotting for BNIP3 was completely blocked by the BNIP3-GST protein. A nonspecific 32 kD band was detected in all the striatal samples.

To determine whether kainic acid increased BNIP3 transcriptionally as well as translationally as described above, brain samples from kainic acid injected rats were processed by in situ hybridization with an RNA probe specific for BNIP3. Levels of BNIP3 mRNA were increased by kainic acid (FIGS. 16C and D). Positive hybridization signals were found in a group of striatal neurons adjacent to the site of KA injection whereas neurons in other brain areas showed very low levels of BNIP3 mRNA.

To determine mechanisms by which BNIP3 expression induced by excitotoxicity kills neurons, primary cultures of rat hippocampal neurons were treated with glutamate for 6 hours, maintained in Neurobasal media for 24 hours, and stained with trypan blue for membrane integrity. Glutamate increased neuronal cell death in a dose-dependent manner (FIG. 17A); 70% of cells stained positively for trypan blue with 100 µM glutamate, and 10 µM glutamate killed 40% of hippocampal neurons. Expression of BNIP3 was not detectable in the majority of untreated neurons and less than 15% of the untreated neurons expressed low levels of BNIP3 by immunohistochemistry (FIG. 17B). In contrast, more than 50% of cells treated with 100 µM glutamate stained positive for BNIP3 (FIG. 17C). Nuclei in BNIP3 positive neurons showed a characteristic dysmorphic appearance (FIG. 17D).

Next the inventors determined the extent to which BNIP3 expression was necessary and sufficient to kill neurons. Primary cultures of hippocampal neurons at day 4 in culture were transfected using LipofectAMINE 2000 with a pcDNA3-BNIP3 plasmid encoding full length BNIP3, a pcDNA3-BNIP3$^{3-163}$ encoding the first 163 amino acids of BNIP3, or the empty pcDNA3 plasmid. The transfection efficiency was about 20% based on immunohistochemistry using an anti-T7 antibody that recognizes the T7 epitope tag. Transient transfection with pcDNA3-BNIP3 but not pcDNA3-BNIP3$^{3-163}$ (truncated BNIP3) plasmid resulted in DNA condensation and neuronal cell death (FIG. 18). The truncated BNIP3 was diffusely distributed in the cytoplasm due to the lack of its transmembrane domain (FIG. 18B) whereas the full length BNIP3 showed a pattern of punctuate localization (FIG. 18A) resembling that of mitochondria. Neuronal survival rates after 5 days of transfection with BNIP3 plasmid were decreased (P=0.065) compared to cells transfected with pcDNA3-BNIP3$^{3-163}$ or the pcDNA3 plasmids (FIG. 18C). In neurons expressing full length BNIP3, 81% showed DNA condensation (FIG. 18D). In contrast, DNA damage was observed in only 24% of BNIP3-positive neurons transfected with the pcDNA3-BNIP3$^{3-163}$ plasmid. To determine if the truncated form of BNIP3 was capable of preventing neuronal cell death, the inventors exposed transfected cells to glutamate (100 µM) at day 9 in culture (5 days after transfection). As shown in FIG. 18E, pcDNA3-BNIP3$^{3-163}$ transfection significantly increased neuronal survival (p<0.001); 68% of neurons survived glutamate toxicity compared to 42% of cells transfected with vehicle plasmid. Expression of full length BNIP3 increased glutamate toxicity and reduced cell survival rates to 32%.

Figure 19:
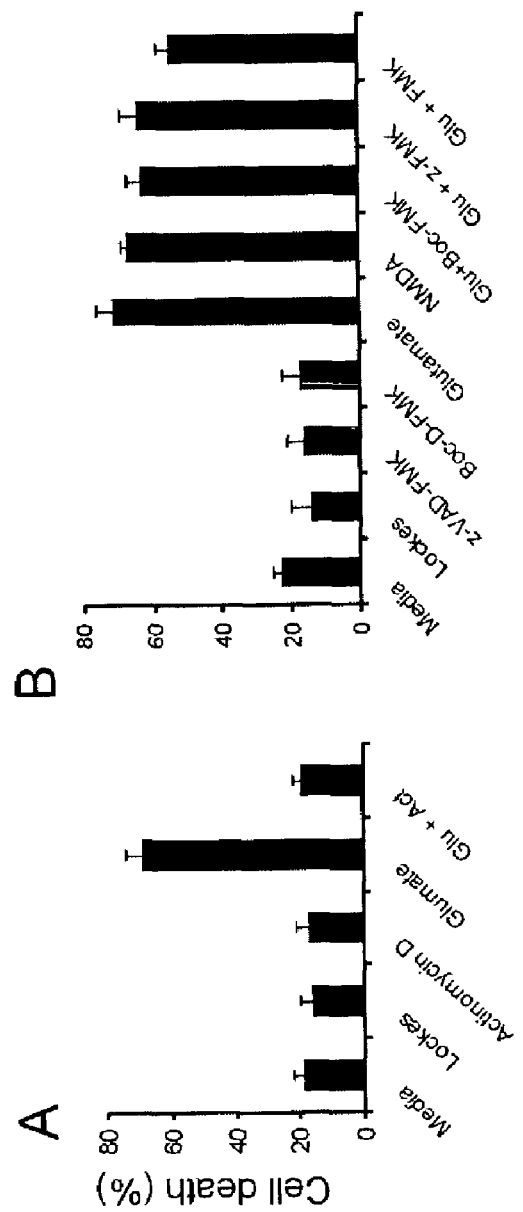
FIG. 19 shows that BNIP3-induced neuronal cell death in excitotoxicity required protein synthesis but was largely independent of caspase activity. A. Actinomycin D significantly decreased the number of trypan blue positive cells ($p<0.01$) caused by glutamate toxicity to untreated control levels. B. Inhibition of caspase activity did not prevent cell death caused by glutamate or NMDA. z-VAD-FMK alone did not prevent cell death caused by the excitotoxic toxins. Co-application of z-VAD-FMK and BOC-D-FMK resulted in a small but statistically significant decrease of cell death ($P=0.045$).

To determine if BNIP3-mediated cell death pathway in excitotoxicity involved protein synthesis, the inventors evaluated the effectiveness of the RNA synthesis inhibitor actinomycin D (1 mg/ml) in preventing excitatory neuronal cell death. As shown in FIG. 19A, addition of actinomycin D significantly decreased the number of trypan blue positive cells (p<0.01) caused by glutamate toxicity to untreated control levels whereas actinomycin D alone did not affect cell death rates.

The inventors next examined caspase involvement in BNIP3-mediated neuronal cell death. Primary hippocampal neurons were pre-incubated with z-VAD-FMK (50 µM) alone or in combination with BOC-D-FMK (50 mM); both are potent cell permeable caspase inhibitors. Cell viability was determined by trypan blue exclusion 6 hours after application of glutamate or NMDA. NMDA and glutamate significantly increased neuronal cell death (p<0.01). z-VAD-FMK alone did not prevent cell death caused by glutamate or NMDA. Co-application of z-VAD-FMK and BOC-D-FMK resulted in a small but statistically significant decrease of cell death (p=0.045) (FIG. 19B).

Discussion

Excitotoxicity is a form of neuronal cell death that has been associated with a variety of neurodegenerative disorders including stroke, Alzheimer's disease, Parkinson's disease, and spinal cord and traumatic brain injury.

Previously, it was completely unclear whether and which molecular regulators might control atypical neuronal cell death resulting from excitotoxicity. The present inventors demonstrate for the first time that BNIP3 levels increased dramatically in in vivo and in vitro models of excitotoxicity, that overexpression of full length BNIP3 decreased the viability of hippocampal neurons grown in culture and increased significantly the susceptibility of these neurons to glutamate-induced cell death, that BNIP3-mediated cell death occurred independently of caspase activation, and that expression of a truncated (dominant negative) form of BNIP3 that lacked the functional transmembrane domain increased neuronal viability and protected neurons against glutamate-induced excitotoxicity.

Example 8

Materials and Methods

Cell Culture and Hypoxia

Ventricular myocytes were isolated from 1- to 2-day-old Sprague-Dawley rats (University of Manitoba, Winnipeg, Canada) and submitted to primary culture as reported (Kirshenbaum and Schneider, 1995). Myocytes were subjected to hypoxia for 24 hours in an air-tight chamber continually gassed with 95% $N_2$-5% $CO_2$, as previously reported (Moissac et al., 2000; Long et al., 1997; Tanaka et al., 1994). Adult rat hearts (n=3) were excised from adult rats (250 to 300 g) and subjected to global hypoxia for 1 hour on a modified Langendorff perfusion system with buffer continually gassed with 95% $N_2$-5% $CO_2$, as previously reported (Kirshenbaum, 1993). Heart failure was induced in rats by surgical ligation of the left anterior descending coronary artery, as previously reported (Dixon et al., 1992). Non-failing sham control hearts and those with heart failure were excised from animals 8 weeks after myocardial infarction. Hearts (n=3) were dissected to remove the infarcted scar tissue, and the left ventricular free wall was homogenized and analyzed by Western blot for BNIP3 expression. Animals were handled according to guidelines established by the University of Manitoba and Canadian Council on Animal Care.

Recombinant Adenovirus

The cDNAs for BNIP3 full-length (BNIP3) and carboxyl terminal transmembrane domain deletion mutant (BNIP3ΔTM) have been described previously (Vande et al., 2000). Recombinant adenoviruses encoding the full-length BNIP3 or transmembrane deletion mutant are designated AdBNIP3 or AdBNIP3ΔTM, respectively, and generated as reported previously (Kirshenbaum et al., 1993).

Cell Viability

Cell viability was determined using the vital dyes 2 μmol/L calcein acetoxymethyl ester (green) to determine the number of living cells and 2 μmol/L ethidium homodimer-1 (red) (Molecular Probes) to identify the number of dead cells (Kirshenbaum and Schneider, 1995). The number of green cells versus red cells was used to determine changes in cell viability (Moissac et al., 2000). Cells were analyzed from at least n=3 independent myocyte isolations counting ≧200 cells for each condition tested. Data are expressed as mean±SE percent reduction from control.

Western Blot Analysis

For detection of BNIP3 protein, total cardiac cell lysate was subjected to Western blot analysis using a murine antibody directed toward BNIP3 (Vande et al., 2000). To isolate mitochondria from ventricular myocytes, cells were washed in HIM buffer (200 mmol/L mannitol, 70 mmol/L sucrose, 10 mmol/L HEPES-KOH, 1 mmol/L EGTA, pH 7.5). The crude cell pellet was disrupted and resuspended in HIM buffer containing 2.0% wt/vol bovine serum albumin. The homogenate was ultracentrifuged to obtain the mitochondrial fraction and resuspended in 200 mmol/L sucrose, 10 mmol/L HEPES-KOH, 1 mmol/L ATP, 5 mmol/L sodium succinate, 0.08 mmol/L ADP, and 2 mmol/L $K_2HPO_4$. To assess whether BNIP3 integrates into mitochondrial membranes during hypoxia, mitochondria were subjected to alkali extraction using 0.01 mol/L $Na_2CO_3$ (pH 11.5); this will dissociate and solubilize proteins that are not membrane integrated (Vande et al, 2000; Goping et al, 1998). Antibodies directed toward the following Bcl-2 family members were obtained from respective suppliers: Bad (Transduction Laboratories Inc), Bax (Santa Cruz Inc), and Bak and Bcl-2 (Pharmingen). Bound proteins were visualized using enhanced chemiluminescence (ECL) reagents (Amersham Pharmacia Inc).

Mitochondrial Permeability Transition Pore

To monitor mitochondrial permeability transition (PT), ventricular myocytes were loaded with 5 μmol/L calcein-acetoxymethylester (calcein-AM, Molecular Probes) in the presence of 2 to 5 mmol/L cobalt chloride as previously reported (Gurevich et al., 2001; Petronilli et al., 1998).

Statistical Analysis

Multiple comparisons between groups were determined by 1-way ANOVA. Unpaired 2-tailed Student's t test was used to compare mean differences between groups. Differences were considered to be statistically significant to a level of P<0.05. In all cases, the data were obtained from at least 3 to 4 independent myocyte isolations using 3 replicates for each condition tested.

Results

Figure 20:
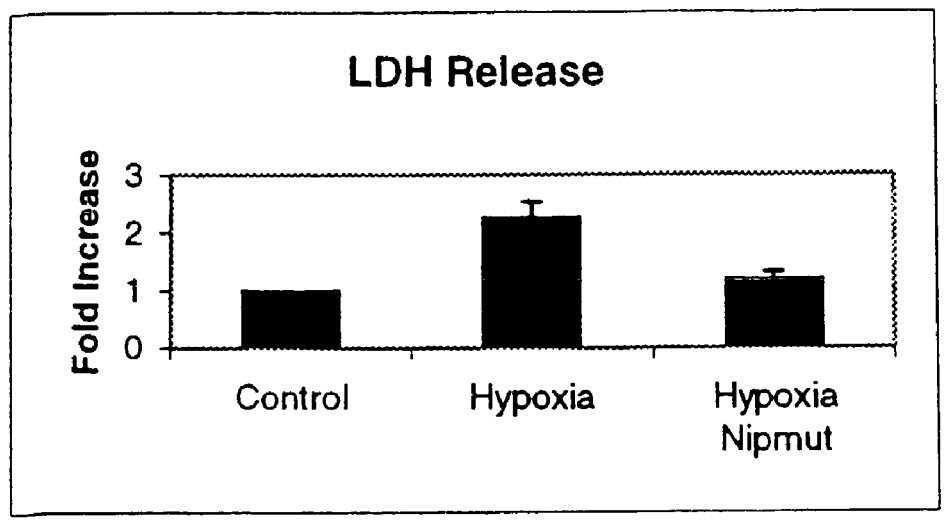
FIG. 20 is a graph showing LDH release.

In contrast to normoxic cells, cells subjected to hypoxia resulted in an increase in myocyte death. Changes to plasma membrane integrity were also observed in hypoxic cells as evidenced by a 2 fold increase in lactate dehydrogenase (LDH) release (FIG. 20).

Figure 21:
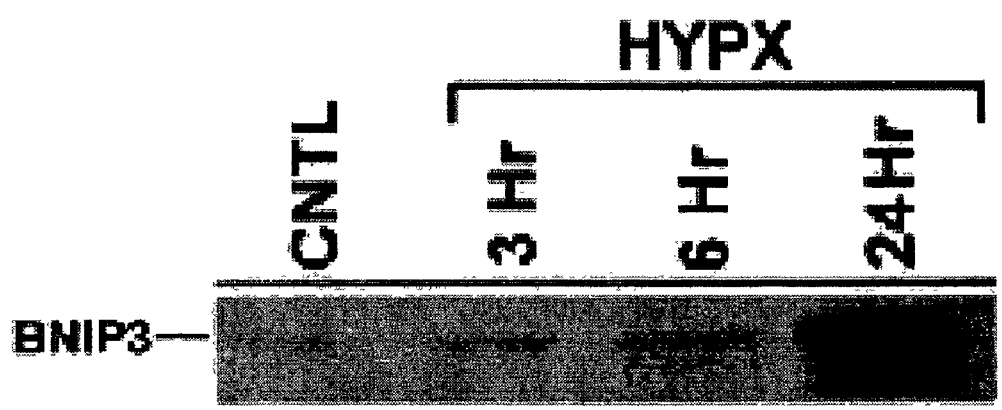
FIG. 21 shows hypoxia induces expression of BNIP3 in ventricular myocytes. Western blot analysis of cardiac cell lysate derived from normoxic and hypoxic ventricular myocytes at different time points. Densitometric scanning indicated a 19.5-fold increase ($P<0.05$) in 28-kDa BNIP3 protein expression during hypoxia compared with normoxic controls. Data were obtained from n=3 independent myocyte isolations. HYPX indicates hypoxia; CNTL, normoxic cells.
Figure 22:
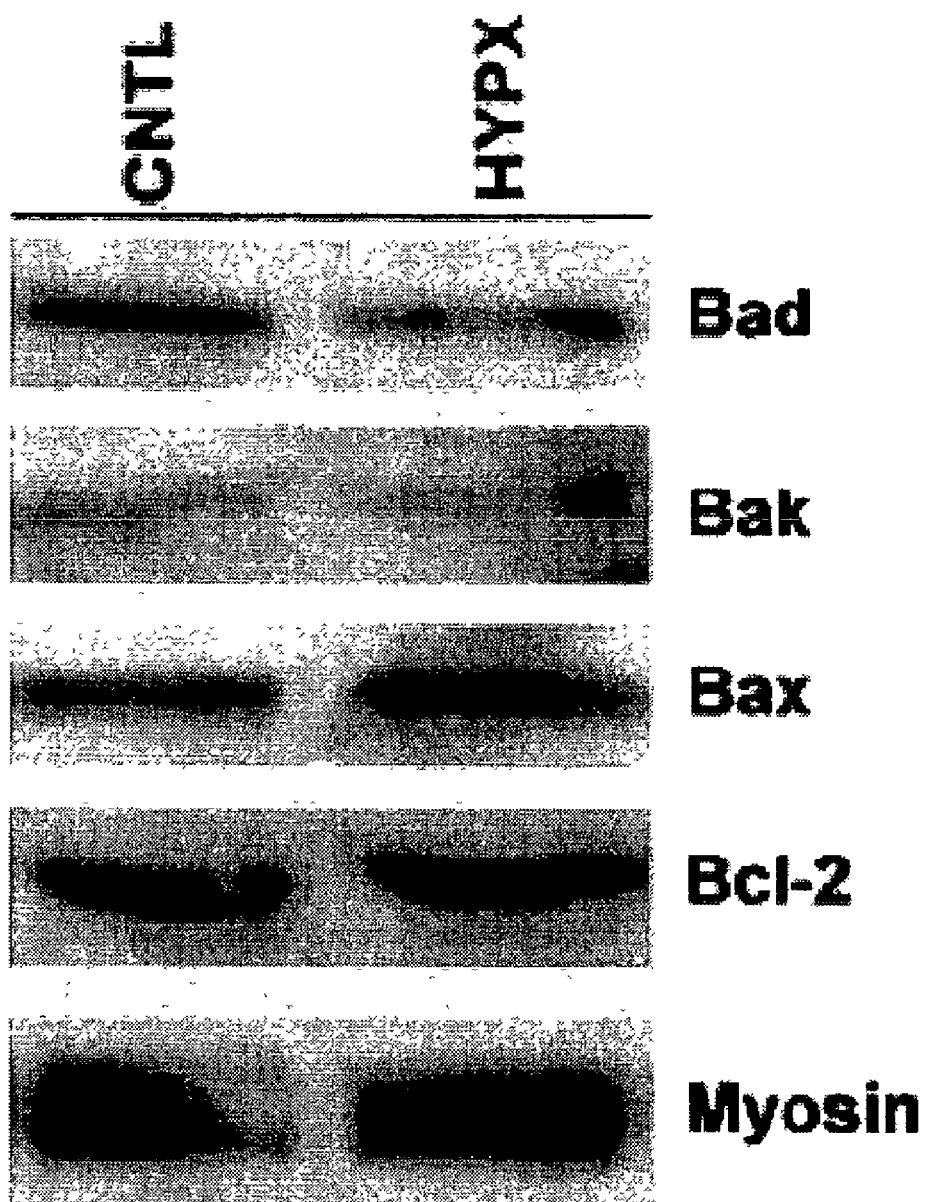
FIG. 22 shows the Western blot analysis of proapoptotic Bcl-2 family members. Western blot analysis of cardiac cell lysate derived from normoxic cells (CNTL) and cells subjected to 24 hours of hypoxia (HYPX). Filter was probed with antibodies directed toward Bcl-2 family members Bad, Bak, Bax, and Bcl-2, respectively. Bottom, Sarcomeric myosin to demonstrate equivalent protein loading.

As a step toward identifying putative regulators of cardiac cell death, the inventors ascertained whether hypoxia leads to the induction of BNIP3. As shown by Western blots analysis (FIG. 21), there was no apparent change in the expression of BNIP3 after short durations of hypoxia compared with normoxic control cells. Interestingly, a significant 19.5-fold (P<0.05) induction of BNIP3 protein expression was observed in cells subjected to hypoxia for 24 hours. The induction of BNIP3 is coincident with the occurrence of hypoxia-induced mitochondrial defects and apoptosis of ventricular myocytes at this time point. Moreover, there was no apparent change in the expression of Bad, Bak, Bax, or Bcl-2 in cells subjected to hypoxia at this time point (FIG. 22).

The inventors further investigated the involvement of BNIP3 during hypoxia-induced apoptosis of ventricular myocytes. To verify the hypoxia-induced BNIP3 was not developmentally restricted or its expression confined to the neonatal myocardium, the inventors ascertained whether BNIP3 induction occurs in the context of the adult heart under in vitro and in vivo conditions. An increase in BNIP3 expression was observed in isolated Langendorff perfused adult rat hearts subjected to global hypoxia (FIG. 23A), verifying the above BNIP3 data in neonatal ventricular myocytes. Furthermore, in contrast to normal, non-failing hearts, a significant increase in BNIP3 expression was detected in adult rat hearts with chronic heart failure after myocardial infarction in vivo (FIG. 23B). These findings indicate that induction and expression of BNIP3 is not limited to the neonatal heart and that BNIP3 may be involved in promoting cell death during hypoxic/ischemic pathologies.

Figure 25:
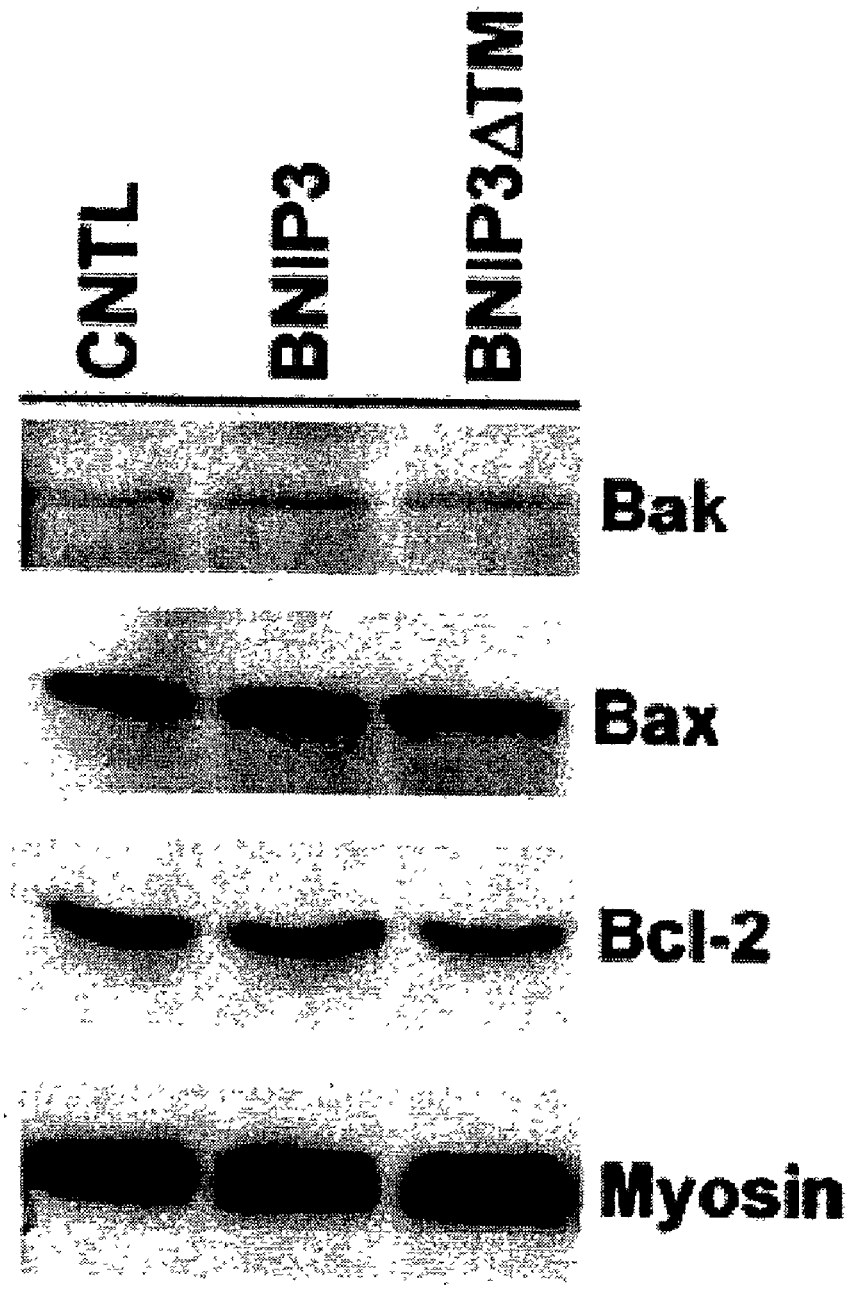
FIG. 25 shows the Western blot analysis of Bcl-2 family members. Western blot analysis of cardiac cell lysate derived from ventricular myocytes in the presence and absence of BNIP3 and BNIP3ΔTM proteins. No apparent change in the expression levels of Bak, Bax, or Bcl-2 was detected in the presence or absence of BNIP3 or BNIP3ΔTM. CNTL indicates normoxic control cells; HYPX, hypoxia.

To determine whether BNIP3 is cytotoxic and provokes cell death of ventricular myocytes, the inventors generated a replication defective adenovirus encoding full-length BNIP3. For these experiments, myocytes were stained with the vital dyes calcein-AM and ethidium homodimer-1 to mark the number of live cells green and dead cells red, respectively (Mustapha et al., 2000). As shown in FIG. 24A, a significant 8.3-fold increase (P<0.05) in myocyte death was observed in the presence of BNIP3 compared with cells infected with a control virus lacking the BNIP3 cDNA insert. Moreover, Hoechst 33258 staining for nuclear morphology revealed a significant increase in nucleosomal DNA fragmentation typical of apoptosis in the presence of BNIP3 (FIG. 24B). Importantly, the pan caspase inhibitor z-VAD-fmk (25 to 100 μmol/L) prevented BNIP3-induced cell death of ventricular myocytes in a dose dependent manner (FIG. 24C). These results corroborate the notion that BNIP3 provokes apoptosis of ventricular myocytes and suggest the involvement of a caspase-regulated pathway. Importantly, BNIP3 had no apparent effect on the expression levels of pro-death family members Bad, Bax, or Bcl-2 in ventricular myocytes (FIG. 25).

Figure 26:
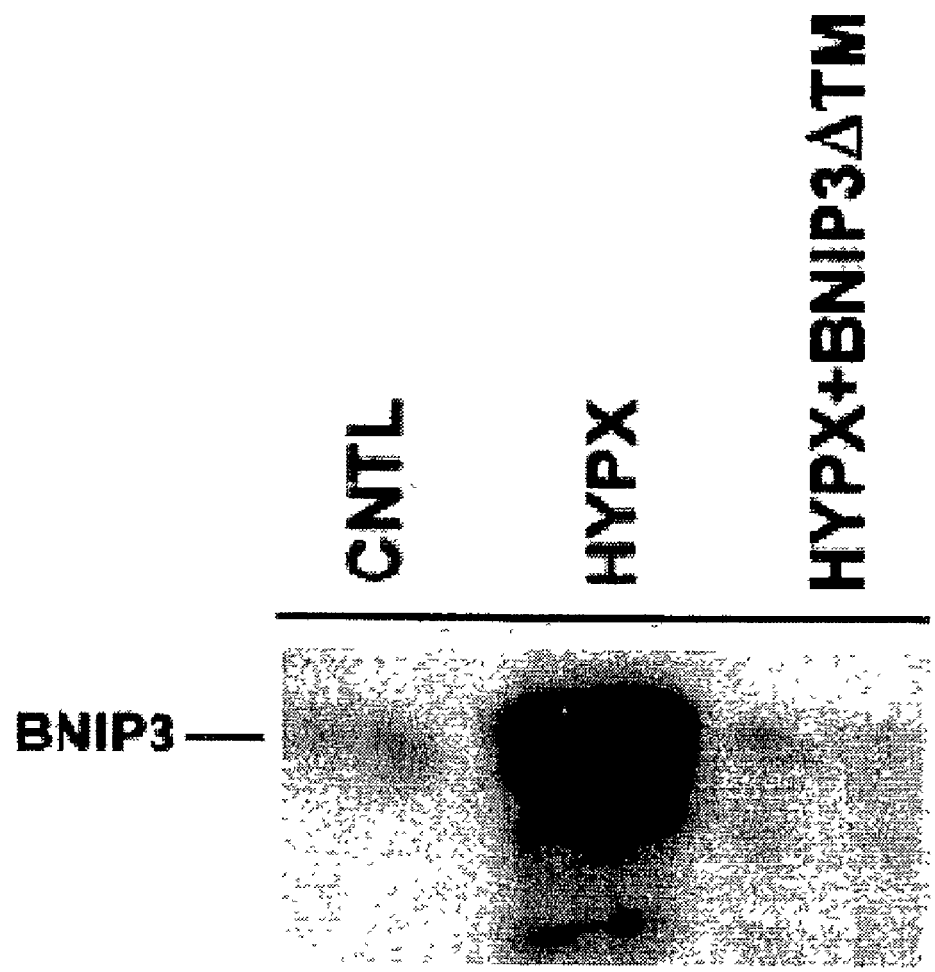
FIG. 26 shows the hypoxia-induced mitochondrial integration of the endogenous BNIP3 is suppressed by BNIP3ΔTM. Alkaline extraction of mitochondria from normoxic and hypoxic myocytes in the presence and absence of BNIP3ΔTM. Absence of detectable BNIP3 in the normoxic group indicates that BNIP3 is alkaline soluble and not integrated into mitochondrial membranes. Presence of BNIP3 after alkaline treatment of mitochondria indicates that BNIP3 is integrated into mitochondrial membranes. In the absence of BNIP3ΔTM, endogenous BNIP3 is detectable in the alkaline-treated fraction, indicating it had integrated into mitochondrial membranes. In the presence of BNIP3ΔTM after alkaline treatment, the endogenous BNIP3 was not detected in the mitochondrial fraction, indicating it was not integrated into mitochondrial membranes.

In a recent study, endogenous Bax protein was found loosely associated with mitochondria but readily integrated into mitochondrial membranes following pro-death signals (Goping et al., 1998). Similarly, we found that BNIP3 is associated with the mitochondria in normoxic cells (K. M. Regula and L. A. Kirshenbaum, unpublished data, 2002). To ascertain whether hypoxia provokes the integration of BNIP3 into mitochondrial membranes, the inventors subjected mitochondria of normoxic and hypoxic cells to alkali extraction, which will dissociate and solubilize unintegrated membrane proteins (Goping et al., 1998). After alkali extraction of mitochondria, BNIP3 was undetectable in the mitochondrial membranes of normoxic cells, indicating it was alkali soluble and not membrane integrated. In contrast, BNIP3 was readily detectable in the mitochondrial fraction of hypoxic cells after alkali extraction, suggesting that it was tightly associated with mitochondrial membranes (FIG. 26). These results indicate that hypoxia is sufficient to provoke the integration of BNIP3 protein into mitochondrial membranes. The inventors next addressed whether BNIP3 promotes mitochondrial PT changes. For these experiments, ventricular myocytes were loaded with calcein-AM in the presence of cobalt chloride to quench the cytoplasmic signal. The loss of green fluorescence is a measure of mitochondrial membrane permeability and can be used as an index of PT pore opening (Petronilli et al., 1998). As shown in FIG. 27A, control cells displayed punctate greenstaining mitochondria, indicative of the PT pore in a closed configuration; however, a marked reduction in mitochondrial fluorescence was observed in the presence of BNIP3, consistent with PT pore opening. To verify that the BNIP3-induced loss of mitochondrial calcein staining was related to PT changes, we treated cells with Bongkrekic acid (50 μmol/L), a known inhibitor of the adenine nucleotide translocator (ANT), and the PT pore (Bossy-Wetzel et al, 1998; Lemasters et al., 1998). As shown in FIG. 27A, Bongkrekic acid suppressed BNIP3-induced loss of mitochondrial calcein staining, confirming the involvement of PT pore. Together the data suggest that BNIP3 induces perturbations to mitochondria in ventricular myocytes consistent with PT pore opening.

To substantiate the conclusion that integration of BNIP3 into mitochondria is required for cell death of ventricular myocytes during hypoxia, we tested whether a carboxyl terminal transmembrane deletion mutant of BNIP3 (BNIP3ΔTM), defective for mitochondrial integration could suppress hypoxia-induced cell death of ventricular myocytes. As shown in FIG. 27B, cells expressing the BNIP3ΔTM were not different from control cells with respect to viability, indicating that the BNIP3ΔTM was not toxic to myocytes and did not provoke cell death. A 5.6-fold increase (P<0.05) in myocyte death was observed in cells subjected to hypoxia. In addition, hypoxia-induced cell death of ventricular myocytes was markedly blunted in the presence of the BNIP3ΔTM (FIGS. 27B and 27C). Importantly, BNIP3ΔTM had no apparent effect on the expression levels pro-death Bcl-2 family members or Bcl-2 expression itself (FIG. 25). These results indicate BNIP3ΔTM acts in a dominant-negative manner to block the cytotoxic actions of the endogenous BNIP3 protein. This notion is founded on the observation that hypoxia-induced mitochondrial integration of the endogenous BNIP3 protein was suppressed by the BNIP3ΔTM (FIG. 26). Collectively, the data verify the involvement of BNIP3 and the importance of mitochondrial integration during hypoxia-induced cell death of ventricular myocytes.

Discussion

The inventors provided the first direct evidence for the involvement of BNIP3 as an inducible factor that provokes mitochondrial defects and cell death of ventricular myocytes during hypoxia. Furthermore, their data indicates that BNIP3 induces cell death through a mechanism that impinges on mitochondrial PT pore. This notion is substantiated by several key observations. First, the inventors demonstrated that hypoxia is sufficient to provoke the integration of BNIP3 into mitochondrial membranes. Next, they found that BNIP3 expression in ventricular myocytes resulted in mitochondrial defects consistent with PT opening that could be suppressed by Bongkrekic acid, an inhibitor of PT pore. Lastly, BNIP3ΔTM, which is defective for mitochondrial targeting, suppressed hypoxia-induced cell death of ventricular myocytes, suggesting that this property of BNIP3 is crucial for induction of death of ventricular myocytes.

Example 9

Antisense Inhibiton of BNIP3

The inventors have designed and constructed antisense oligonucleotides directed toward BNIP3 to test the impact of inhibition of BNIP3 expression on hypoxia-mediated cell death. The results indicate that cells treated with antisense oligos sequences directed toward the BNIP3 gene sequence suppressed hypoxia-mediated cell death compared to untreated cells.

The antisense oligonucleotides that were prepared consisted of the following:

```
5' CGCCTTCCAATGTAGATCCCC 3'    (SEQ ID NO:8)

5' CCCCCTTTCTTCATAACGCTT 3'    (SEQ ID NO:9)

5' GCTGTGCGCTTCGGGTGTTA 3'     (SEQ ID NO:10)

5' CGCTGCTCCCATTCCCATTGC 3'    (SEQ ID NO:11)

5' CCCGCTCTGCGACATGGTGGC 3'    (SEQ ID NO:12)

5' GACATGGTGGCTCCGCAAAGG 3'    (SEQ ID NO:13)

5' CGCAAAGGAGCCGGAGCCCAA 3'    (SEQ ID NO:14)

5' CGACAGGCCTGGGAAGTGACC 3'    (SEQ ID NO:15)

5' TGCAGACACCCAAGGATCATG 3'    (SEQ ID NO:16)

5' GGTAATGGTGGACAGCAAGGC 3'    (SEQ ID NO:17)

5' TGCAGACACCCAAGGATCATG 3'    (SEQ ID NO 18)
```

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE I

BNIP3 constructs and deletion mutants

| Construct | Mutation (amino acid residues) |
|---|---|
| BNIP3 | None |
| BNIP3DBH3 | D104-119 |
| BNIP3DN; BH3 | D1-49; D104-119 |
| BNIP3DC | D185-194 |
| BNIP3DCD | D112-130 |
| BNIP3DN | D1-49 |
| BNIP3D50-194 | D50-194 |
| BNIP3DN; DTM | D1-49; D164-194 |
| BNIP3DTM1 | D164-184 |
| BNIP3DTM2 | D164-194 |
| BNIP3D1-12 | D1-12 |
| BNIP3D1-100 | D1-100 |
| BNIP3D1-124 | D1-124 |
| BNIP3D41-100 | D41-100 |
| BNIP3D49-151 | D49-151 |
| BNIP3D41-151 | D41-151 |
| BNIP3D58-66 | D58-66 |
| BNIP3D120-130 | D120-130 |
| BNIP3D104-130 | D104-130 |
| BNIP3D112-119 | D112-119 |
| BNIP3D65-151 | D65-151 |
| BNIP3D173-194 | D173-194 |
| BNIP3D179-184 | D179-184 |
| BNIP3D162-170 | D162-170 |
| BNIP3D183-184 | D183-184 |
| BNIP3D181-184 | D181-184 |
| BNIP3D179-194 | D179-194 |
| BNIP3D190-194 | D190-194 |
| BNIP3(P167 to S) | P167 to S |
| BNIP3(L179 to S) | L179 to S |
| BNIP3(G180 to T) | G180 to T |
| BNIP3(G180 to E) | G180 to E |
| BNIP3(A176 to V; G180 to E) | A176 to V; G180 to E |
| BNIP3(L179 to T; G180 to E | L179 to T; G180 to E |
| BNIP3-BcITM | BNIP3 (1-163) + BcITM (219-239) |
| BNIP3-CybTM | BNIP3 (1-163) + Cytob5 (100-134 |

*NOTE:
Many of these BNIP3 deletion mutants are cloned into yeast (pAS1, pACTII, pGBT9) vectors as well as mammalian expression vector pcDNA3. Furthermore pcDNA3 clones may have a 3' or 5'HA-or T7 epitope tag BNIP3 Wild Type Promoter (Seq ID No: 1)

```
ctttcccgcaag accagacacg actgtctggg aagcagcgtt tctggggcgc accttgacac ttggatttgg atcaacaatg ctttcaagaa gaaagacttt tgatcaaaag cgggaaatga gaaagcgact ttcctctgaa aagtgcctcc cagtcccgag gctgcgaggc ccccacgcca ggctggctcc cacggaagcc gggcacccac ccggacggac caagcgccac tccgccccgt ggacggggcg tcccaccccg gggacgcccg ccccacaccg cgtttgcacc ccggaggccc cttgccgcag aggcggacgg cgcgcctctc ccgggcccct ggggtccgcg cctccctcgg gcagactctt tcgactctgc tcgagcctcc gcttcttcct gcgggcggac gccccggaca caacgggccc cgctgttcac gcaggggcgc cccggcgggg cgggcaaaga cccggggacg cggtcccgtc ccgagacgct cagctccggc ccaccgctcg cagctcccgc cccgggcgca ggtcccgacc ccacgggccg tctcggagcc gcagcggccg cttccctgca cgtcctcacg cccccccgcac ggacgccgcc agcccccgcgc ctcagtttcc ccactagcag gatggaaaga cgggccccgc cccgaagcgt agcggcgtct ccgtggtagc cagtgcccag agagtccgcc ggtcccaccg cccccttcaaa ggagaacccg gcccaccgcc cgccgcggcg gcgaccgcgc agcccactcg tcacgcggcc cgcggcgtcc agcccgggcc ggctcacctc aggcggtcgc tgccgccctc gcgcctgcgc gcccctcgcc ccgcccctct ccccgcccgc gtcccgcgca ccggaggcct ctgcccctcg cccaccgcag gacccgcccc gcgcacgcgc cgcacgtgcc acacgcaccc cacgcccctg cgcacgcgca ggcccaagt cgcggccaat gggcgacgcg gccgcagatc cgcccggccc cgccctgccc tgtgagttcc tccggccggg ctgcggggct ccgctcagtc cggagcgca gctgggccgc ggcgctccga cctccgcttt cccaccgccc gcagctgaag cacatcccgc agcccggcgc ggactccgat cgccgcagtt g
```

BNIP3 D1: Deletion Mutant 1 (Seq ID No: 2)

```
tcctctgaa aagtgcctcc cagtcccgag gctgcgaggc ccccacgcca ggctggctcc cacggaagcc gggcacccac ccggacggac caagcgccac tccgccccgt ggacggggcg tcccaccccg gggacgcccg ccccacaccg cgtttgcacc ccggaggccc cttgccgcag aggcggacgg cgcgcctctc ccgggcccct ggggtccgcg cctccctcgg gcagactctt tcgactctgc tcgagcctcc gcttcttcct gcgggcggac gccccggaca caacgggccc cgctgttcac gcaggggcgc cccggcgggg cgggcaaaga cccggggacg cggtcccgtc ccgagacgct cagctccggc ccaccgctcg cagctcccgc cccgggcgca ggtcccgacc ccacgggccg tctcggagcc gcagcggccg cttccctgca cgtcctcacg cccccccgcac ggacgccgcc agcccccgcgc ctcagtttcc ccactagcag gatggaaaga cgggccccgc cccgaagcgt agcggcgtct ccgtggtagc cagtgcccag agagtccgcc ggtcccaccg
```
ccccttcaaa ggagaacccg gcccaccgcc cgccgcggcg
gcgaccgcgc agcccactcg tcacgcggcc cgcggcgtcc
agcccgggcc ggctcacctc aggcggtcgc tgccgccctc
gcgcctgcgc gcccctcgcc ccgcccctct ccccgcccgc
gtcccgcgca ccggaggcct ctgcccctcg cccaccgcag
gacccgcccc gcgcacgcgc cgcacgtgcc acacgcaccc
cacgcccctg cgcacgcgca ggcccaagt cgcggccaat
gggcgacgcg gccgcagatc cgcccggccc cgccctgccc
tgtgagttcc tccggccggg ctgcggggct ccgctcagtc
cgggagcgca gctgggccgc ggcgctccga cctccgcttt
cccaccgccc gcagctgaag cacatcccgc agcccggcgc
ggactccgat cgccgcagtt g BNIP3 D2: Deletion Mutant 2 (Seq ID No: 3)
actctt tcgactctgc tcgagcctcc gcttcttcct gcgggcggac
gccccggaca caacgggccc cgctgttcac gcaggggcgc
cccggcgggg cgggcaaaga cccggggacg cggtcccgtc
ccgagacgct cagctccggc ccaccgctcg cagctcccgc
cccgggcgca ggtcccgacc ccacgggccg tctcggagcc
gcagcggccg cttccctgca cgtcctcacg ccccccgcac
ggacgccgcc agcccgcgc ctcagtttcc ccactagcag
gatggaaaga cgggcccgc cccgaagcgt agcggcgtct
ccgtggtagc cagtgcccag agagtccgcc ggtcccaccg
ccccttcaaa ggagaacccg gcccaccgcc cgccgcggcg
gcgaccgcgc agcccactcg tcacgcggcc cgcggcgtcc
agcccgggcc ggctcacctc aggcggtcgc tgccgccctc
gcgcctgcgc gcccctcgcc ccgcccctct ccccgcccgc
gtcccgcgca ccggaggcct ctgcccctcg cccaccgcag
gacccgcccc gcgcacgcgc cgcacgtgcc acacgcaccc
cacgcccctg cgcacgcgca ggcccaagt cgcggccaat
gggcgacgcg gccgcagatc cgcccggccc cgccctgccc
tgtgagttcc tccggccggg ctgcggggct ccgctcagtc
cgggagcgca gctgggccgc ggcgctccga cctccgcttt
cccaccgccc gcagctgaag cacatcccgc agcccggcgc
ggactccgat cgccgcagtt g BNIP 3 D3: Deletion Mutant 3 (Seq ID No: 4)

gacgct cagctccggc ccaccgctcg cagctcccgc cccgggcgca
ggtcccgacc ccacgggccg tctcggagcc gcagcggccg cttccctgca cgtcctcacg ccccccgcac ggacgccgcc
agcccgcgc ctcagtttcc ccactagcag gatggaaaga
cgggcccgc cccgaagcgt agcggcgtct ccgtggtagc
cagtgcccag agagtccgcc ggtcccaccg ccccttcaaa
ggagaacccg gcccaccgcc cgccgcggcg gcgaccgcgc
agcccactcg tcacgcggcc cgcggcgtcc agcccgggcc
ggctcacctc aggcggtcgc tgccgccctc gcgcctgcgc
gcccctcgcc ccgcccctct ccccgcccgc gtcccgcgca
ccggaggcct ctgcccctcg cccaccgcag gacccgcccc
gcgcacgcgc cgcacgtgcc acacgcaccc cacgcccctg
cgcacgcgca ggcccaagt cgcggccaat gggcgacgcg
gccgcagatc cgcccggccc cgccctgccc tgtgagttcc
tccggccggg ctgcggggct ccgctcagtc cgggagcgca
gctgggccgc ggcgctccga cctccgcttt cccaccgccc
gcagctgaag cacatcccgc agcccggcgc ggactccgat
cgccgcagtt g BNIP3 D4: Deletion Mutant 4 (Seq ID No: 5) gtggtagc cagtgcccag agagtccgcc ggtcccaccg ccccttcaaa ggagaacccg
gcccaccgcc cgccgcggcg gcgaccgcgc agcccactcg
tcacgcggcc cgcggcgtcc agcccgggcc ggctcacctc
aggcggtcgc tgccgccctc gcgcctgcgc gcccctcgcc
ccgcccctct ccccgcccgc gtcccgcgca ccggaggcct
ctgcccctcg cccaccgcag gacccgcccc gcgcacgcgc
cgcacgtgcc acacgcaccc cacgcccctg cgcacgcgca
ggcccaagt cgcggccaat gggcgacgcg gccgcagatc
cgcccggccc cgccctgccc tgtgagttcc tccggccggg
ctgcggggct ccgctcagtc cgggagcgca gctgggccgc
ggcgctccga cctccgcttt cccaccgccc gcagctgaag
cacatcccgc agcccggcgc ggactccgat cgccgcagtt
g BNIP3 D5: Deletion Mutant 5 (Seq ID No: 6)

ca ccggaggcct
ctgcccctcg cccaccgcag gacccgcccc gcgcacgcgc
cgcacgtgcc acacgcaccc cacgcccctg cgcacgcgca
ggcccaagt cgcggccaat gggcgacgcg gccgcagatc
cgcccggccc cgccctgccc tgtgagttcc tccggccggg
ctgcggggct ccgctcagtc cgggagcgca gctgggccgc

```
-continued
ggcgctccga cctccgcttt cccaccgccc gcagctgaag cacatcccgc agcccggcgc ggactccgat cgccgcagtt g.
```

BNIP3 D6: Deletion Mutant 6 (Seq ID No: 7)

```
gccc tgtgagttcc tccggccggg ctgcggggct ccgctcagtc cgggagcgca gctgggccgc ggcgctccga cctccgcttt cccaccgccc gcagctgaag cacatcccgc agcccggcgc ggactccgat cgccgcagtt g
```

FULL CITATIONS FOR REFERENCES REFERRED TO IN THE SPECIFICATION

Bernardi, P., L. Scorrano, R. Colonna, V. Petronilli, and F. Di Lisa. 1999. Mitochondria and cell death: mechanistic aspects and methodological issues. Eur. J. Biochem. 264: 687-701.

Bialik, S, Cryns, V L, Drincic, A et al. The mitochondrial apoptotic pathway is activated by serum and glucose deprivation in cardiac myocytes. Circ. Res. 9-3-1999 85: 403414.

Bossy-Wetzel, E., D. D. Newmeyer, and D. R. Green. 1998. Mitochondrial cytochrome c release in apoptosis occurs upstream of DEVD-specific caspase activation and independently of mitochondrial transmembrane depolarization. EMBO J. 17: 37-49.

Boyd, J. M., S. Malstrom, T. Subramanian, L. K. Venkatesh, U. Schaeper, B. Elangovan, C. D. Sa-Eipper, and G. Chinnadurai. 1994. Adenovirus E1B 19 kDa and Bcl-2 proteins interact with a common set of cellular proteins. Cell 79: 341-351.

Burke and Olson, "Preparation of Clone Libraries in Yeast Artificial-Chromosome Vectors" in Methods in Enzy-molOlOaV, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" Science 244: 12881292 (1989).

Chautan, M., G. Chazal, F. Cecconi, P. Gruss, and P. Golstein. 1999. Interdigital cell death can occur through a necrotic and caspase-independent pathway. Curr. Biol. 9: 967-970.

Chen, G., J. Cizeau, C. Vande Velde, J. H. Park, G. Bozek, J. Bolton, L. Shi, D. Dubik, and A. Greenberg. 1999. Nix and NIP3 form a subfamily of pro-apoptotic mitochondrial proteins. J. Biol. Chem. 274: 7-10.

Chen, G., R. Ray, D. Dubik, L. F. Shi, J. Cizeau, R. C. Bleackley, S. Saxena, R. D. Gietz, and A. H. Greenberg. 1997. The E1B 19K Bcl-2-binding protein NIP3 is a dimeric mitochondrial protein that activates apoptosis. J. Exp. Med. 186: 1975-1983.

Chi, S., C. Kitanaka, K. Noguchi, T. Mochizuki, Y. Nagashima, M. Shirouzu, H. Fujita, M. Yoshida, W. Chen, A. Asai, M. Himeno, S. Yokoyama, and Y. Kuchino. 1999. Oncogenic Ras triggers cell suicide through the activation of a caspase-independent cell death program in human cancer cells. Oncogene 18: 2281-2290.

Cizeau J, Ray R, Chen G, Gietz R D, Greenberg A H. The C. elegans orthologue ceBNIP3 interacts with CED-9 and CED-3 but kills through a BH3- and caspaseindependent mechanism. Oncogene. 2000 Nov. 16; 19, (Srinivasula, S. M., et al., 1998): 5453-63.

Cregg J M, Vedvick T S, Raschke W C: Recent Advances in the Expression of Foreign Genes in Pichia pastoris, Bio/Technology 11: 905-910, 1993.

Crompton, M. 1999. The mitochondrial permeability transition pore and its role in cell death. Biochem. J. 341: 233-249.

Culver, 1998. Site-Directed recombination for repair of mutations in the human ADA gene. (Abstract) Antisense DNA & RNA based therapeutics, February, 1998, Coronado, Calif.

Datta, S. R., H. Dudek, X. Tao, S. Masters, H. A. Fu, Y. Gotoh, and M. E. Greenberg. 1997. Akt phosphorylation of BAD couples survival signals to the cell-intrinsic death machinery. Cell 91: 231-241.

Davies et al., "Targeted alterations in yeast artificial chromosomes for inter-species gene transfer", Nucleic Acids Research, Vol. 20, No. 11, pp. 2693-2698 (1992).

Deas, O., C. Dumont, M. MacFarlane, C. Rouleau, F. Hebib, F. Harper, F. Hirsch, G. M. Charpentier, G. M. Cohen, and A. Senik. 1998. Caspase-independent cell death induced by anti-CD2 or staurosporine in activated human peripheral T lymphocytes. J. Immunol. 161: 3375-3383.

de Moissac, D, Gurevich, RM, Zheng, H et al. Caspase Activation and Mitochondrial Cytochrome C Release during Hypoxia-mediated Apoptosis of Adult Ventricular Myocytes. J. Mol. Cell Cardiol. 2000 32: 53-63.

Dickinson et al., "High frequency gene targeting using insertional vectors", Human Molecular Genetics, Vol. 2, No. 8, pp. 1299-1302 (1993).

Dixon I M, Hata T, Dhalla N S. Sarcolemmal calcium transport in congestive heart failure due to myocardial infarction in rats. Am J Physiol. 1992;262: H1387-H1394.

Duff and Lincoln, "Insertion of a pathogenic mutation into a yeast artificial chromosome containing the human APP gene and expression in ES cells", Research Advances in Alzheimer's Disease and Related Disorders, 1995.

Earnshaw, W. C., L. M. Martins, and S. H. Kaufmann. 1999. Mammalian caspases: structure, activation, substrates, and functions during apoptosis. Annu. Rev. Biochem. 68: 383-424.

Finucane, D. M., E. Bossy-Wetzel, N. J. Waterhouse, T. G. Cotter, and D. R. Green. 1999. Bax-induced caspase activation and apoptosis via cytochrome c release from mitochondria is inhibitable by Bcl-xL. J. Biol. Chem. 274: 2225 2233.

Gilboa, E, Eglitis, M A, Kantoff, P W, Anderson, W F: Transfer and expression of cloned genes using retroviral vectors. BioTechniques 4 (6): 504-512, 1986.

Goping, 1. S., A. Gross, J. N. Lavoie, M. Nguyen, R. Jemmerson, K. Roth, S. J. Korsmeyer, and G. C. Shore. 1998. Regulated targeting of BAX to mitochondria. J. Cell. Biol. 143: 207-215.

Green, D. R., and J. C. Reed. 1998. Mitochondria and apoptosis. Science 281: 1309-1312.

Griffiths, G. J., L. Dubrez, C. P. Morgan, N. A. Jones, J. Whitehouse, B. M. Corfe, C. Dive, and J. A. Hickman. 1999. Cell damage-induced conformational changes of the pro-apoptotic protein bak in vivo precede the onset of apoptosis. J. Cell Biol. 144: 903-914.

Gross, A., J. M. McDonnell, and S. J. Korsmeyer. 1999. BCL-2 family members and the mitochondria in apoptosis. Genes Dev. 13: 1899-1911.

Gurevich R M, Regula K M, Kirshenbaum L A. Serpin protein CrmA suppresses hypoxia-mediated apoptosis of ventricular myocytes. Circulation. 2001; 103:1984-1991.

Huston et al, 1991 "Protein engineering of single-chain Fv analogs and fusion proteins" in Methods in Enzymology (J J Langone, ed.; Academic Press, New York, N.Y.) 203: 46-88.

Hakem, R., A. Hakem, G. S. Duncan, J. T. Henderson, M. Woo, M. S. Soengas, A. Elia, J. L. De la Pompa, D. Kagi, W. Khoo, J. Potter, R. Yoshida, S. A. Kaufman, S. W. Lowe, J. M. Penninger, and T. W. Mak. 1998. Differential requirement for caspase 9 in apoptotic pathways in vivo. Cell 94: 339352.

Harada, H., B. Becknell, M. Wilm, M. Mann, L. J. S. Huang, S. S. Taylor, J. D. Scott, and S. J. Korsmeyer. 1999. Phosphorylation and inactivation of BAD by mitochondria-anchored protein kinase A. Mol. Cell 3: 413-422.

Haughey, N. J., Nath, A., Mattson, M. P., Slevinβ, J. T. & Geiger, J. D. (2001) Journal of Neurochemistry 78, 457-467.

Horvitz, H. R. 1999. Genetic control of programmed cell death in the nematode *Caenorhabditis elegans.* Cancer Res. 59: 1701S-1706S.

Huxley et al., "The human HPRT gene on a yeast artificial chromosome is functional when transferred to mouse cells by cell fusion", Genomics, 9: 742-750 (1991).

Imazu, T., S. Shimizu, S. Tagami, M. Matsushima, Y. Nakamura, T. Miki, A. Okuyama, and Y. Tsujimoto. 1999. Bcl-2/E1 B 19 kDa-interacting protein 3-like protein (BNIP3L) interacts with Bcl-2/Bcl-xL and induces apoptosis by altering mitochondrial membrane permeability. Oncogene 18: 4523-4529.

Jakobovits et al., "Germ-line transmission and expression of a human-derived yeast artificial chromosome", Nature, Vol. 362, pp. 255-261 (1993).

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203: 88-99.

Kawahara, A., Y. Ohsawa, H. Matsumura, Y. Uchiyama, and S. Nagata. 1998. Caspase-independent cell killing by Fas-associated protein with death domain. J. Cell Biol. 143: 1353-1360.

Kerr, J. F. R., A. H. Wyllie, and A. R. Currie. 1972. Apoptosis: a basic biological phenomenon with wide-ranging implications in tissue kinetics. Br. J. Cancer 26: 239-257.

Kirshenbaum, LA, de Moissac, D. The bcl-2 gene product prevents programmed cell death of ventricular myocytes. Circulation. 1997 96: 1580-1585.

Kirshenbaum L A, Schneider M D. Adenovirus E1A represses cardiac gene transcription and reactivates DNA synthesis in ventricular myocytes, via alternative pocket protein- and p300-binding domains. J Biol Chem. 1995; 270:7791-7794.

Kirshenbaum, L A, MacLellan, W R, Mazur, W et al. Highly efficient gene transfer into adult ventricular myocytes by recombinant adenovirus. *J. Clin. Invest.* 1993 92: 381387.

Kirshenbaum L A, Singal P K. Increase in endogenous antioxidant enzymes protects hearts against reperfusion injury. Am J Physiol. 1993; 265: H484-H493.

Kitanaka, C., and Y. Kuchino. 1999. Caspase-independent programmed cell death with necrotic morphology. Cell Death Differ. 6: 508-515.

Kluck, R. M., M. Degli-Esposti, G. Perkins, T. Renken, T. Kuwana, E. Bossy-Wetzel, Y. P. Goldberg, T. D. Allen, M. J. Farber, D. R. Green, and D. D. Newmeyer. 1999. The pro-apoptotic proteins Bid and Bax cause a limited permeabilization of the mitochondrial outer membrane that is enhanced by cytosol. J. Cell. Biol. 147: 809-822.

Kroemer, G., B. Dallaporta, and M. Resche-Rigon. 1998. The mitochondrial death/life regulator in apoptosis and necrosis. Annu. Rev. Physio. 60: 619642.

Kroemer, G., N. Zamzami, and S. A. Susin. 1997. Mitochondrial control of apoptosis. Immunol. Today 18: 44-51.

Lamb et al., "Introduction and expression of the 400 kilobase precursor amyloid protein gene in transgenic mice", Nature Genetics, Vol. 5, pp. 22-29 (1993).

Lavoie, J. N., M. Nguyen, R. C. Marcellus, P. E. Branton, and G. C. Shore. 1998. E4orf4, a novel adenovirus death factor that induces p53-independent apoptosis by a pathway that is not inhibited by zVAD-fmk. J. Cell Biol. 140: 637-645.

Leist, M., B. Single, A. F. Castoldi, S. Kuhnle, and P. Nicotera. 1997. Intracellular adenosine triphosphate (ATP) concentration: a switch in the decision between apoptosis and necrosis. J. Exp. Med. 185: 1481-1486.

Lemasters, J. J., A. L. Nieminen, T. Qian, L. C. Trost, S. P. Elmore, Y. Nishimura, R. A. Crowe, W. E. Cascio, C. A. Bradham, D. A. Brenner, and B. Herman. 1998. The mitochondrial permeability transition in cell death: a common mechanism in necrosis, apoptosis and autophagy. Biochim. Biophys. Acta 1366: 177-196.

Lemasters J J, Qian T, Elmore S P, Trost L C, Nishimura Y, Herman B, Bradham C A, Brenner D A, Nieminen A L. Confocal microscopy of the mitochondrial permeability transition in necrotic cell killing, apoptosis and autophagy. Biofactors. 1998; 8:283-285.

Li, H., H. Zhu, C. J. Xu, and J. Yuan. 1998. Cleavage of BID by caspase 8 mediates the mitochondrial damage in the Fas pathway of apoptosis. Cell 94: 491-501.

Li, P., D. Nijhawan, I. Budihardjo, S. M. Srinivasula, M. Ahmad, E. S. Alnemri, and X. D. Wang. 1997. Cytochrome c and dATP-dependent formation of Apaf-1/caspase-9 complex initiates an apoptotic protease cascade. Cell 91: 479-489.

Long X, Boluyt M O, Hipolito M L, Lundberg M S, Zheng J S, O'Neill L, Cirielli C, Lakatta E G, Crow M T. p53 and the hypoxia-induced apoptosis of cultured neonatal rat cardiac myocytes. J Clin Invest. 1997; 99:2635-2643.

Luo, X., I. Budihardjo, H. Zou, C. Slaughter, and X. Wang. 1998. Bid, a Bcl2 interacting protein, mediates cytochrome c release from mitochondria in response to activation of cell surface death receptors. Cell 94: 481-490.

Marzo, I., C. Brenner, N. Zamzami, J. M. Juergensmeier, S. A. Susin, H. L. A. Vieira, M. C. Prevost, Z. H. Xie, S. Matsuyama, J. C. Reed, and G. Kroemer. 1998. Bax and adenine nucleotide translocator cooperate in the mitochondrial control of apoptosis. Science 281: 2027-2031.

Marzo, I., C. Brenner, N. Zamzami, S. A. Susin, G. Beutner, D. Brdiczka, R. Remy, Z. H. Xie, J. C. Reed, and G. Kroemer. 1998. The permeability transition pore complex : A target for apoptosis regulation by caspases and Bcl-2-related proteins. J. Exp. Med. 187: 1261-1271.

Matsushima, M., T. Fujiwara, E. Takahashi, T. Minaguchi, Y. Eguchi, Y. Tsujimoto, K. Suzumori, and Y. Nakamura. 1998. Isolation, mapping, and functional analysis of a novel human cDNA (BNIP3L) encoding a protein homologous to human NIP3. Genes Chromosomes Cancer 21: 230-235.

McCarthy, N. J., M. K. B. Whyte, C. S. Gilbert, and G. I. Evan. 1997. Inhibition of Ced-3/ICE-related proteases does not prevent cell death induced by oncogenes, DNA damage, or the Bcl-2 homologue Bak. J. Cell Biol. 136: 215-227.

McConkey, D. J. 1998. Biochemical determinants of apoptosis and necrosis. Toxicol. Lett. 99: 157-168.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359-365.

Miura, M., H. Zhu, R. Rotello, E. A. Hartwieg, and J. Yuan. 1993. Induction of apoptosis in fibroblasts by IL-1 beta-converting enzyme, a mammalian homolog of the *C. elegans* cell death gene ced2. Cell 75: 653-660.

Moissac D, Gurevich R M, Zheng H, Singal P K, Kirshenbaum L A. Caspase activation and mitochondrial cytochrome c release during hypoxia-mediated apoptosis of adult ventricular myocytes. J Mol Cell Cardiol. 2000;32: 53-63.

Mustapha S, Kirshner A, de Moissac D, Kirshenbaum L A. A direct requirement of nuclear factor- B for suppression of apoptosis in ventricular myocytes. Am J Physiol Heart Circ Physiol. 2000; 279:H939-H945.

Narita, M., S. Shimizu, T. Ito, T. Chittenden, R. J. Lutz, H. Matsuda, and Y. Tsujimoto. 1998. Bax interacts with the permeability transition pore to induce permeability transition and cytochrome c release in isolated mitochondria. Proc. Natl. Acad. Sci. USA 95: 14681-14686.

Nguyen, M., D. G. Millar, V. W. Yong, S. J. Korsmeyer, and G. C. Shore. 1993. Targeting of Bcl-2 to the mitochondrial outer membrane by a COOH-terminal signal anchor sequence. J. Biol. Chem. 268: 25265-25268.

Nicotera, P., M. Leist, and E. Ferrando-May. 1998. Intracellular ATP, a switch in the decision between apoptosis and necrosis. Toxicol. Lett. 102103: 139-142.

Ohi, N., A. Tokunaga, H. Tsunoda, K. Nakano, K. Haraguchi, K. Oda, N. Motoyama, and T. Nakajima. 1999. A novel adenovirus E1B19K-binding. VOL. 20,2000 BNIP3 INDUCES NECROSIS-LIKE CELL DEATH 5467.

Paxinos, G. & Watson, C. (1986) The Rat in Stereotaxic Coordinates (Academic, New York).

Pearson and Choi, Expression of the human b-amyloid precursor protein gene from a yeast artificial chromosome in transgenic mice. Proc. Natl. Acad. Sci. USA, 1993. 90: 10578-82.

Petronilli, V, Miotto, G, Canton, M et al. Imaging the mitochondrial permeability transition pore in intact cells. Biofactors 1998 8: 263-272.

Ray R, Chen G, Vande Velde C, Cizeau J, Park J H, Reed J C, Gietz R D, Greenberg A H. BNIP3 heterodimerizes with Bcl-2/Bcl-X (L) and induces cell death independent of a Bcl-2 homology 3 (BH3) domain at both mitochondrial and nonmitochondrial sites. J Biol Chem. 2000 Jan. 14; 275 (2): 1439-48.

Rothstein, "Targeting, disruption, replacement, and allele rescue: integrative DNA transformation in yeast" in Methods in Enzvmoloav, Vol. 194, "Guide to Yeast Genetics and Molecular Biology", eds. C. Guthrie and G. Fink, Academic Press, Inc., Chap. 19, pp. 281-301 (1991).

Schedl et al., "A yeast artificial chromosome covering the tyrosinase gene confers copy number-dependent expression in transgenic mice", Nature, Vol. 362, pp. 258261 (1993).

Strauss et al., "Germ line transmission of a yeast artificial chromosome spanning the murine ai (I) collagen locus", Science, Vol. 259, pp. 1904-1907 (1993).

Tanaka M, Ito H, Adachi S, Akimoto H, Nishikawa T, Kasajima T, Marumo F, Hiroe M. Hypoxia induces apoptosis with enhanced expression of Fas antigen messenger RNA in cultured neonatal rat cardiomyocytes. Circ Res. 1994; 75:426-433.

Vande Velde C, Cizeau J, Dubik D, Alimonti J, Brown T, Israels S, Hakem R, Greenberg A H. BNIP3 and genetic control of necrosis-like cell death through the mitochondrial permeability transition pore. Mol Cell Biol. 2000 Aug.; 20 (15): 5454-68.

We claim:

1. A method of inhibiting cell necrosis comprising administering an effective amount of a BNIP3 mutant protein selected from the group consisting of BNIP3ΔTM, comprising amino acids 1-163 of SEQ ID NO: 19, and BNIP3$^{3-163}$, comprising amino acids 3-163 of SEQ ID NO: 19, to a cell or animal.

2. A method according to claim 1 wherein the BNIP3 mutant protein is BNIP3$^{3-163}$, comprising amino acids 3-163 of SEQ ID NO: 19.

3. A method according to claim 1 wherein the BNIP3 mutant protein is BNIP3ΔTM, comprising amino acids 1-163 of SEQ ID NO:19.

4. A method according to claim 1 to treat a cardiovascular disease.

5. A method according to claim 1 wherein the BNIP3 mutant protein is administered as a nucleic acid that encodes the BNIP3 mutant protein to the cell in vitro.

6. A method according to claim 5 wherein the nucleic acid is comprised in an adenoviral vector.

7. A method according to claim 6 wherein the adenoviral vector is Adenop53TK.

8. A method according to claim 6 wherein the adenoviral vector is Ad CrmA.

9. A method of suppressing or inhibiting the death of a cardiovascular cell comprising administering an effective amount of a BNIP3 mutant protein selected from the group consisting of BNIP3ΔTM, comprising amino acids 1-163 of SEQ ID NO: 19, and BNIP3$^{3-163}$, comprising amino acids 3-163 of SEQ ID NO: 19, to a cell or animal.

10. A method according to claim 9 wherein the method suppresses or inhibits hypoxia-induced cell death of the cardiovascular cell.

11. A method according to claim 10 wherein the cardiovascular cell is a cardiac myocyte, ventricular myocyte, atrial myocyte, cardiac stem cell, endothelial cell, vascular smooth muscle cell, pacemakers cell, myofibroblast or fibroblast.

12. A method according to claim 11 wherein the cardiovascular cell is a cardiac myocyte.

13. A method according to claim 9 wherein the BNIP3 mutant protein is BN1P3$^{3-163}$, comprising amino acids 3-163 of SEQ ID NO: 19.

14. A method according to claim 9 wherein the BNIP3 mutant protein is BNIP3ΔTM, comprising amino acids 1-163 of SEQ ID NO: 19.

15. A method according to claim 9 for treating a cardiovascular disease.

16. A method according to claim 15 wherein the cardiovascular disease is selected from the group consisting of cardiac hypoxia, cardiac hypoxia-reoxygenation, cardiac ischemia-reperfusion injury, ischemic heart disease, heart failure, heart hypertrophy, vascular defects, congenital heart (defects) disease, and chemotherapeutic induced cardiomyopathy.

17. A method according to claim 16 wherein the BNIP3 mutant protein is administered as a nucleic acid that encodes the BNIP3 mutant protein to the cell in vitro.

18. A method according to claim 17 wherein the nucleic acid is comprised in an adenoviral vector.

19. A method according to claim 18 wherein the adenoviral vector is Adenop53TK.

20. A method according to claim 18 wherein the adenoviral vector is Ad CrmA.

21. A method according to claim 9 wherein the BNIP3 mutant protein is administered as a nucleic acid that encodes the BNIP3 mutant protein to the cell in vitro.

22. A method according to claim 21 wherein the nucleic acid is comprised in an adenoviral vector.

23. A method according to claim 22 wherein the adenoviral vector is Adenop53TK.

24. A method according to claim 22 wherein the adenoviral vector is Ad CrmA.

25. A method of inhibiting hypoxia-induced cell death comprising administering an effective amount of a BNIP3 mutant protein selected from the group consisting of BNIP3ΔTM, comprising amino acids 1-163 of SEQ ID NO: 19, and BN1P3$^{3-163}$, comprising amino acids 3-163 of SEQ ID NO: 19, to a cell or animal.

* * * * *